(12) United States Patent
Matityahu et al.

(10) Patent No.: US 10,945,804 B2
(45) Date of Patent: Mar. 16, 2021

(54) STERILIZATION TRAY FOR HOLDING IMPLANT INSERTION DEVICE FOR ATTACHMENT TO IMPLANTABLE DEVICE AND RELATED DEVICES

(71) Applicant: EPIX ORTHOPAEDICS, INC., Los Altos, CA (US)

(72) Inventors: Amir M Matityahu, Los Altos, CA (US); Benjamin Clawson, Santa Cruz, CA (US); Alan Grantz, Aptos, CA (US); John McDermott, Santa Cruz, CA (US)

(73) Assignee: Epix Orthopaedics, Inc., Los Altos, CA (US)

( * ) Notice: Subject to any disclaimer, the term of this patent is extended or adjusted under 35 U.S.C. 154(b) by 117 days.

(21) Appl. No.: 15/799,994

(22) Filed: Oct. 31, 2017

(65) Prior Publication Data
US 2018/0116747 A1    May 3, 2018

Related U.S. Application Data

(60) Provisional application No. 62/415,466, filed on Oct. 31, 2016.

(51) Int. Cl.
*A61B 17/72* (2006.01)
*A61B 50/33* (2016.01)
(Continued)

(52) U.S. Cl.
CPC .......... *A61B 50/33* (2016.02); *A61B 17/1725* (2013.01); *A61B 17/744* (2013.01);
(Continued)

(58) Field of Classification Search
CPC ......... A61B 50/00; A61B 50/30; A61B 50/33; A61B 50/34; A61B 2050/3006–3009;
(Continued)

(56) References Cited

U.S. PATENT DOCUMENTS 4,854,475 A * 8/1989 Riihimaki ................. A61L 2/26
                                                        206/369
5,800,546 A * 9/1998 Marik ........................ A61F 2/40
                                                        606/100
(Continued)

FOREIGN PATENT DOCUMENTS

WO      WO-9730737 A1    8/1997

OTHER PUBLICATIONS

International Search Report for Application No. PCT/US2017/59405, dated Mar. 6, 2018, pp. 1-4.
(Continued)

*Primary Examiner* — Eduardo C Robert
*Assistant Examiner* — Michelle C Eckman
(74) *Attorney, Agent, or Firm* — Intellectual Innovations Legal Advisors

(57) ABSTRACT

An apparatus including a sterilizable tray having a base and at least one fixture connected to the tray adapted for removably securing an implant insertion device to the tray. The tray can be free of a first wall portion for permitting the proximal end of an implantable device to axially align with the end of the implant insertion device for coupling to the implant insertion device and can be free of a second wall portion for permitting a tool to axially align with the end of the implant insertion device so as to threadedly couple the implant insertion device to the implantable device. Related methods and apparatus are provided.

19 Claims, 35 Drawing Sheets

(51) Int. Cl.
| | |
|---|---|
| *A61B 50/20* | (2016.01) |
| *A61B 50/34* | (2016.01) |
| *A61B 17/86* | (2006.01) |
| *A61B 17/88* | (2006.01) |
| *A61B 17/17* | (2006.01) |
| *A61B 17/74* | (2006.01) |
| *A61B 90/70* | (2016.01) |
| *A61B 90/00* | (2016.01) |
| *A61L 2/26* | (2006.01) |
| *A61B 50/30* | (2016.01) |
| *A61B 50/00* | (2016.01) |
| *A61B 17/00* | (2006.01) |
| *A61B 17/92* | (2006.01) |
| *A61B 17/90* | (2006.01) |

(52) U.S. Cl.
CPC .......... *A61B 17/748* (2013.01); *A61B 17/865* (2013.01); *A61B 17/8872* (2013.01); *A61B 50/20* (2016.02); *A61B 50/34* (2016.02); *A61B 90/08* (2016.02); *A61B 90/70* (2016.02); *A61L 2/26* (2013.01); *A61B 17/72* (2013.01); *A61B 17/921* (2013.01); *A61B 2017/00469* (2013.01); *A61B 2017/90* (2013.01); *A61B 2050/0056* (2016.02); *A61B 2050/3008* (2016.02); *A61B 2090/067* (2016.02); *A61B 2090/0813* (2016.02); *A61L 2202/24* (2013.01)

(58) Field of Classification Search
CPC ....... A61B 17/72–7291; A61B 17/865; A61M 5/002
USPC ......................................... 206/370, 363, 570
See application file for complete search history.

(56) References Cited

U.S. PATENT DOCUMENTS

| | | | | | |
|---|---|---|---|---|---|
| 6,116,452 | A * | 9/2000 | Hamel | ...................... | A61L 2/26 206/370 |
| 7,021,485 | B1 * | 4/2006 | Baker | ...................... | A61L 2/26 220/326 |
| 8,079,468 | B2 * | 12/2011 | Pleil | ...................... | A61B 90/04 206/339 |
| 10,028,798 | B1 * | 7/2018 | Healey | ................... | A61B 50/30 |
| 10,045,822 | B2 * | 8/2018 | Kyseliov | ................ | A61B 50/30 |
| 10,390,867 | B2 * | 8/2019 | Sixto | ................ | A61B 17/865 |
| 2002/0161446 | A1 | 10/2002 | Bryan et al. | | |
| 2006/0213794 | A1 * | 9/2006 | Foreman | ................... | A61L 2/26 206/370 |
| 2006/0266666 | A1 * | 11/2006 | Bettenhausen | ........... | A61L 2/18 206/370 |
| 2007/0104609 | A1 * | 5/2007 | Powell | ...................... | A61L 2/26 422/1 |
| 2007/0205123 | A1 * | 9/2007 | Bettenhausen | ........ | A61B 50/34 206/363 |
| 2008/0314789 | A1 * | 12/2008 | Thomas | .................... | A61L 2/26 206/572 |
| 2009/0062797 | A1 * | 3/2009 | Huebner | ............ | A61B 17/7225 606/62 |
| 2009/0099571 | A1 * | 4/2009 | Cresina | ................. | A61B 17/17 606/96 |
| 2009/0146032 | A1 * | 6/2009 | Bettenhausen | ........ | A61B 50/34 248/220.31 |
| 2009/0299375 | A1 | 12/2009 | Wack et al. | | |
| 2010/0176016 | A1 * | 7/2010 | Pell | ........................ | A61B 50/20 206/370 |
| 2010/0300910 | A1 * | 12/2010 | Hawkes | .................... | A61L 2/26 206/363 |
| 2011/0060336 | A1 * | 3/2011 | Pool | ................... | A61B 17/1725 606/57 |
| 2011/0071572 | A1 * | 3/2011 | Sixto | ................. | A61B 17/8014 606/286 |
| 2011/0155599 | A1 * | 6/2011 | Yakel | ................... | A61B 50/362 206/365 |
| 2011/0186456 | A1 * | 8/2011 | Bertazzoni | ........... | A61B 17/154 206/438 |
| 2012/0085720 | A1 * | 4/2012 | Bettenhausen | ........... | A61L 2/26 211/85.13 |
| 2013/0213843 | A1 | 8/2013 | Knight et al. | | |
| 2014/0021079 | A1 * | 1/2014 | Koller | ................... | A47F 7/0028 206/370 |
| 2014/0052132 | A1 * | 2/2014 | Matityahu | .......... | A61B 17/1725 606/62 |
| 2014/0058446 | A1 * | 2/2014 | Bernstein | ........... | A61B 17/7059 606/246 |
| 2014/0069841 | A1 * | 3/2014 | Pizzato | .................... | A61F 17/00 206/570 |
| 2014/0083886 | A1 * | 3/2014 | Winterrowd | ........... | A61B 50/34 206/370 |
| 2014/0214045 | A1 | 7/2014 | Felder et al. | | |
| 2014/0339114 | A1 * | 11/2014 | Griffin | ................... | A61B 50/30 206/370 |
| 2014/0371799 | A1 * | 12/2014 | Sixto | ................. | A61B 17/8057 606/281 |
| 2015/0021221 | A1 * | 1/2015 | Hendrickson | .......... | A61B 50/20 206/438 |
| 2015/0129524 | A1 * | 5/2015 | Cushion | .................... | A61L 2/00 211/85.13 |
| 2015/0151017 | A1 * | 6/2015 | Tipton | ...................... | A61L 2/26 422/310 |
| 2016/0015456 | A1 * | 1/2016 | Lober | ...................... | A61L 2/26 422/26 |
| 2016/0111886 | A1 * | 4/2016 | Sherman | .................. | H02J 50/10 307/104 |
| 2016/0183994 | A1 * | 6/2016 | Quach | .................. | A61B 17/8866 606/90 |
| 2016/0235454 | A1 * | 8/2016 | Treace | ................ | A61B 17/8061 |
| 2016/0249995 | A1 * | 9/2016 | Ritchey | ................ | A61B 17/865 53/425 |
| 2017/0224434 | A1 * | 8/2017 | Schwartzbauer | ....... | A61B 50/33 |
| 2018/0008364 | A1 * | 1/2018 | Orr | ........................ | A61B 50/20 |
| 2018/0028703 | A1 * | 2/2018 | McLaughlin | ............. | A61L 2/26 |
| 2018/0064507 | A1 * | 3/2018 | Kieser | ................. | A61B 17/864 |
| 2018/0140339 | A1 * | 5/2018 | Silva | ............... | A61B 17/8863 |
| 2018/0153639 | A1 * | 6/2018 | Wehrle | ............... | G06K 7/10188 |
| 2018/0206933 | A1 * | 7/2018 | Healey | ................. | A61B 17/865 |
| 2018/0249943 | A1 * | 9/2018 | Moein | .................... | A61F 17/00 |

OTHER PUBLICATIONS

Written Opinion for Application No. PCT/US2017/59405, dated Mar. 6, 2018, pp. 1-7.

\* cited by examiner

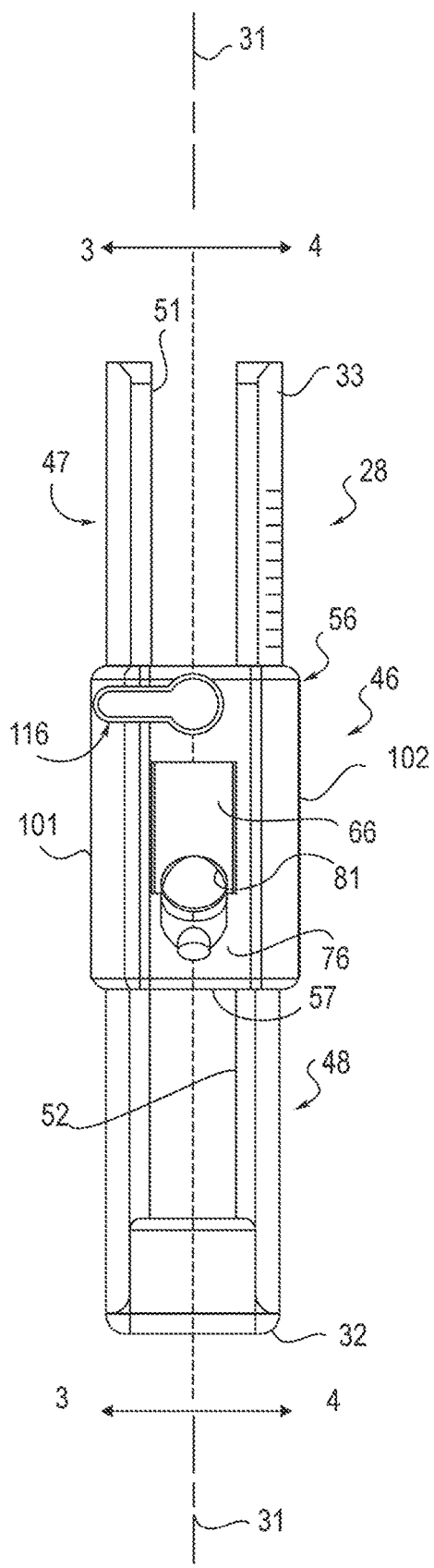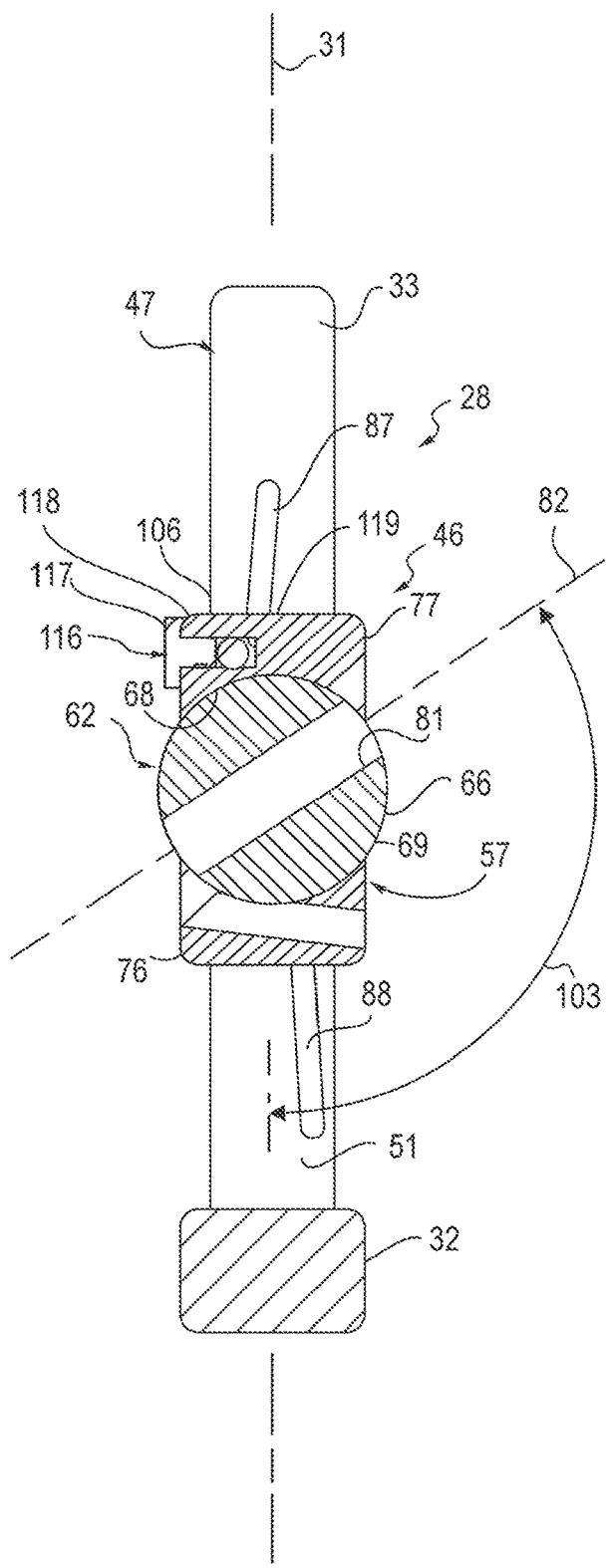

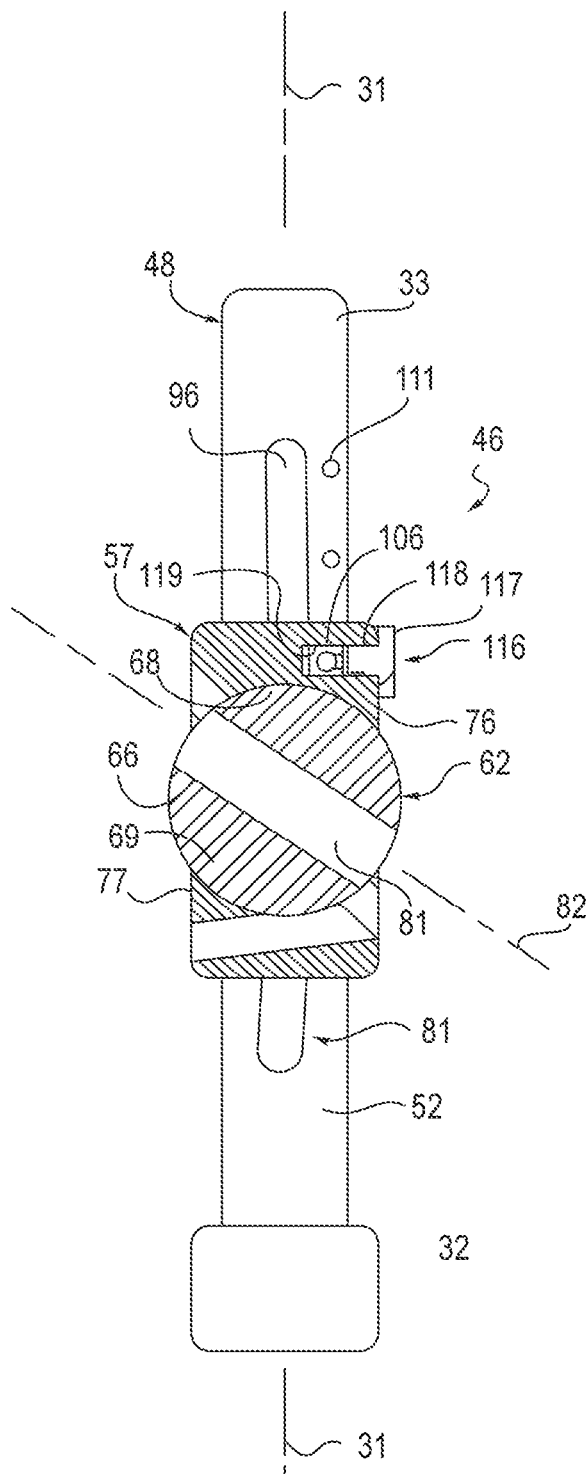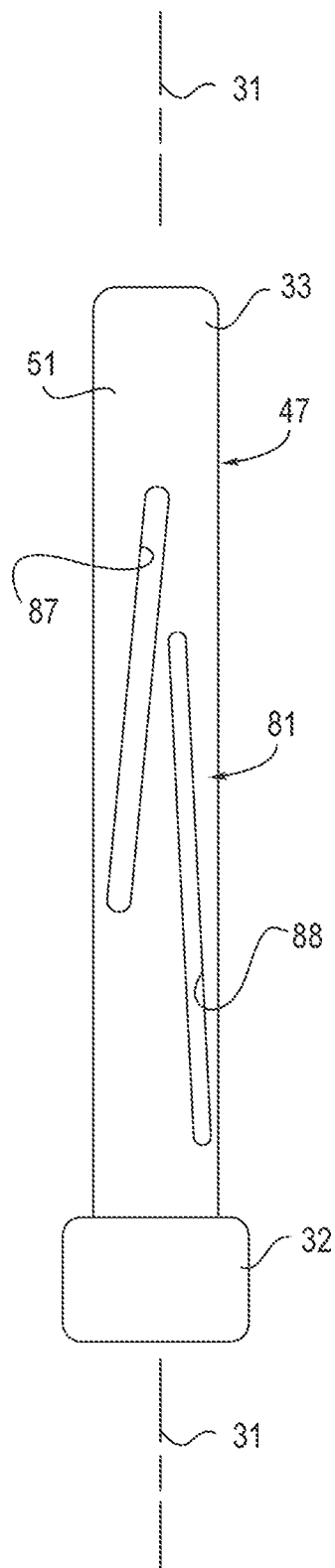
FIG. 4
FIG. 5

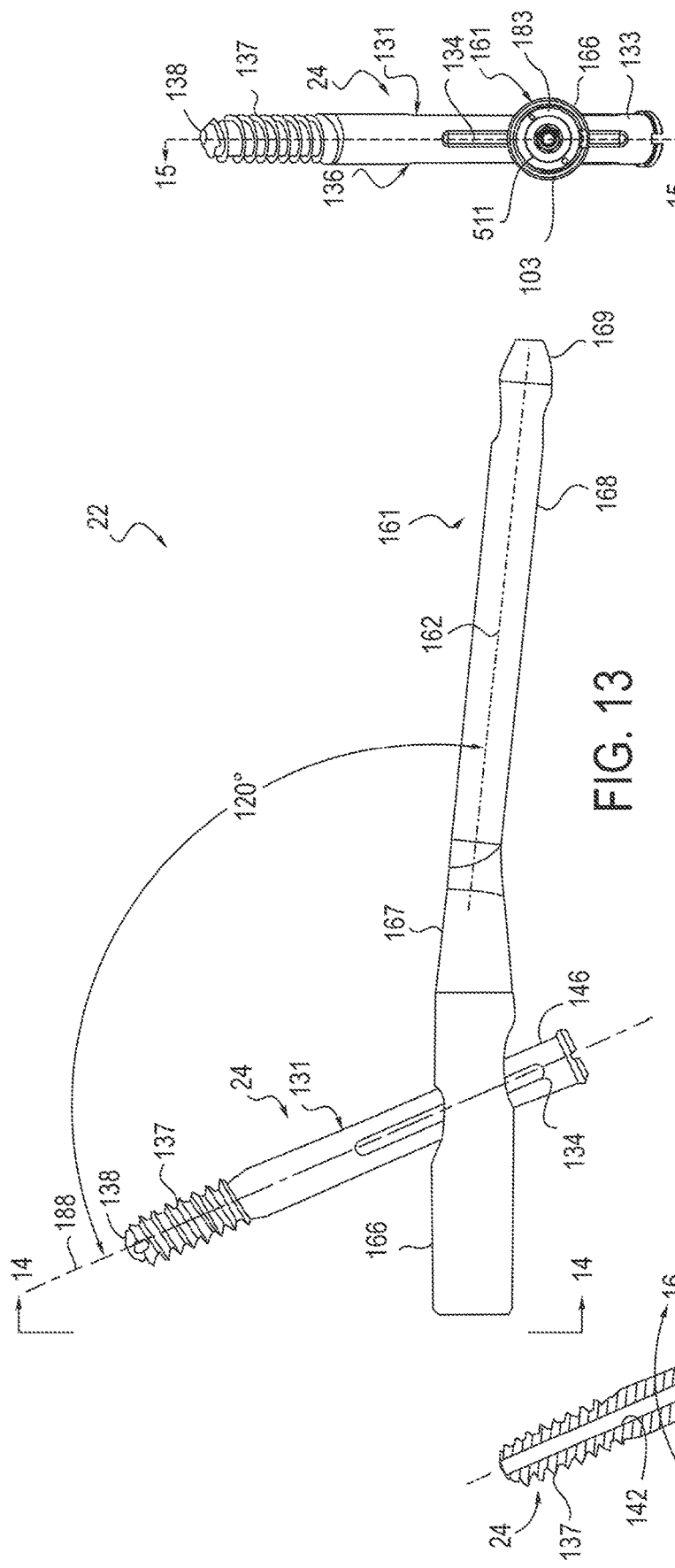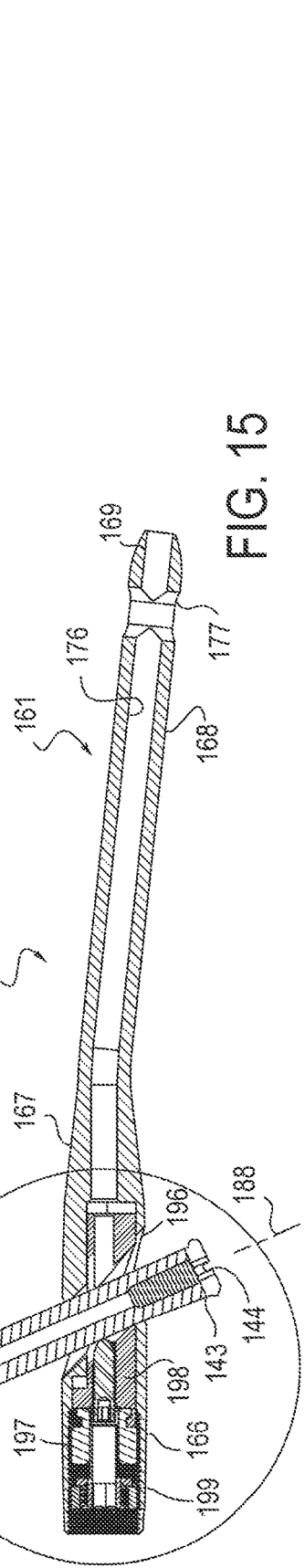
FIG. 13
FIG. 14
FIG. 15

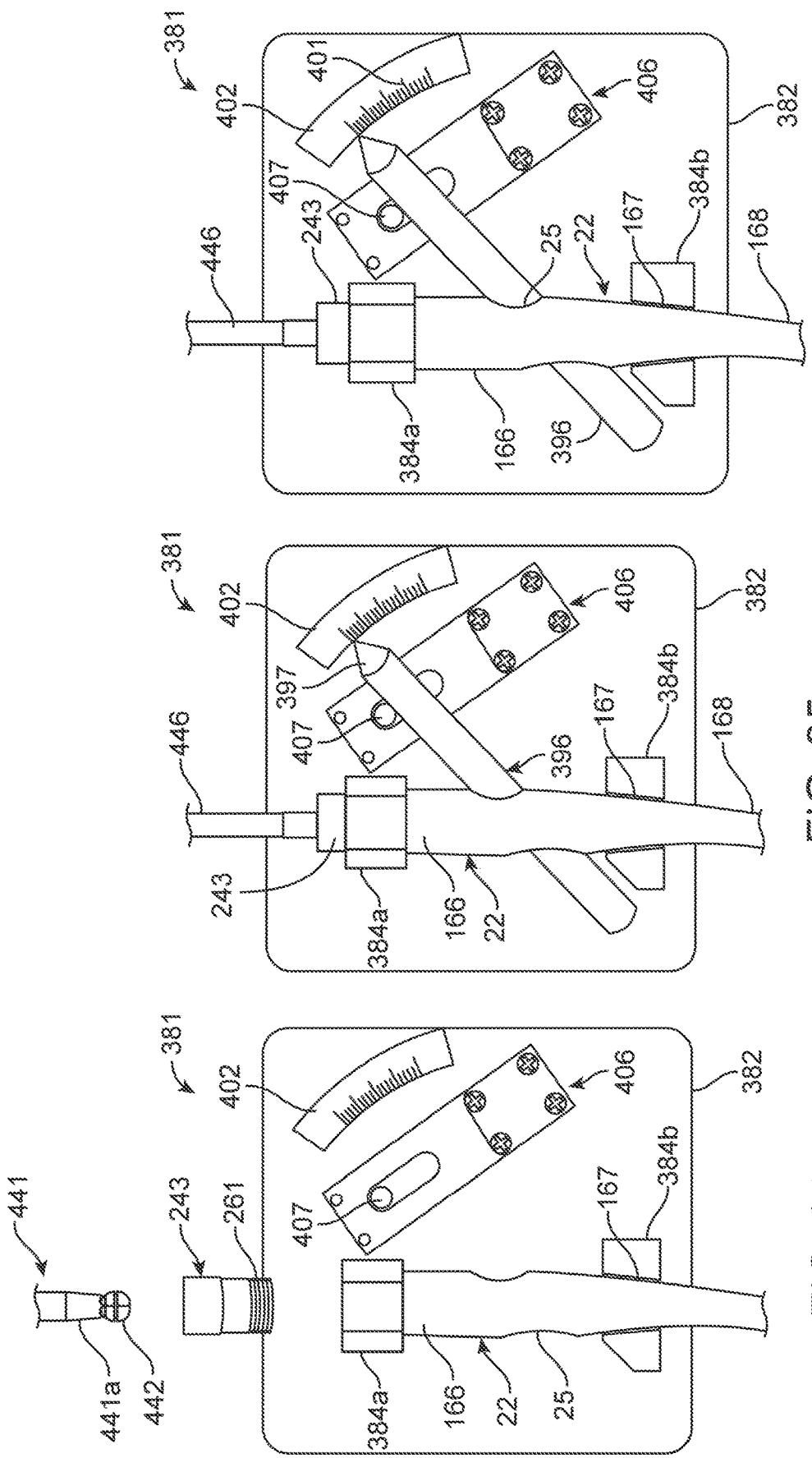

STERILIZATION TRAY FOR HOLDING IMPLANT INSERTION DEVICE FOR ATTACHMENT TO IMPLANTABLE DEVICE AND RELATED DEVICES

CROSS REFERENCE TO RELATED APPLICATION

The application claims priority to U.S. provisional application Ser. No. 62/415,466 filed Oct. 31, 2016, the entire content of which is incorporated herein by this reference.

FIELD OF THE INVENTION

The present invention relates to instrument sterilization trays for use with implant insertion devices and, more particularly, to instrument sterilization trays for use with devices that insert intramedullary nails into bones.

BACKGROUND OF THE INVENTION

Intramedullary rods or nails have been used to treat femoral, tibial, humeral and other bone fractures. One or two angled cross-nails or locking screws are inserted through the bone at the proximal and distal ends of the intramedullary rod. Rods have been provided that permit the angle of the proximal screw relative to the rod to be adjusted in situ.

Implant insertion devices, such as targeting guides, have been provided for introducing intramedullary rods into bones. Such devices can align a guide sleeve, with a locking screw inserted through the guide sleeve, relative to the bone so as to insert the screw into the nail and bone.

Instrument sterilization trays have been provided for use with implant insertion devices.

There is a need for an improved instrument sterilization tray that facilitates preoperative procedures with respect to intramedullary rods and implant insertion devices. Additionally, there is a need for an improved instrument sterilization tray that facilitates the attachment of an intramedullary rod to an implant insertion device.

BRIEF DESCRIPTION OF THE DRAWINGS

The drawings described herein are for illustration purposes only and are not intended to limit the scope of the present disclosure in any way.

FIG. 2 is an end view of a portion of the implant insertion device of FIG. 1 taken along the line 2-2 of FIG. 1 but with the continuously adjustable targeting assembly in a second position.

FIG. 3 is a cross-sectional view of the portion of the implant insertion device illustrated in FIG. 2 taken along the line 3-3 of FIG. 2.

FIG. 4 is a cross-sectional view of the portion of the implant insertion device illustrated in FIG. 2 taken along the line 4-4 of FIG. 2.

FIG. 5 is a plan view of a guide member of the portion of the implant insertion device illustrated in FIG. 2 and partially visible in FIG. 3.

FIG. 13 is a rear view of an embodiment of the intramedullary rod with a pivotable fastener for use with the implant insertion device of FIG. 1.

FIG. 14 is a top end view of the intramedullary rod with a pivotable fastener of FIG. 13 taken along the line 14-14 of FIG. 13.

FIG. 15 is a cross-sectional view of the intramedullary rod with a pivotable fastener of FIG. 13 taken along the line 15-15 of FIG. 14.

FIG. 34 is an illustration of a step of using the angle adjustment assembly of FIG. 25.

FIG. 35 is an illustration of another step of using the angle adjustment assembly of FIG. 25.

FIG. 36 is an illustration of a further step of using the angle adjustment assembly of FIG. 25.

FIG. 37 is a top plan view of the angle adjustment assembly of FIG. 25 in use in a first position.

DETAILED DESCRIPTION OF THE INVENTION

Figure 1:
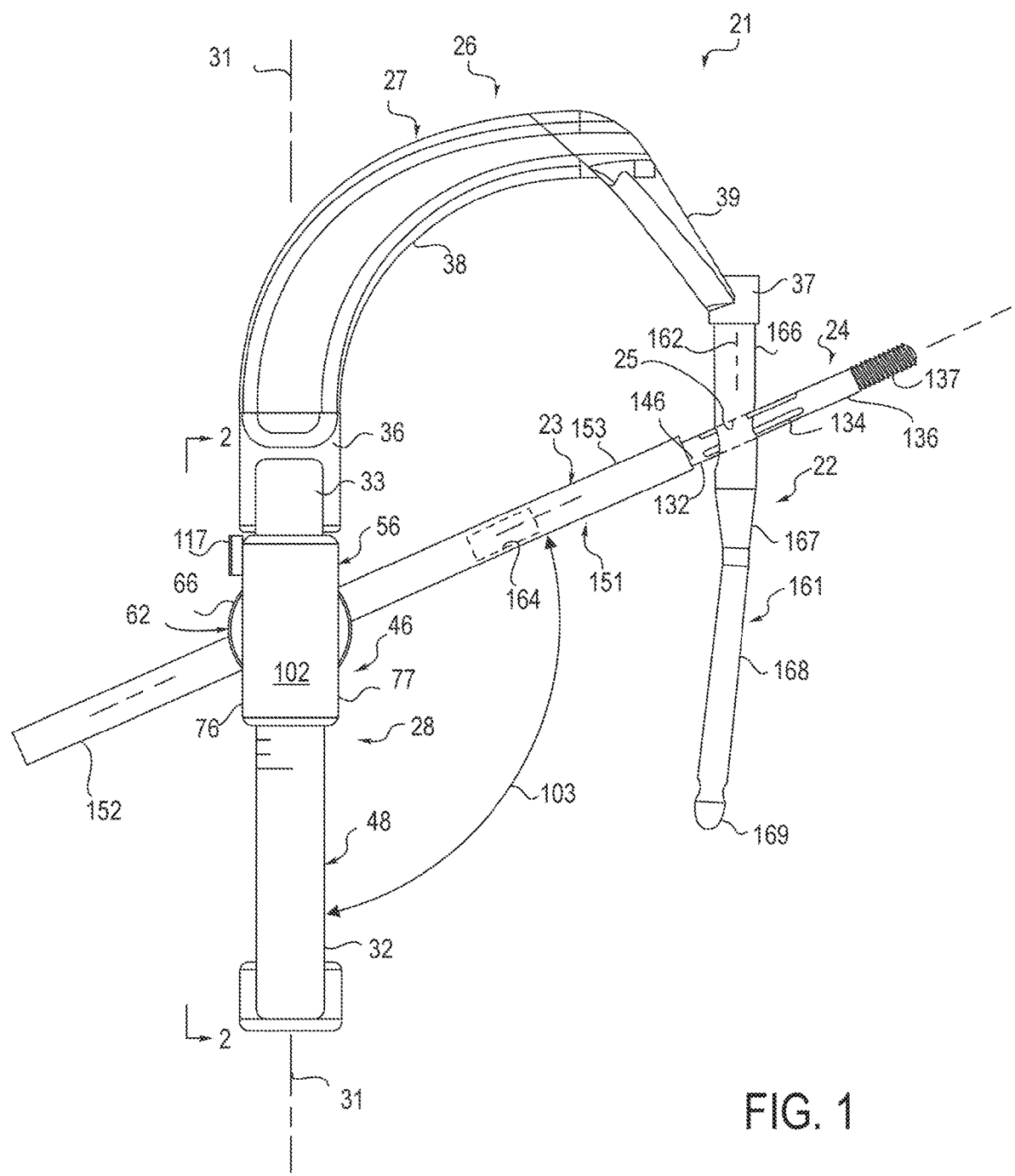
FIG. 1 is a side plan view of an implant insertion device with a continuously adjustable targeting assembly in a first position and an implantable device for use with the sterilization tray of the present invention.
Figure 6:
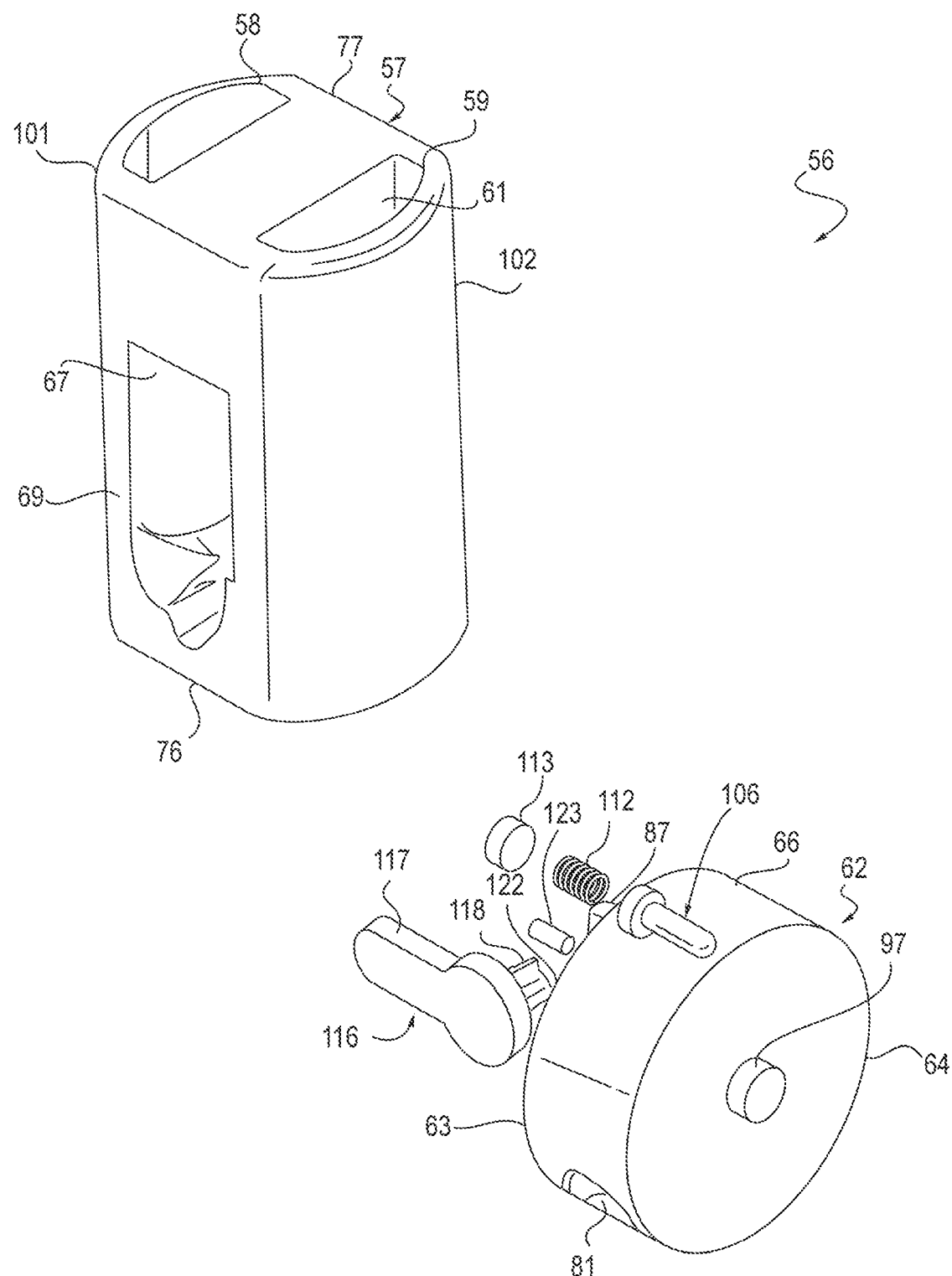
FIG. 6 is an exploded perspective view of a portion of the continuously adjustable targeting assembly of the implant insertion device of FIG. 1.

In one invention herein, a sterilizable tray assembly for medical instruments is provided. In any embodiment, a sterilizable instrument tray can be provided for carrying an implant insertion device and retaining the implant insertion device during attachment of an implantable device to the implant insertion device. In any embodiment, the implant insertion device can include an adjustable targeting assembly. In any embodiment, the implantable device can be an intramedullary nail. In one invention herein, a bolt installation driver with a guide extension is provided for facilitating attachment of an implantable device to an implant insertion device. In one invention herein, an angle adjustment mechanism is provided for presetting the adjustable aperture angle of an implantable device for receiving a fastener. In one invention herein, a sterilizable instrument tray is provided for holding an implant insertion device and presetting the angle of an adjustable targeting assembly of the implant insertion device to an adjustable aperture angle of an implant device for receiving a fastener that is secured to the implant insertion device. In one invention herein, a screw holder is provided with stepped surfaces for respectively supporting a plurality of screws of different lengths carried by the holder so as to facilitate proper identification of the plurality of screws. In one invention herein, a screw holder is provided with stepped surfaces for respectively supporting a plurality of screws of different lengths carried by the holder so as to facilitate proper identification of the plurality of screws and easy attachment of the screws to a screw insertion device.

The embodiments of the invention set forth below are examples of the invention, and may in some instances be broader than the foregoing embodiment of the invention but are not intended to limit the breadth of the foregoing embodiment or the breadth of the invention. Additional features of the invention set forth in such embodiments are optional. A feature of any embodiment set forth below can be combined with the foregoing embodiment, with or without any other feature of any embodiment set forth below. All characteristics, steps, parameters and features of any method, process, apparatus, device or system described below are not limited to any specific embodiments set forth below, but instead are equally applicable to the foregoing embodiment of the invention and to all embodiments of the invention. Broad terms and descriptors are replaced in some instances with more specific terms and descriptors, not to limit a disclosure to a specific term or descriptor but merely for ease of discussion and understanding.

The implant insertion device for use with the inventions herein can be of any suitable type. One suitable implant insertion device is described herein. Such apparatus or device is suitable for inserting an implant such as an intramedullary nail and related fasteners into or onto a bone of a mammalian body for treating fractures, nonunions or malunions of the bone. It may also be used for fusion across bones such as the femur-tibia and calcaneus-talus-tibia. The device can include a targeting assembly for continuous or dynamic adjustment of the angle of a guide or alignment sleeve, and the fastener carried thereby, relative to an aperture in the implant for receiving the fastener. Such apparatus or device can also be referred to as an implant insertion device, a dynamic targeting mechanism, a targeting guide, a nail targeting device, a jig, an outrigger and other similar or suitable names.

In any embodiment, apparatus or implant insertion device 21 illustrated in FIG. 1, which can be made of any suitable material such as stainless steel, titanium, alloys, plastics, carbon fibers, or any composite or mesh materials, is provided for use with a suitable implant or implantable device such as an intramedullary rod or nail 22, a suitable alignment or guide sleeve 23 and a suitable fastener such as a fixation bolt, trial implant, trial lag screw, lag or locking screw 24. Device 21 and guide sleeve 23 can be used to place trial lag screw or any screw 24 into the rod 22 once the rod 22 has been implanted into a bone of a mammalian body or before its implantation. Intramedullary rod 22 can include an aperture or hole 25 for receiving screw 24 and the rod 22 is configured to permit the screw 24 to pivot in aperture 25 relative to the rod 22. Device 21 can include a body 26 having a first or arm portion 27 and a second or targeting portion 28. In any embodiment, targeting portion 28 is elongate and linear, extends along a longitudinal axis 31 and can have a first or bottom portion 32 and a second or a top portion 33. The bottom portion 32 can be referred to as first end portion 32 and the top portion 33 can be referred to as a second end portion 33. Arm portion or arm 27 in any embodiment is arcuate so as to resemble an arch and can have a first end portion or first extremity 36 coupled or joined to top portion 33 of targeting portion 28 by any suitable mean and a second end portion, second extremity or connector 37 adapted for coupling to the top or proximal end portion of intramedullary rod 22. The arm 27 can be made from any suitable material such as stainless steel, carbon fiber, plastic or composite materials, and in any embodiment can include an arcuate member or top arch 38 which extends from first end portion 36 of the arm 27 and an elongate member or gooseneck 39 which extends from the upper end of top arch 38 to the connector 37. When insertion device 21 is coupled to rod 22, as illustrated in FIG. 1, targeting portion 28 is spaced from and generally extends parallel to rod 22. In any embodiment, the targeting portion 28 is spaced from rod 22 at least in the vicinity of aperture 25 of the rod 22.

The targeting portion 28 can include a targeting assembly or mechanism 46 for receiving guide sleeve 23 and in any embodiment for pivoting the guide sleeve relative to the targeting portion, rod 22 and aperture 25 in intramedullary rod 22 through an angular range. The mechanism 46 serves to point guide sleeve 23, fastener 24 and in any embodiment both the guide sleeve 23 and the fastener 24 towards the intramedullary rod and more specifically towards the aperture 25 in the rod. In any embodiment, the mechanism and hence the device 21 serves to point the guide sleeve 23, the fastener 24 or the combination of the guide sleeve and the fastener towards the rod and in any embodiment the aperture 25 in the rod throughout or continuously over such angular range. Any suitable apparatus, mechanism or assembly can be provided for so pivoting the guide sleeve, the fastener or the combination of the guide sleeve and fastener. In any embodiment, targeting assembly can include a first elongate element or rail 47 and a second elongate element or rail 48 extending along longitudinal axis 31 in spaced-apart positions (see FIG. 2). First and second rails 47, 48 extend parallel to each other and are spaced apart from each other. Each of the longitudinally-extending rails 47, 48 can resemble a planar strip or bar. Each can be made from any suitable material such as stainless steel, metal, composite materials, plastic, carbon fiber or other fibers. First rail 47 can have an inner planar surface 51, illustrated in FIG. 3, and second rail 48 can have an inner planar surface 52, illustrated in FIG. 4, which face each other and extend parallel to each other.

Figure 7:
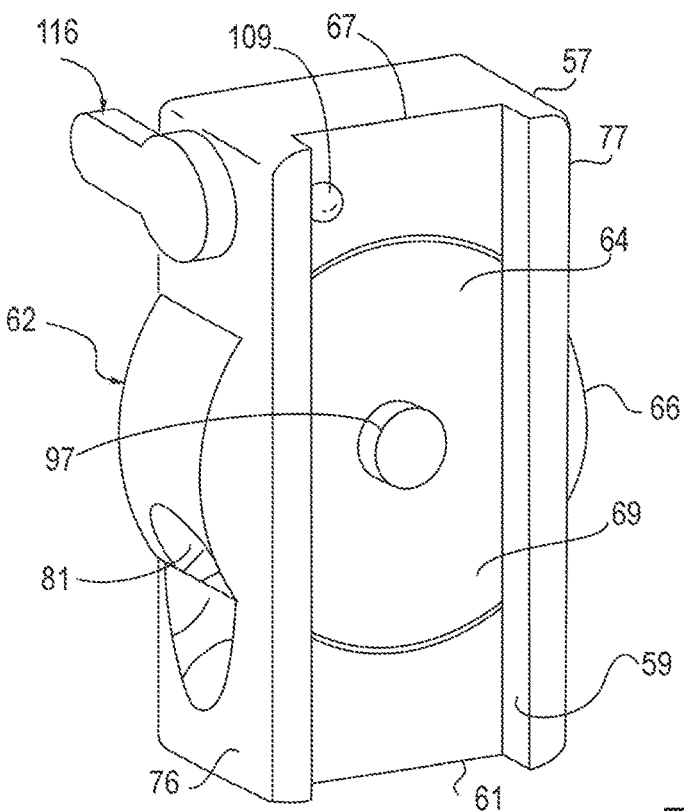
FIG. 7 is a first side perspective view of a portion of the continuously adjustable targeting assembly of the implant insertion device of FIG. 1 with a portion of the housing removed.

Targeting assembly 46 can include a carriage assembly or carriage 56 that can be slidably carried by first and second rails 47, 48. The carriage 56 can include a slide 57 made from any suitable material such as stainless steel and that is sized and shaped to more upwardly and downwardly along longitudinal axis 31 between rails 47 and 48. In any embodiment, shown for example in FIGS. 7 and 8, the slide 57 can include a planar first side surface 58 for slidably engaging inner elongate surface 51 of the first rail 47. Slide 57 further can include a cutout 59 for slidably receiving second rail 48 and assisting in the centering of slide 57 during its longitudinal travel along the rails 47 and 48. The planar second side surface 61 of the slide, which forms the base of cutout 59, extends parallel to first side surface 58 and slidably engages inner elongate surface 52 of the second rail 48.

A targeting element 62 can be rotatably carried by slide 57. In any embodiment, the targeting element 62 can be a disk, wheel or any other suitable shape having a first planar side surface 63 and an opposite second planar side surface 64 extending parallel to the first side surface 63. In any embodiment, a circumferential, circular surface 66 extends between side surfaces 63 and 64, which are spaced apart a distance substantially equal to the distant between first side surface 58 and second side surface 61 of the slide 57. It is appreciated that, depending on the shape of targeting element, surface 66 can be any other suitable shape including oval or semicircular. Slide 57 can include a recess 67 that is sized and shaped to rotatable receive disk 62 in a manner that the first and second side surfaces 63, 64 of the disk seat substantially flush with the respective first and second side surfaces 58, 61 of the slide 57. In this regard, recess 67 extends through side surfaces 58 and 61 and is formed in part by opposed first and second arcuate surfaces 68, 69 in slide 57, each having a radius substantially equal to the radius of disk 62. Slide 57 can have a front face 76 and a rear face 77, and disk 62 is diametrically sized relative to slide 57 such that circumferential surface 66 of the disk extends outwardly from the slide 57 and front face 76 and rear face 77 of the slide 57.

Disk 62 can have a bore, passageway, hole or aperture 81 extending therethrough for slidably receiving guide sleeve 23. In any embodiment, passageway 81 extends though the disk 62 to opposite first and second openings provided on circumferential surface 66 of the disk. In any embodiment, the passageway 81 extends along an axis 82 centered on a diameter of the disk 62. Aperture 81 can be referred to as angularly adjustable aperture.

Targeting portion 28 can include an apparatus for pivoting disk 62 relative to the targeting portion so as to permit the angle of passageway axis 82 relative to longitudinal axis 31 of the targeting portion to be continuously adjusted as carriage 56 is moved upwardly and downwardly along first and second rails 47, 48. In this manner, passageway axis 82 can be pointed towards the intramedullary rod and more specifically towards the aperture 25, which can be referred to as an angularly adjustable aperture, in the rod through the continuous range of angular adjustment of the fastener 24 relative to the rod 22. Apparatus 86 can include first and second rails 47, 48 and in any embodiment inner elongate surface 51 of the first rail 47 can include a first groove 87 formed therein and a second groove 88 formed therein (see FIGS. 3 and 5). The first and second grooves or cam grooves 87, 88 are inclined relative to each other and to longitudinal axis 31. In any embodiment, first cam groove or track 87 extends towards the center of the elongate surface 51 as it extends longitudinally upwardly along the rail 47 and second cam groove or track 88, which is lower on the elongate surface 51 relative to the first cam groove 87, similarly extends towards the center of the elongate surface 51 as it extends longitudinally upwardly on the first rail 47. First side surface 63 of the disk 62, which faces inner elongate surface 51 of the first rail 47, can have first and second spaced-apart protuberances 91, 92 extending outwardly therefrom. In any embodiment, first protuberance or cam pin 91 extends from surface 63 adjacent circumferential surface 66 and second protuberance or cam pin 92 extends from surface 63 adjacent circumferential surface 66 at the opposite end of a diameter of the disk 62 relative to first cam pin 91. As such, first and second cam pins 91, 93 are diametrically opposed on disk surface 63. The transverse dimensions or diameters of the cylindrical cam pins 91 and 92 approximates the widths of respective cam grooves 87 and 88, and first cam pin 91 slidably seats within first cam groove 87 and second cam pin 92 slidably seats within second cam groove 88 when slide 57 is slidably carried between the first and second rails 47, 48.

Apparatus 86 further can include a longitudinally-extending groove or guide slot 96 extending along inner elongate surface 52 of the second rail 48. An additional protuberance or guide pin 97 extends from the center of second side surface 64 of the disk 62 and seats within guide slot or pivot slot 96 for permitting rotation of disk 62 between first and second rails 47, 48. Cylindrical guide pin 97 can have a diameter approximating the width of guide slot 96, and the guide slot can have a length to permit rotation of the disk 62 throughout the longitudinal travel of carriage 56 along rails 47 and 48.

First and second rails 47, 48 and disk 62 have cooperatively engaging features for pivoting the targeting element or disk 62 relative to the first and second rails as the disk slides longitudinally along the first and second rails so as to permit the angle at which the fastener or screw 24 is inserted into the aperture 25 of the rod 22 to be continuously adjusted through an angular range, which can be referred to as a dynamic angular range. In any embodiment, such cooperatively engaging features can include the elongate surface 51 of the first rail 47 and the first groove 87 and the second groove 88 formed in elongate surface 51, and the first side surface 63 of the disk 62 and the first and second protuberances 91, 92 extending outwardly from the side surface of the targeting element or disk 62 for slidably seating in the respective grooves 87, 88. In any embodiment, such cooperatively engaging features can additionally include the elongate surface 52 of the second rail 48 and the groove or guide slot 96 extending along the elongate surface 52, and the second side surface 64 of the disk 62 and the protuberance or guide pin 97 that extends from the second side surface 64 of the disk 62 for slidably seating in the groove or slot 96.

Carriage 56 can include a first cover portion or cover 101 that extends over first rail 47 and secures on its opposite sides to the respective sides of first surface 58 of slide 57. Carriage 56 further can include a second cover portion or cover 102 that extends over second rail 48 and joins to the slide 57 over cutout 59. First and second covers 101, 102, which can each be made from any suitable material such as stainless steel, serve to respectively capture first and second rails 47, 48 within carriage 56 throughout the longitudinal travel of the carriage along rails 47 and 48.

When carriage 56, and disk 62 rotatably carried by slide 57, are slidably mounted on targeting portion 28, first surface 58 of the slide 57 and first side surface 63 of the disk 62 face and slidably engage inner elongate surface 51 of first rail 47, and second surface 61 of the slide 57 and second side surface 64 of the disk 62 face and slidably engage inner elongate surface 52 of the second rail 48. Guide pin 97 of the disk 62 is forcibly restrained on the center line of the inner elongate surface 52 of the second rail 48 throughout the longitudinal travel of the carriage 56 and permits disk 62 to rotate or pivot about an axis (not shown) extending orthogonal to and centered on inner elongate surfaces 51, 52 throughout the longitudinal travel of the carriage 56 on targeting portion 28.

Figure 17:
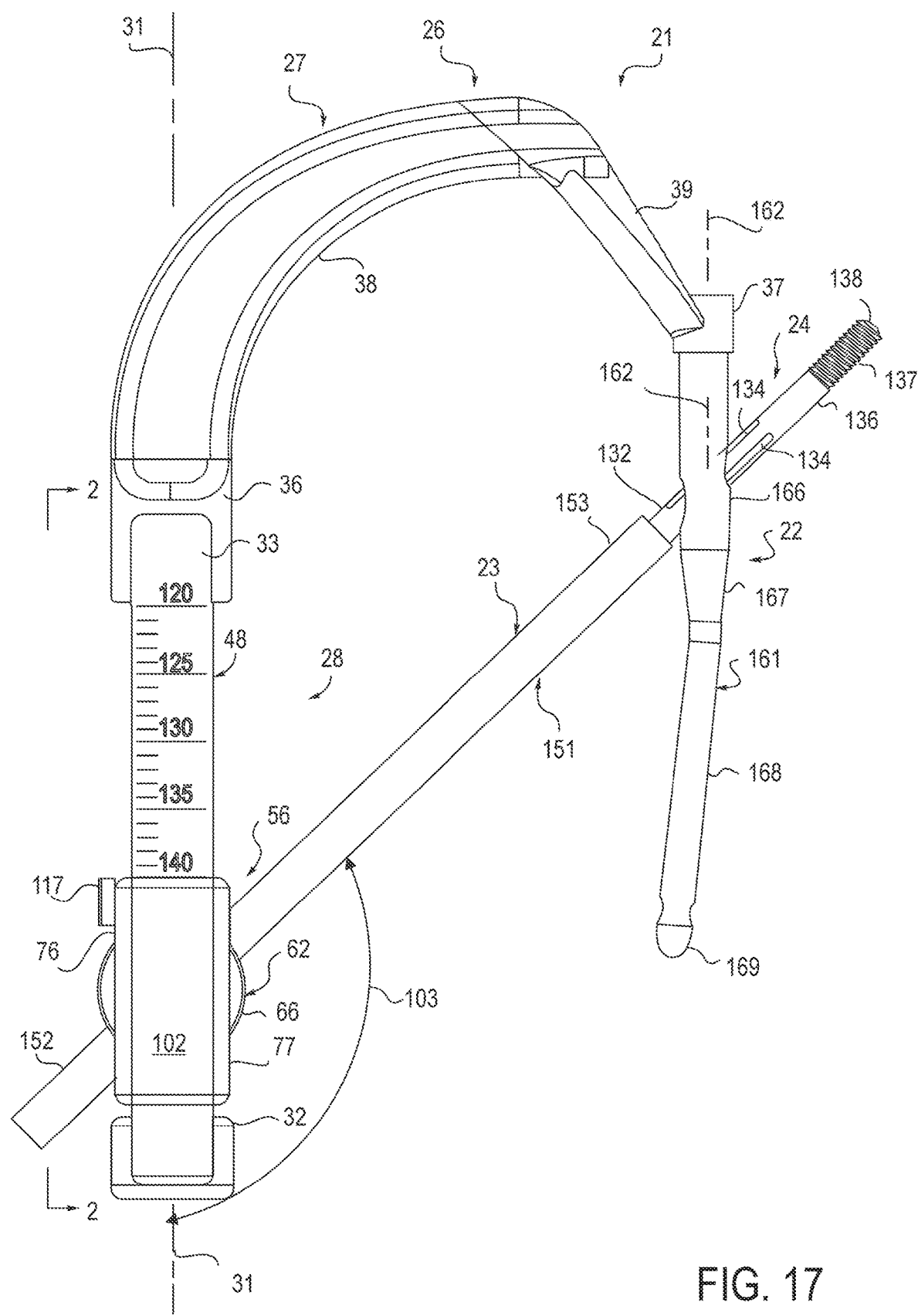
FIG. 17 is a side plan view of the implant insertion device of FIG. 1 with the continuously adjustable targeting assembly in a third position.

The capture of first and second cam pins 91, 92 within respective first and second inclined cam grooves 87, 88 urge the disk 62 to pivot or rotate relative to the rails 47 and 48 and targeting portion 28 as the carriage 56 travels longitudinally along the targeting portion. In any embodiment, the cooperative engagement of cam pins 91 and 92 and respective cam groves 87 and 88 causes disk 62, and passageway 81 extending therethrough, to rotate in a continuous and in any embodiment linear manner as the carriage 56 travels longitudinally from a first position on targeting portion 28 to a second position on the targeting portion. The angular range, which can also be referred to as the dynamic angular range, through which passageway 81 and passageway 81 pivot or rotate relative to the targeting portion can vary. In any embodiment such angular range is at least 5 degrees; in any embodiment such angular range is approximately 10 degrees; in any embodiment such angular range is approximately 20 degrees; in any embodiment such angular range is approximately 30 degrees; in any embodiment such angular range is approximately 40 degrees; in any embodiment such angular range is approximately 50 degrees; in any embodiment such angular range is approximately 60 degrees; in any embodiment such angular range is approximately 70 degrees; and in any embodiment such angular range is approximately 80 degrees. In any embodiment illustrated in the figures, disk 62 and passageway 81 extending therethrough pivot or rotate relative to first and second rails 47, 48 from an angle 103 of approximately 120 degrees when carriage 56 is in a first or upper position on targeting portion 28, as shown in FIG. 1, to an angle 103 of approximately 130 degrees when the carriage is in a second or intermediate position on the targeting portion 28, as shown in FIGS. 2-4, and then to an angle 103 of approximately 140 degrees when the carriage 56 is in a third or lower position on targeting portion 28, as shown in FIG. 17. In this embodiment, the longitudinal travel and carriage 56 and the angular rotation of disk 62 are one-to-one, that is linear.

It is appreciated that cam grooves 87 and 88 can be configured so that the pivoting of disk 62 and passageway axis 81 is non-linear as carriage 56 travels along targeting portion 28, or is non-continuous along a portion of such travel, that is the disk 62 pivots or rotates during some of its longitudinal travel but not at other parts of its longitudinal travel. It is further appreciated that any combination of linear, non-linear and non-continuous rotation or pivoting of disk 62 can be provided by appropriately configuring the shape of first and second cam grooves 87, 88 on respective inner elongate surfaces 51, 52, or by any other suitable means.

As shown in FIGS. 1 and 17, suitable indicators which can include numbers, lines, markings or combinations of numbers, lines and markings can be provided on the outside of at least one of rails 47 and 48 for indicating the angle of passageway 81 and passageway axis 82 at some or all of the positions of carriage 56 on the rails 47 and 48 and targeting portion 28. As can be appreciated, the angle of the passageway 81 is the same as the angle of the guide sleeve 23 and the fixation screw 24 mounted on the end of the guide sleeve 23 relative to the targeting portion 28.

Figure 8:
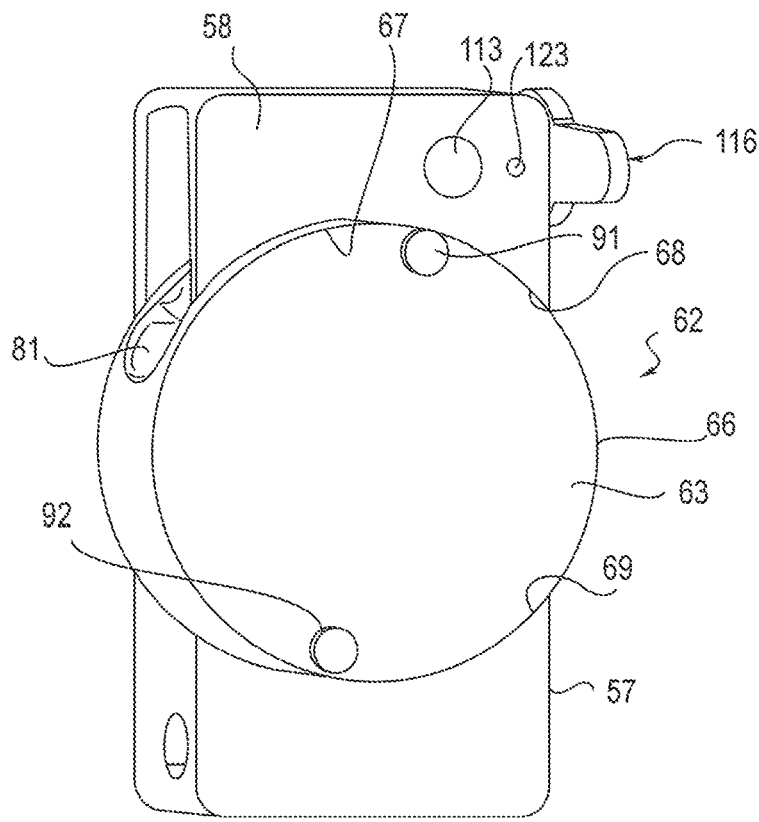
FIG. 8 is a second side perspective view of a portion of the continuously adjustable targeting assembly of the implant insertion device of FIG. 1 with a portion of the housing removed.
Figure 10:
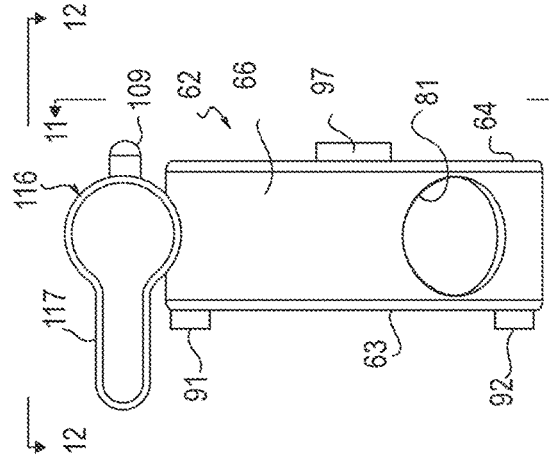
FIG. 10 is a front view of the portion of the continuously adjustable targeting assembly of FIG. 9 taken along the line 10-10 of FIG. 9.

A mechanism or assembly can be included in implant insertion device 22 for locking carriage 56 on certain or any positions along targeting portion 28. In any embodiment, a detent pin 106 having a stem 107 extending from an enlarged head 108 and having a rounded end 109 is provided in slide 57 such that the rounded end 109 retractably extends outwardly from second surface 61 of the slide 57 (see FIG. 7). The rounded end 109 of the detent pin 106 selectively seats with one of a plurality of longitudinally spaced-apart detent holes 111 provided in inner elongate surface 52 of the second rail 48 (see FIG. 4). Any suitable spacing can be provided between detent holes 111, so as to permit locking the disk 62 and passageway 81 at any suitable angular interval. The detent pin 106 is urged to its extended position, in which rounded end 109 extends outwardly from second surface 61 of the slide 57 into one of holes 111, by means of a spring 112 disposed in slide 57 between head 108 of the pin and a plug 113. Pin 106, spring 112 and plug 113 are each disposed within a bore (not shown) extending from first surface 58 to second surface 61 of the slide 57. Plug 113 is secured within such bore and seats flush with first surface 58, as illustrated in FIG. 8.

Figure 12:
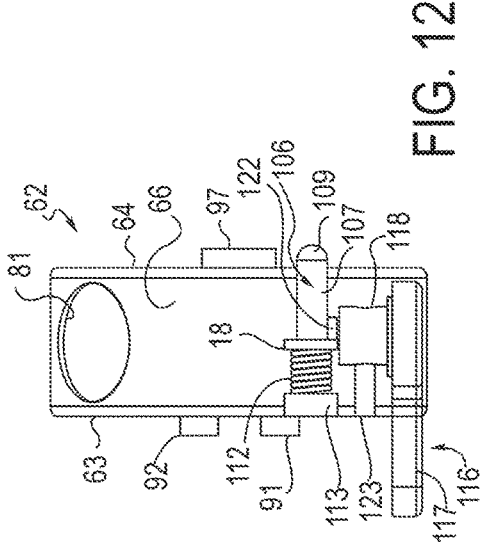
FIG. 12 is a top view of the portion of the continuously adjustable targeting assembly of FIG. 9 taken along the line 12-12 of FIG. 10.
Figure 9:
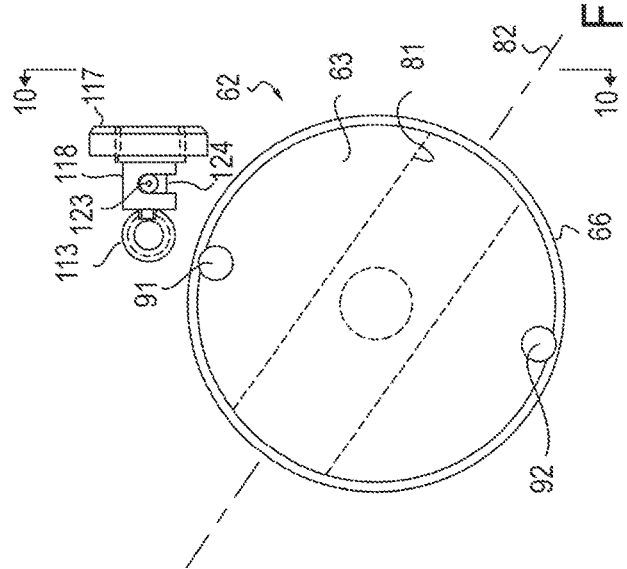
FIG. 9 is a first side view of a portion of the continuously adjustable targeting assembly of the implant insertion device of FIG. 1 with the housing removed.
Figure 11:
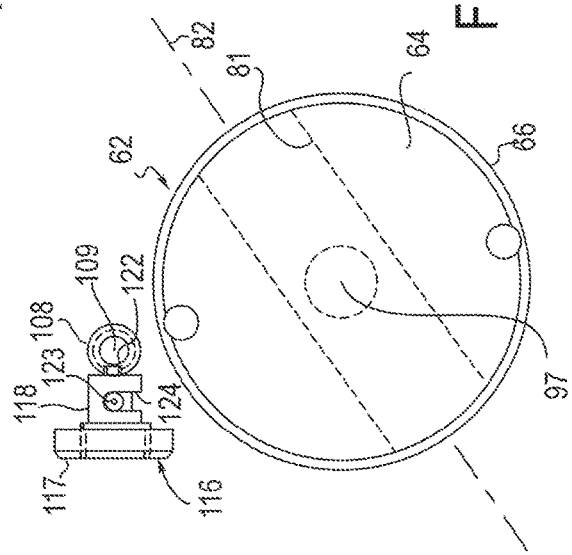
FIG. 11 is a second side view of the portion of the continuously adjustable targeting assembly of FIG. 9 taken along the line 11-11 of FIG. 10.

A locking or other suitable element 116 is provided in carriage 56 for urging or moving rounded end 109 of the detent pin 106 against the force of spring 112 from its first or extended position, in which the rounded end extends outwardly from second surface 61 of the slide 57, to its second or retracted position, in which the rounded end is seated flush with or recessed within the second surface 61. In any embodiment, locking element 116 can have a lever 117 accessible at front face 76 of the slide 57 and a cylindrical stem 118 which extends into a bore 119 provided in front face 76 of the slide 57. An off-centered pin 122 extends distally from one side of the end of stem 118 and engages the underside of head 108 of the pin 106 (see FIG. 12). As lever 117 is rotated clockwise relative to front face 76 though an angle of approximately 180 degrees, the off-centered pin 122 causes the detent pin 106 to retract within slide 57. A cylindrical pin or rotation limiter 123 extends from first surface 58 of the slide 57 through a bore (not shown) in the slide 57 to engage a semi-annular recess 124 provided in stem 118 of the locking element 116. The engagement of rotation limiter 123 with the end surfaces of the recess 124 limits the rotational travel of the locking element 116 and lever 117 thereof to its desired 180 degrees of angular travel. The rotation limiter 123 further serves to retain stem 118 of the locking element 116 within slide 57, so as to secure the locking element to the slide.

Fastener or screw 24 for use with implant insertion device 21 and intramedullary rod 22 can be of any suitable type and in any embodiment is made from an elongate cylindrical body 131 or spiral blade (not shown) having a length ranging from 40 to 200 millimeters and a diameter ranging from two to 20 millimeters. In any embodiment, the fastener is a fixation screw formed from a body having a threaded portion and a smooth portion. The elongate body 131 can be formed from any suitable material such as stainless steel and include a proximal portion 132 having any outer cylindrical or irregular-shaped surface 133. The proximal portion 132 may be provided with a plurality and as shown four longitudinally-extending slots 134 extending through the surface 133 in circumferentially-spaced apart positions. Distal portion 136 of the body 131 may be provided with external threads 137 that extend to a sharpened distal end or tip 138 of the body. Alternatively, the distal portion 136 of the body 131 may be irregularly shaped or flat (not shown). The body can be provided with a central bore 142 that extends longitudinally through the body 131 from the proximal portion 132 to the distal end or tip 138. The proximal end of the central bore 142 may be provided with internal threads 143 and be formed with a drive socket 144 of any suitable type for facilitating connection of the proximal fixation screw to a drive tool of any suitable type. The proximal end of the body 131 can be formed with a suitable flanged head 146 that has a transverse dimension that is slightly larger than the transverse dimension of the remainder of the body 131 and, as such, limit the longitudinal travel of screw 24 within aperture 25 of the intramedullary rod 22 during operation and use of rod 22 and screw 24 within a suitable bone of a mammalian body.

Guide or alignment sleeve 23 can be of any suitable type and in any embodiment is formed from a cylindrical member or body 151 made from any suitable material such as stainless steel. Body 151 of guide sleeve or overtube 23 can have a proximal portion 152 and a distal portion 153. At least proximal portion 152 can have a circular cross section and in any embodiment the entire length of the body 151 is circular in cross section. Passageway 81 of disk 62 can have a diameter that approximates and is at least slightly larger than the cross-sectional dimension of body 151 and as such approximates and is at least slightly larger than the diameter of any circular cross section of the body 151. Body 151 can be provided with a central bore 154 extending therethrough so as to be tubular in conformation. The distal end of body 151 can include a suitable drive portion or element (not shown), for example a threaded extension for cooperatively connecting with internal threads 143 provided at the proximal end of screw 24 so as to permit the screw 24 to be connected to the distal end of the guide sleeve 23 and permit the screw 24 to be rotated or driven by the guide sleeve during placement of the screw 24 within a bone.

One embodiment of an implantable medical device suitable for use with implantable insertion device 21 discussed above is apparatus or device or intramedullary rod 22 illustrated in FIGS. 13-16. Although rod 22 can be used in any bone of a mammalian body, in any embodiment rod 22 is for use in a femur and may thus be called a femoral nail 22. Nail 22, described in U.S. Pat. No. 9,220,554 entitled Implantable Device with Locking Adjustment Mechanism and Method for Using Same that issued on Dec. 29, 2015, the entire content of which is incorporated herein by this reference, can include an elongate body 161 that extends along a longitudinal or central axis 162 and can have a proximal portion or proximal end or head 166, a central portion or neck 167 and a distal portion or shaft 168 that terminates at a distal tip 169. The nail 22 is illustrated schematically in the figures, where head 166, neck 167 and shaft 168 are not necessary drawn to scale. Body 161 may curve in at least one portion of shaft or stem 168 to align the rod 22 along the length of the marrow canal of the femur or other bone in which the rod is to be inserted. Elongate body 161 can be provided with a longitudinally-extending passageway or bore 176 for permitting the rod to slide along a guide wire (not shown) during insertion of the rod into the femur or other bone of the mammalian body. Furthermore at least one bore 177 can be provided in the distal end portion of stem 168 adjacent tapered tip 169 for receiving at least one distal fastener or screw (not shown).

Figure 16:
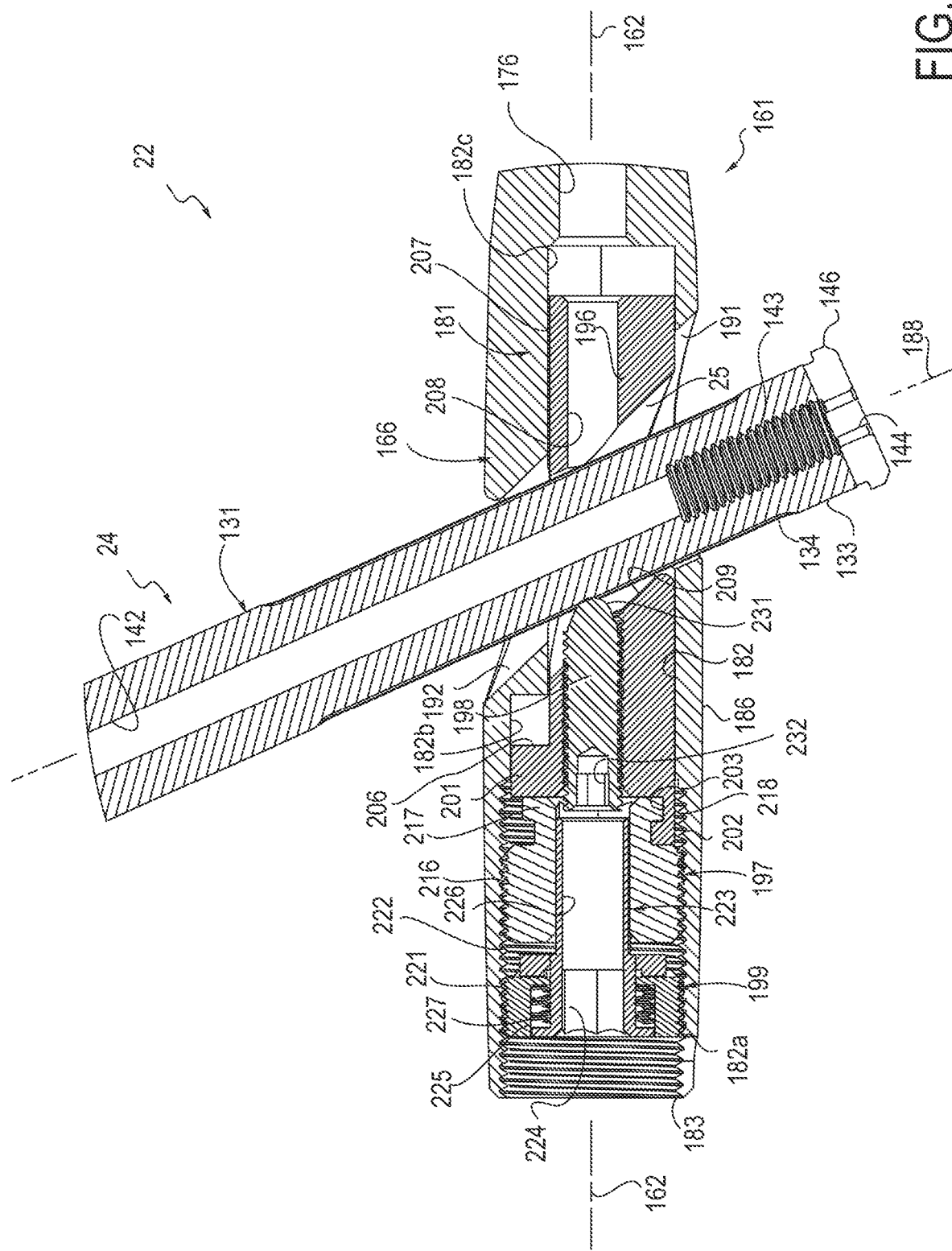
FIG. 16 is an enlarged cross-sectional view of the intramedullary rod with a pivotable fastener of FIG. 13 taken along the line 16-16 of FIG. 15.

Head 166 of rod 22 may include an actuation or adjustment mechanism or assembly 181 for selectively pivoting proximal fixation screw 24 from a first angled position relative to the nail head 166 to a second angled position relative to the nail head. In this regard and as illustrated in FIG. 16, the proximal portion central passageway 176 of the nail 22 can be hallowed to form a longitudinally-extending proximal recess 182 that communications with proximal opening 183 in the proximal end of the head 166. Proximal recess 182 can have a proximal or internally-threaded portion 182a adjacent proximal opening 183, a circular central portion 182b and a distal portion 182c that in any embodiment is noncircular in cross section and sometimes referred to herein as the segmented circular portion or segmented portion 182c. Tubular head 166 is formed by an outer wall 186, which is substantially annular in shape and formed by the proximal recess 182. Head 166 of rod 22 can include a suitable feature for registering the rod 22 with an implant insertion device, such as targeting device 21, or any other suitable device. For example, such feature can inhibit rotation of the rod 22 with such other device after the rod is secured to such device. In any embodiment, at least one slot may be provided on the proximal end of head 166 at proximal opening 183 for registering with a cooperating feature on the end of the implant insertion device or other device to which the rod is being connected.

Head 166 is provided with at least one passageway, bore, hole or aperture 25 extending along a transverse axis 188 inclined at an angle to longitudinal axis 162. Head 166 is adapted to receive fastener or screw 24 in aperture 25, which is distinct from proximal recess 182 of elongate passageway 176 but formed in part by the proximal recess 182. In any embodiment, head 166 is provided with a single aperture 25. The aperture 25 can formed by a first or lateral transverse opening 191 provided on one side of wall 186 and a second or medial transverse opening 192 provided on the other side of the wall 186. Transverse axis 188 is centered on aperture 25 and can extend relative to longitudinal axis 162 at an angle and in any embodiment at an angle of approximately 140 degrees measured from the portion of head 166 distal of head aperture 25.

Although the actuation or adjustment mechanism 181 for pivoting the proximal fixation screw 24 can be of any suitable type, in any embodiment mechanism 181 can include an insert, element or sleeve 196, a threaded element or control element 197, an alignment or set screw 198 and a locking mechanism 199. Unless otherwise indicated, each of these components can be made any suitable material such as stainless steel.

Sleeve 196, which in any embodiment is one example of the broad categories of elongate elements or movable elements, can be formed from an elongate tubular element or member having at its proximal portion or end portion a circular annulus or ring 201. A lip 202 is spaced proximally from annulus 201 by a recess 203. Annulus 201 forms the periphery of the sleeve 196 and is substantially circular in shape. Sleeve 196 is provided with an elongate cutout 206 extending distally of annulus 201 for forming distal portion 207 of the sleeve 196. In any embodiment, the distal portion 207 is noncircular in cross section and in any embodiment can have a cross section that corresponds generally with the cross section of segmented portion 182c of the head proximal recess 182. Distal portion 207 of the sleeve 196 is sized and shaped to slidably move longitudinally within segmented circular portion 182c of the proximal recess 182 of the head 166. Annulus 201 of the sleeve of 196 is externally sized and shaped to slidably move longitudinally move within central portion 182b of the head proximal recess 182. A passageway or bore 208 extends the length of the sleeve 196. In any embodiment, bore 208 is internally threaded at its proximal portion. Sleeve 196 is provided with at least one aperture 209 in its distal portion 207 that is adapted to receive fastener or fixation screw 24. Aperture 209 is distinct from bore 208, and the bore 208 extends through the aperture 209. In any embodiment, sleeve 196 is provided with a single aperture 209.

Rotatable control element 197, which in any embodiment is one example of the broad categories of elements which include control elements, movable elements and threaded elements, is carried by head 166 and accessible at proximal opening 183 for causing the adjustment mechanism 181 to pivot fixation screw 24 relative to the head 166. The control element can be of any suitable type and in any embodiment can include a spindle, screw or worm gear 197 having first or proximal portion 216 that can be annular and externally threaded for threadable engagement with threaded portion 182a of proximal recess 182 of the head 166. The distal portion or end portion of the worm gear 197 can include an annular flange 217 spaced from externally-threaded proximal portion 216 by an annular recess 215. The flange 217 is diametrically sized and shaped to snugly seat within recess 203 of the sleeve 196. Similarly, annular recess 215 of worm gear 197 is diametrically sized and shaped to snugly receive lip 202 of the sleeve 196. When worm gear 197 is coupled or connected to sleeve 196 in this manner, the central axis of the worm gear is coincident with the central axis of the sleeve 196 and the worm gear is longitudinally fixed or locked relative to the sleeve 196, but the worm gear 197 is rotatable about such central axes and longitudinal axis 162 relative to the sleeve 196.

The worm gear 197 controls the longitudinal position and movement of sleeve 196 when such elements are disposed within head 166, and in this regard the worm gear can be provided with a central passageway or drive socket 218 that extends longitudinally through the worm gear and can have a noncircular cross section of any suitable type or shape. When sleeve 196 and worm gear 197 are so disposed within nail head 166, a suitable drive element seated within drive socket 218 of the worm gear 197 can serve to screw or rotate the worm gear 197 proximally or distally within the internally-threaded portion 182a of head proximal recess 182. Such advancement or withdrawal of the worm gear 197 within head 166 simultaneously causes sleeve 196 to advance or withdraw, in a one-to-one manner with the longitudinal movement of the worm gear 197, in central portion 182b and segmented portion 182c of the head proximal recess 182.

Locking mechanism, assembly or device 199 is coupled to worm gear 197 and configured to preclude rotation of the worm gear relative to head 166 when the locking mechanism is in a first position, shown in FIG. 16, and permit rotation of the worm gear 197 relative to the head 166 when the locking mechanism is in a second position (not shown). Although it is appreciated that locking mechanism 199 can have any suitable configuration and construction for rotatably locking and unlocking worm gear 197 within head 166, in any embodiment the locking mechanism can include a first locking element 221 and a second locking element 222. The second locking element 222 is moveable longitudinally between a first position in which a plurality of circumferentially spaced-apart protuberances or dogs 222a on its proximal surface cooperatively engage a plurality of circumferentially spaced-apart protuberances or dogs 221a on the distal surface of the second locking element 222 so that the second locking element is rotatably locked with the first locking element and a second position in which the plurality of circumferentially spaced-apart dogs of the second locking element 222 are disengaged from the plurality of circumferentially spaced-apart dogs the first locking element 221 so that the second locking element is rotatable relative to the first locking element. In any embodiment, the first locking element can be annular in shape and can be an annular element or nut that can be externally treaded and diametrically sized so as to threadably engage threaded portion 182a of proximal recess 182 in head 166. In any embodiment, the second locking element 222 can be annular in shape and can be an annular element or washer.

Locking mechanism 199 can further include a driver element or driver 223 having a drive socket 224 that extends longitudinally inwardly from its proximal end. Socket 224 can have a cross section which is non-circular in shape so that when the socket 224 is engaged by a suitable tool it can serve to cause rotation of the driver 223. A longitudinally-extending bore 226 extends distally from drive socket 224 through the remainder of the driver 223. The driver 223 extends through nut 221 and washer 222 and the washer 222 is secured to the proximal portion of the driver 223 by any suitable means such as welding. Nut 221 is not secured to driver 223 and thus longitudinally moveable relative to the driver. Means is included with locking mechanism 199 for urging washer 222 towards its first or locking position relative to nut 221, and can include a suitable spring, for example an annular wave spring 227 disposed around driver 223 and engaging a first flange 225 provided at the proximal end of the driver 223 and a second flange provided on the distal end of the nut 221. Spring 227 urges locking mechanism 199 towards its first or rest position, illustrated in FIG. 16, in which washer 222 is rotatably locked relative to the nut 221.

When driver 223 is urged longitudinally in a distal direction, for example by insertion of a suitable drive tool in drive socket 224 of the driver 223 and exertion of a longitudinal force in the distal direction on the tool and thus the driver 223, washer 222 that is rigidly secured to the proximal portion of the driver 223 is moved longitudinally against the force of spring 227 away from nut 221 so that the dogs of the washer 222 separate and disengage from the dogs of the nut 221 so that the combined driver 223 and washer 222 unit can be rotated relative to nut 221.

Set screw 198 can be of any suitable type and in any embodiment is cylindrical in conformation and externally threaded. The set screw 198 can include a rounded distal end 231 and a suitable drive socket 232 provided at its proximal end. Such set screw is diametrically sized so as to be capable of being passed longitudinally through drive socket 224 and bore 226 of drive 223 and into bore 208 of the sleeve 196 to threadably engage the threaded proximal portion of the sleeve bore 208.

In operation and use, implant insertion device 21 can be utilized for placing nail 22 within a bone in any suitable manner and for example as discussed above. In one suitable method, end portion or connector 37 of the device is coupled to head 166 of the nail in any suitable manner for inserting the nail 22 into a bone of a mammalian body. In one method, a guide wire is first introduced into the bone and the nail is then threaded over the proximal end of the guide wire for proper placement and positioning in the bone. In this regard, the proximal end of the guide wire can be inserted through passageway 176 of the elongate body 161, though adjustment mechanism 181 by means of bore 208 of sleeve 196 and drive socket 218 of worm gear 197, and through locking mechanism 199 by means of bore 226 and drive socket 224 of driver 223. After the nail 22 has been properly positioned within the bone, the guide wire is removed from the nail 22 through proximal opening 183.

A suitable fastener such fixation screw 24 can be introduced through head 166 by means of lateral transverse opening 191, aperture 209 of sleeve 196 and medial transverse opening 192 and properly positioned within the bone. In this regard, fixation screw 24 is inserted through the distal end of guide sleeve 23 in a suitable manner, for example as discussed above, and in any embodiment the screw 24 extends from the distal end of the guide sleeve 23 so as to be mounted on the distal end of the guide sleeve 23. In any embodiment, the screw extends coaxially with the guide sleeve 23. The guide sleeve 23, before inserting of the screw 24 through the sleeve 23, is introduced through passageway 81 of disk 62. Further advancement of the guide sleeve 23 through the disk passageway 81 targets the distal tip 169 of the screw 24 into the aperture 25 in the head 166 of the nail 22. Regardless of the position of carriage 56 on rails 47 and 48, the guide sleeve 23 and fixation screw 24 are aligned and directed at aperture 25 of the nail 22. In this regard, targeting assembly 46 is configured to rotate disk 62 and guide sleeve 23 carried there the disk relative to the targeting portion 28 of device 21 and to simultaneously move the guide sleeve 23 longitudinally relative to the targeting portion 28 as the guide sleeve is pivoted relative to aperture 25 of the intramedullary nail 22.

Once the fixation screw 24, with the assistance of guide sleeve 23, has been introduced through aperture 25 of the nail 22, and either partially or fully placed within the bone of the mammalian body, the fixation screw 24 can be pivoted relative to head 166 and central axis 162 of the nail through a range of angles by means of adjustment mechanism 181 in the nail 22. In this regard, control element or worm gear 197 can be accessed through connector 37 of implant insertion device 21 and proximal opening 183 at the proximal end of head 166, for example by insertion of a suitable drive tool (not shown) through connector 37 and through opening 183 and then into proximal recess 182 and drive socket 224 of nut 221. In order to rotatably unlock locking mechanism 199 and worm gear 197 that rotates one-to-one with driver 223 of the locking mechanism, so as to permit longitudinal movement of sleeve 197 within head 166, the drive tool is urged distally in drive socket 224 relative to head 166 so as to cause the driver 223 to move longitudinally along axis 162 and thus cause the locking dogs on the washer 222 to longitudinally separate and disengage from the locking dogs of the nut 221 in the manner discussed above. Once the combined driver 223 and washer 222 unit have been moved to a second position of locking mechanism 199, the drive tool can be used to rotate driver 223 freely of nut 221 and head 166 so as to rotate worm gear 197 and thus cause the worm gear and sleeve 196 coupled to the worm gear to move longitudinally within recess 182. In this regard, since the portion of the fixation screw 24 extending through aperture 209 is constrained by sleeve 196, longitudinal movement of the sleeve relative to head 166 causes the fixation screw to pivot about medial transverse opening 192 of the head 166. In this manner, the actuation assembly 181 serves to change the transverse axis 188 of nail aperture 25.

Figure 18:
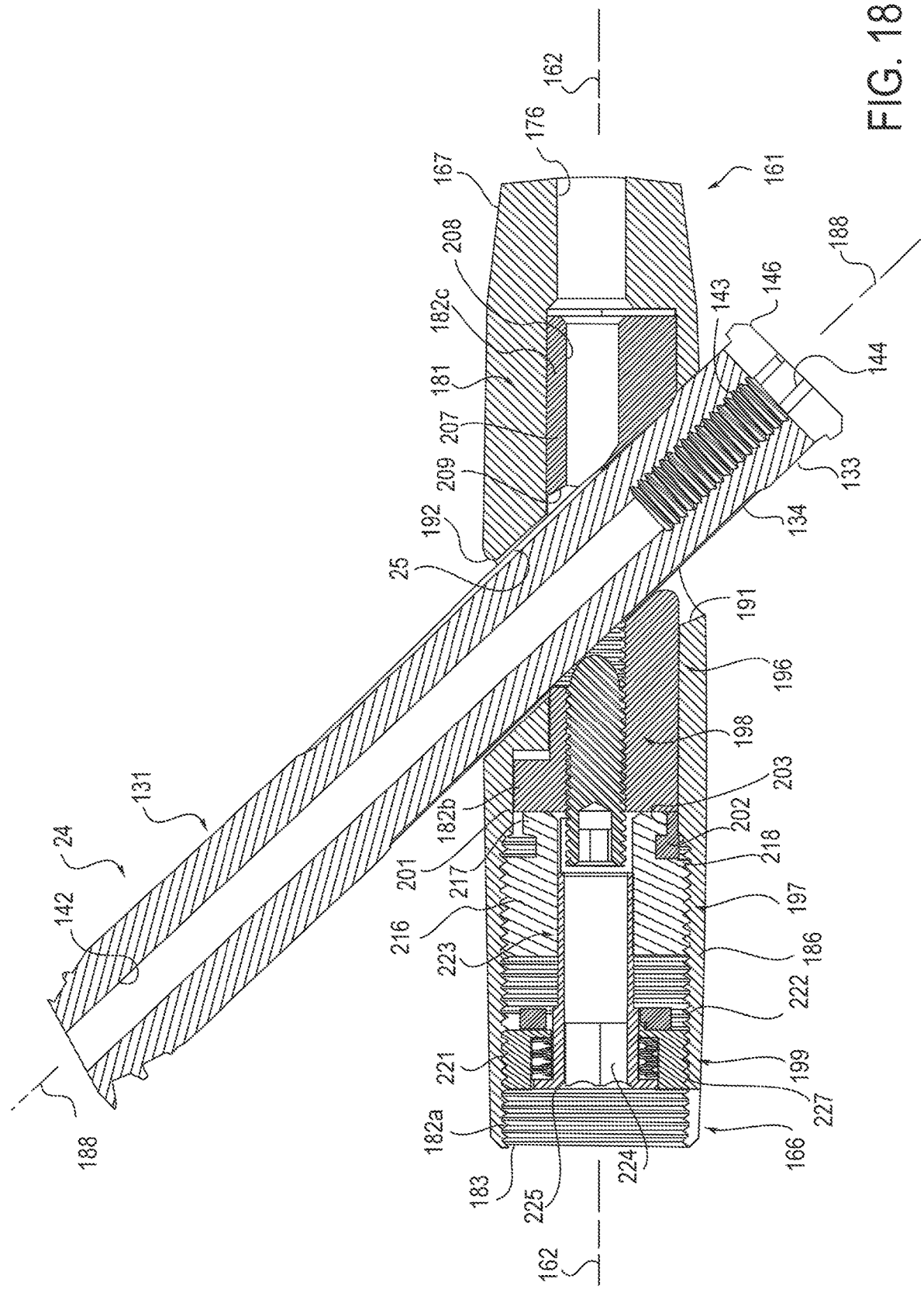
FIG. 18 is an enlarged cross-sectional view, similar to FIG. 16, of the intramedullary rod of FIG. 13 with the pivotable fastener in a second position as shown in FIG. 17.

In any embodiment, fixation screw 24 can be pivoted from a first or first extreme position, for example at an angle of approximately 120 degrees relative to head 166 of the nail 22 as shown in FIGS. 13-16, to a second or second extreme position, for example at an angle of 140 degrees relative to head as shown in FIG. 18. In any embodiment, targeting assembly 46 causes disk 62 and passageway 81 extending through the disk to pivot or rotate through the same angular range that fixation screw 24 can be pivoted relative to the intramedullary nail 22. The position of carriage 56 can be moved on rails 47 and 48 during or commensurate with the adjustment of the angular position of the screw 24 within head 24 so that the guide sleeve 23 remains supported by the device 21 and similarly angled as the fixation screw 24 during the procedure.

Once the fixation screw 24 has been desirable angled relative to nail 22, set screw 198 can be inserted through the driver 223 into the internally threaded proximal portion 208a of sleeve bore 208 and advanced distally until the rounded end 231 of the set screw engages the fixation screw 24 to lock the fixation screw in its desired angled position and inhibit further pivoting or rotation of the screw 24 within apertures 25 and 209. In any embodiment, rounded end 231 of the set screw 198 seats within one of the longitudinal slots 204 of the fixation screw 24 for enhancing the rotatable locking of the screw 24 within nail head 166.

The pivoting of the disk 62 relative to the targeting portion 28 when the guide sleeve 23 is disposed in the passageway 81 of the disk permits the angle at which the fixation screw is inserted into the nail aperture 25 to be continuously adjusted through an angular range. As a result, the guide sleeve 23 need not be withdrawn from the targeting portion 28 as with some currently provided implant insertion devices, or a second implant insertion device having a different static angle for the guide sleeve 23 coupled to the nail 22 as with other implant insertion systems, to change the angle at which the guide sleeve 23 and fixation screw 24 are directed at the nail head 166 and the aperture 25 in the head 166.

Figure 19:
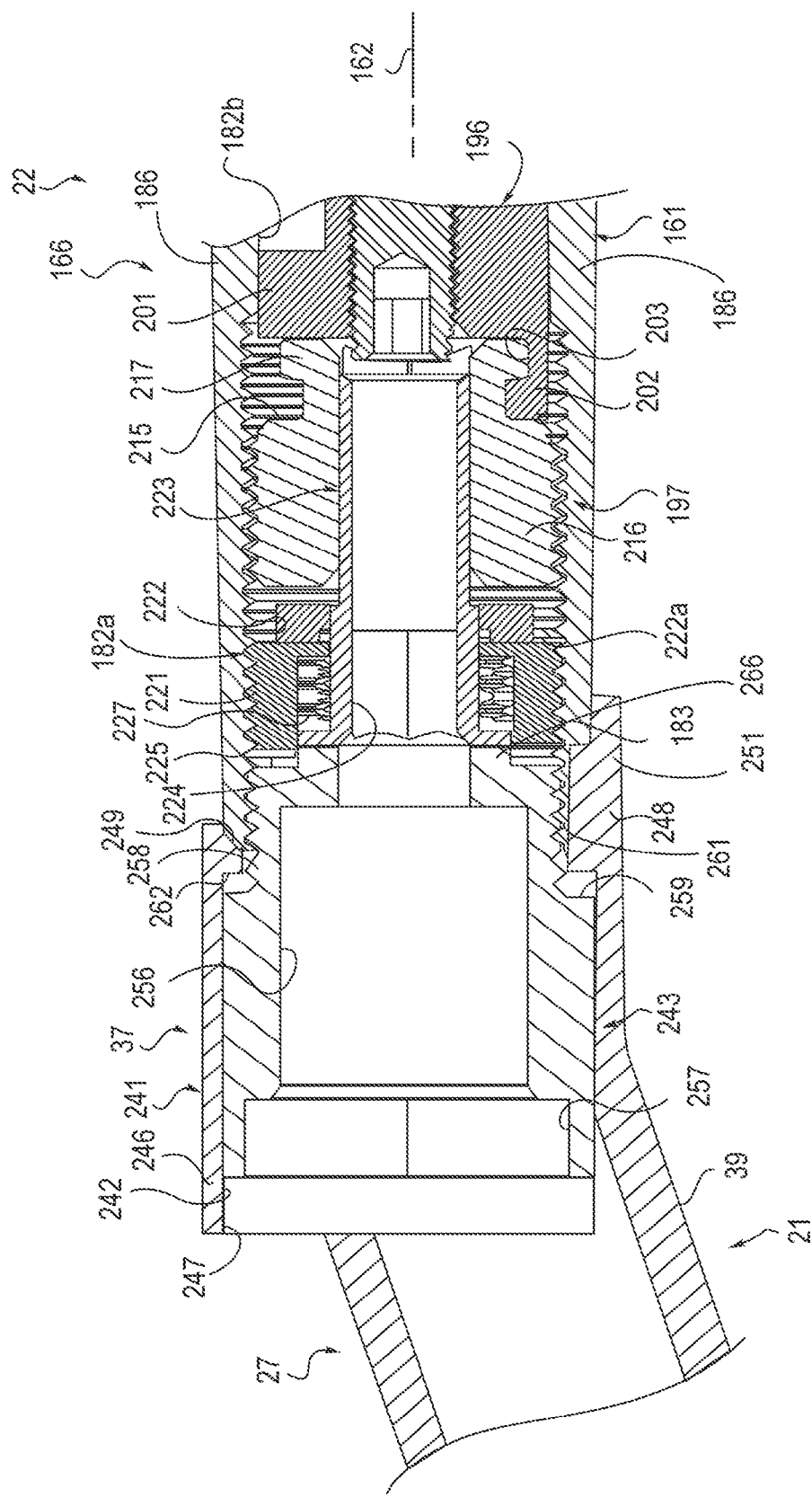
FIG. 19 is an enlarged cross-sectional view of a portion of the implant insertion device of FIG. 1 coupled to the intramedullary rod of FIG. 13 with the locking mechanism of the intramedullary rod in a first position.
Figure 20:
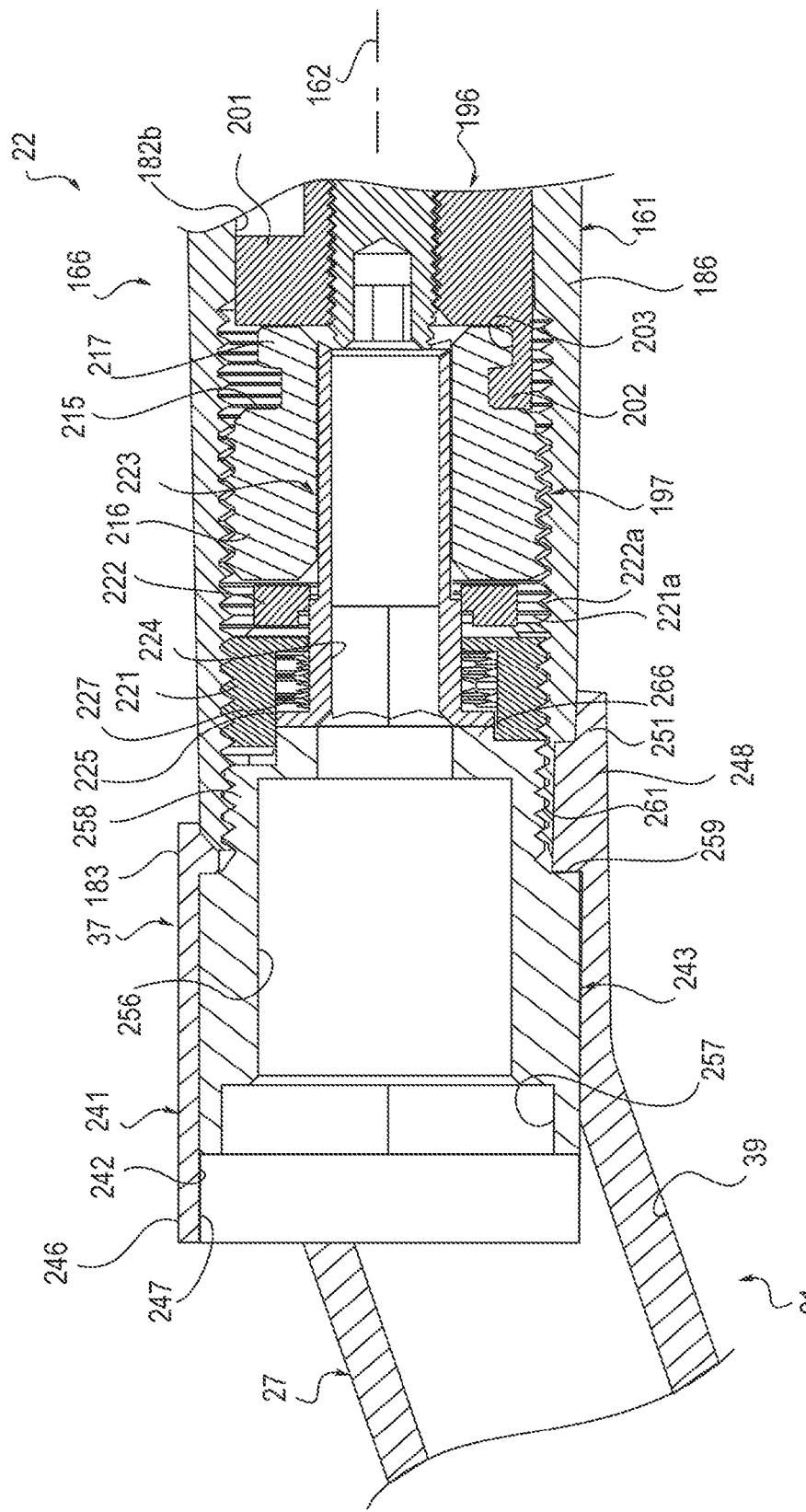
FIG. 20 is a cross-sectional view, similar to FIG. 19, with the locking mechanism of the intramedullary rod in a second position.

One embodiment of the connector 37 of targeting device or jig 21 suitable for coupling to a suitable implantable device such as nail 22 is illustrated in FIGS. 19 and 20. Targeting device or jig 21 illustrated therein can include distal portion or arm 27 having goose neck 39 at the distal extremity of the arm 27 and connector 17 at the distal end of the arm 27. In any embodiment, arm 27 terminates at connector 17, which can include a cylindrical or tubular housing 241 provided with a bore or socket 242 for receiving a connector element or fastening element 243, which can also be referred to as a threaded element or bolt. Housing 241 can have a proximal or upper end 246 provided with a proximal or upper opening 247 to socket 242 for permitting the fastening element 243 to be inserted into the socket and a distal or lower end 248 provided with a distal or lower opening 249 through which a portion of the fastening element 243 can extend for securing to the nail head 166.

Lower end 248 of the housing 242 is sized and shaped to cooperatively engage with the proximal end and proximal opening 183 of nail head 166. In any embodiment, the lower opening 249 can have a diameter approximating the diameter of the proximal opening 183 of nail head 166. Housing 241 can be further provided with a registering element or key 251 which is cooperatively sized and shaped to snugly seat within a recess or notch 252 provided on the proximal end of the nail head 166 so as to rotatably lock and register the housing 241 and thus targeting device 21 with the nail head 166 and thus nail 22.

Fastening or threaded element 243 can be of any suitable type and in any embodiment is a bolt having a first or proximal end provided with a drive recess or socket and an opposite second or distal end that is externally threaded. In any embodiment, a cylindrical nut or bolt 243 is provided and can have a diameter closely approximating but slightly smaller than the diameter of bore or socket 242 in housing 241. Bolt 243 can be provided with a through hole 256 extending through the bolt 243. A suitable drive socket 257 can be provided at the proximal end of the hole 256 for receiving any suitable drive element (not shown) for rotating the bolt 243 within housing 241. The exterior of the distal end 258 of bolt 243 necks down to a smaller diameter at annular surface 259 and is provided with external threads 261. The externally-threaded distal end 258 cooperatively engages and threads with internally-threaded portion 182 at the proximal end of nail head 166. Housing 241 is provided with an annular seat or surface 262 in socket 242 for receiving and engaging the annular surface 259 of the bolt 243.

When securing targeting assembly or device 21 to nail 22, bolt 243 is placed in socket 242 of housing 241 and the housing urged again the proximal end of nail head 166 so that housing key 251 registers with notch 252 in the nail head 166. A suitable drive tool is inserted into drive socket 257 of the bolt 243 to screw the external threads 261 of the bolt 243 into the proximal opening 183 of the nail head 166. The housing 241 is urged against and secured to the proximal end of the nail head 166 by the engagement of annular surface 259 of the bolt 243 with annular seat 262 of the housing 241.

The securing of the connector 17 of the targeting device 21 to the head 166 of the nail 22 automatically causes locking mechanism 199 of the nail to unlock so as to permit rotation of worm gear 197 and thus movement of sleeve 196 so as to thus permit pivoting of screw 24 relative to the nail 22. In any embodiment, the distal end 258 of bolt 243 can have a suitable actuation element of any suitable type such as an extension or cylindrical extension 266 which protrudes or extends distally from such end 258 and in any embodiment is centered on the central longitudinal axis of the bolt 243, which axis in FIGS. 19 and 20 is collinear with or the same as longitudinal axis 162. The extension 266 can have an external diameter less than the external diameter of the externally-threaded distal end 258. The external diameter of the extension 266 can be less than the internal diameter of nut 221 of the locking mechanism 199 so as to engage flange 225 of driver 223 of the locking mechanism and simultaneously move the driver 223 distally from its first or locked position, illustrated in FIG. 19, to its second or unlocked position, illustrated in FIG. 20, as the bolt 243 of the targeting device 21 is screwed into the proximal end of the nail head 166. The actuation element can be a cylinder, piston or plunger, and can be free of external threads. The actuation element can also have other shapes, such as noncircular in cross section relative to the central longitudinal axis of the bolt 243.

In the foregoing manner, the mere coupling or connecting of the targeting device 21 to the nail 22 unlocks the locking mechanism 199 of the nail and permits the angle of the transverse aperture 25 of the nail, and thus fastener or screw 24, to be adjusted relative to the central axis 162 of the nail. As discussed above, pivoting of the fastener 24 is caused by inserting a suitable drive element through bolt 243 and housing 241 of the connector 37 into drive socket 224 of driver 223. Prior to such connecting of the targeting assembly 21 to the nail 22 or other implantable device, the locking mechanism 199 is in its locked position so as to preclude angular adjustment of transverse aperture 25 or any fastener 24 therein.

Although implantable device 22 can have an internally threaded proximal end, in any embodiment the implant insertion device of the invention can be utilized with any implantable device having any type of threaded proximal end. In this regard, for example, the proximal end of the implantable device can be internally threaded, externally threaded or any combination of the foregoing. The implant insertion device of the invention can be configured to accommodate any such type of threaded implantable device.

It is appreciated that other intramedullary nails, and other implants, can be utilized with the implant insertion device and the inventions herein. It is also appreciated that other configurations or designs of implant insertion devices suitable for use with the inventions herein can be provided to pivot a guide sleeve through a continuous angular range relative to the implant insertion device. It is further appreciated that other configurations or designs of implant insertion devices can be provided that rotate the guide sleeve relative to the implant insertion device and simultaneously move the guide sleeve longitudinally relative to the implant insertion device as the guide sleeve is pivoted relative to an implant, or more specifically relative to an aperture in an implant, and be suitable for use with the inventions disclosed herein.

Figure 21:
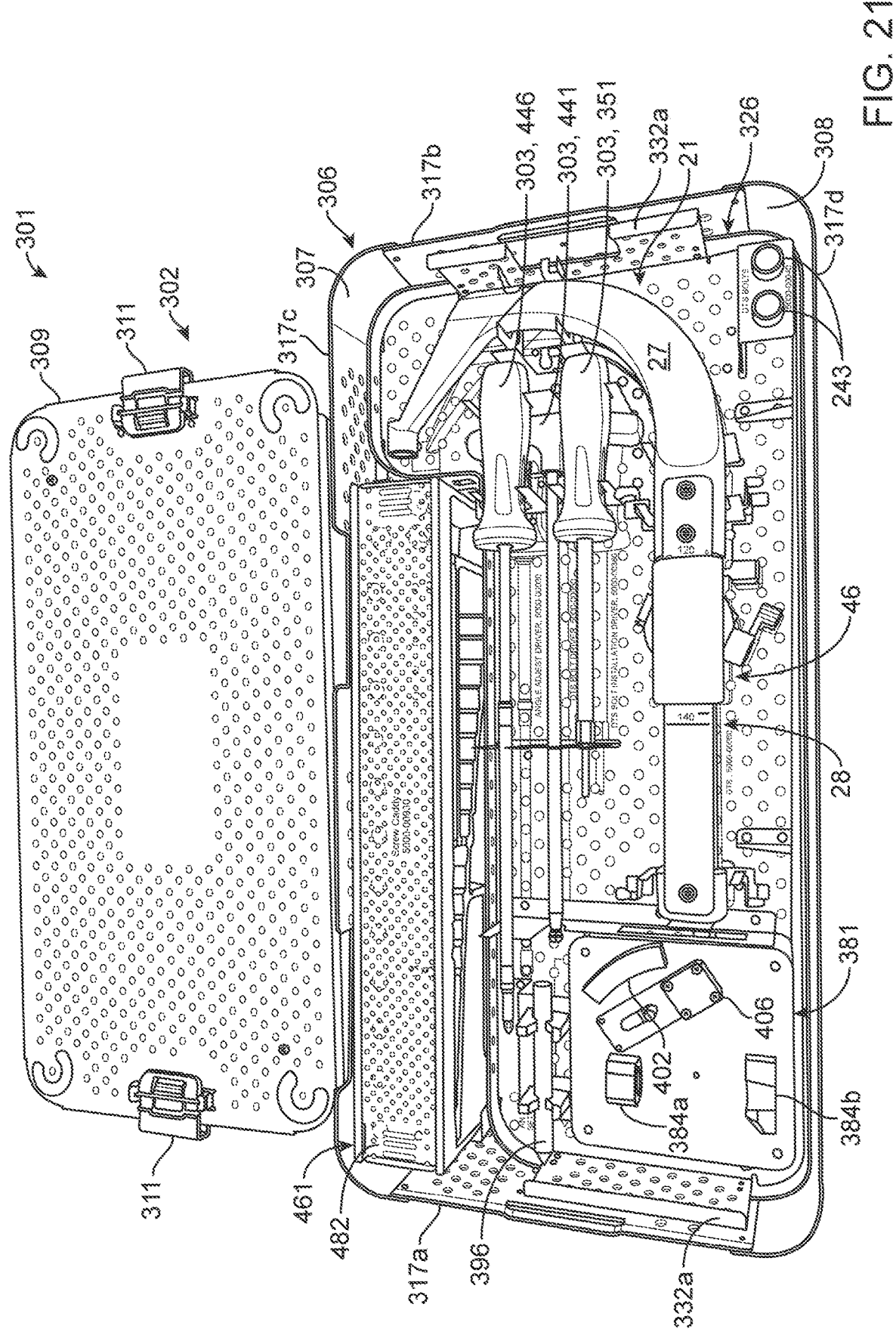
FIG. 21 is a top plan view of an instrument sterilization tray assembly of the present invention stocked with instruments.
Figure 22:
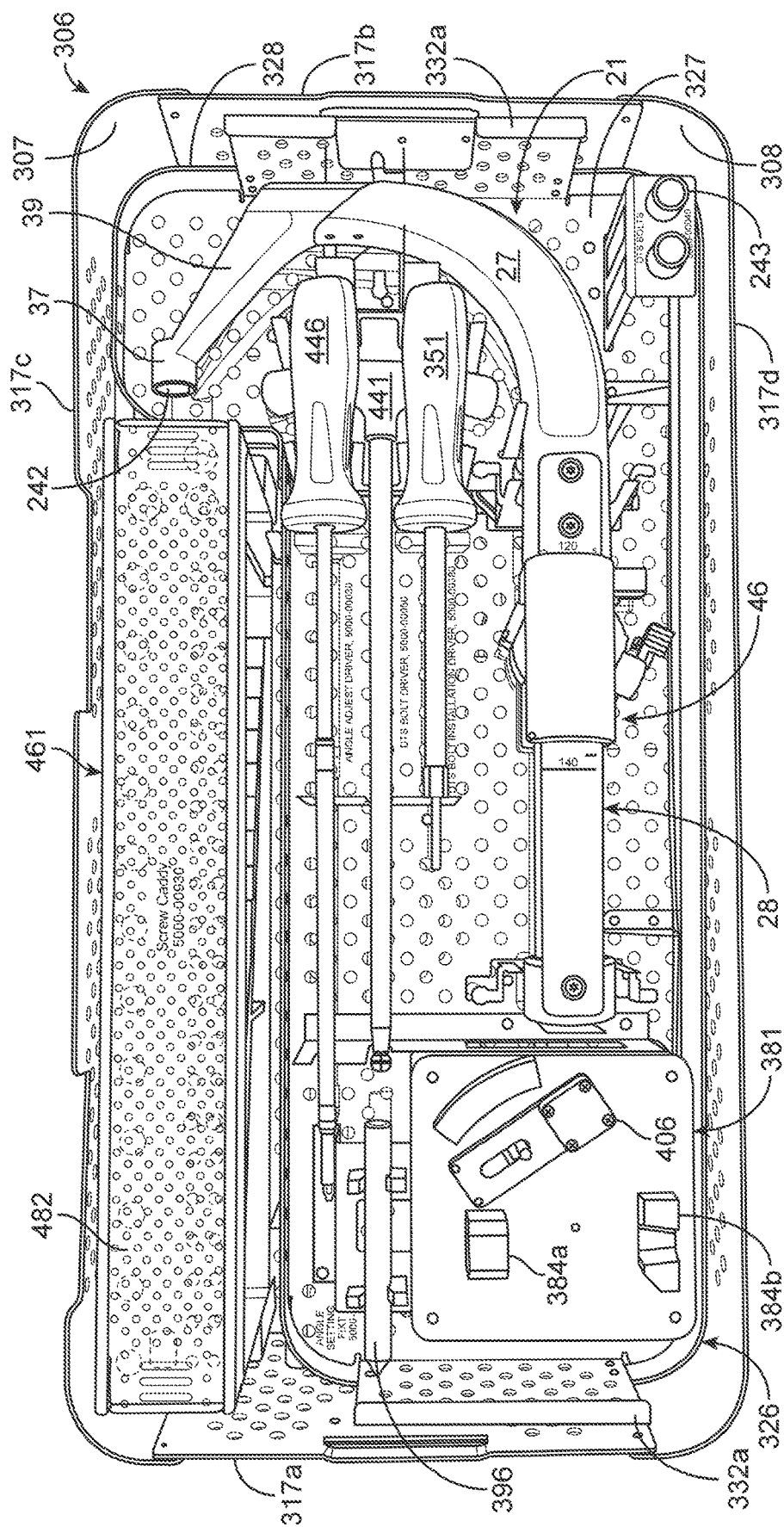
FIG. 22 is a top plan view of a bottom portion of the instrument sterilization tray assembly of FIG. 21.

In any embodiment, an apparatus 301 can be provided for permitting an implant insertion device 21 to be coupled to an implantable device 21 while the implant insertion device 22 is seated within, held by or otherwise connected to a sterilizable medical instruments tray. In any embodiment, the apparatus 301 can include a sterilizable tray assembly 302 for receiving a plurality of medical devices or instruments 303 for use in a medical procedure and permitting the assembly 302 and the medical devices therein to be sterilized in any suitable manner, for example by autoclaving, steaming or sterile washing. In any embodiment, the assembly 302 can include a main instrument tray or container 306 having a cavity or bay 307 and an open top 308 and an instrument tray cover 309 for removably attaching to the main instrument tray 306, for example by any suitable means such as one or more fasteners or clips 311 (see FIGS. 21, 22). The main instrument tray or container 306 and the removable cover 309 can be sterilizable and can be made from any suitable material such as stainless steel, composites, plastics or any combination of the foregoing. The main instrument tray can include a base 316, for example a rectangular planar base, and a plurality of peripheral walls 317 extending upwardly from the base. In one example, first and second opposite end walls 317a, 317b can extend perpendicularly upwardly from the ends 316a of the base and first and second opposite sidewalls 317c, 317d can extend perpendicularly upwardly from the sides 316b of the base between the first and second end walls, so as to form a rectangular bay or cavity within the main instrument tray. A plurality of suitable fixtures 318, for example a plurality of clips or brackets, can be secured to the base 316 of the main instrument tray for receiving a plurality of medical devices or instruments 303 to be utilized in a medical procedure. Such medical instruments can include, for example, a conical reamer, a proximal reamer, a multi-hole trocar, an offset proximal reamer sleeve, a long screw sleeve 23, a lag screw trial or fastener simulating element, a cannulated awl or any combination of the foregoing.

Figure 23:
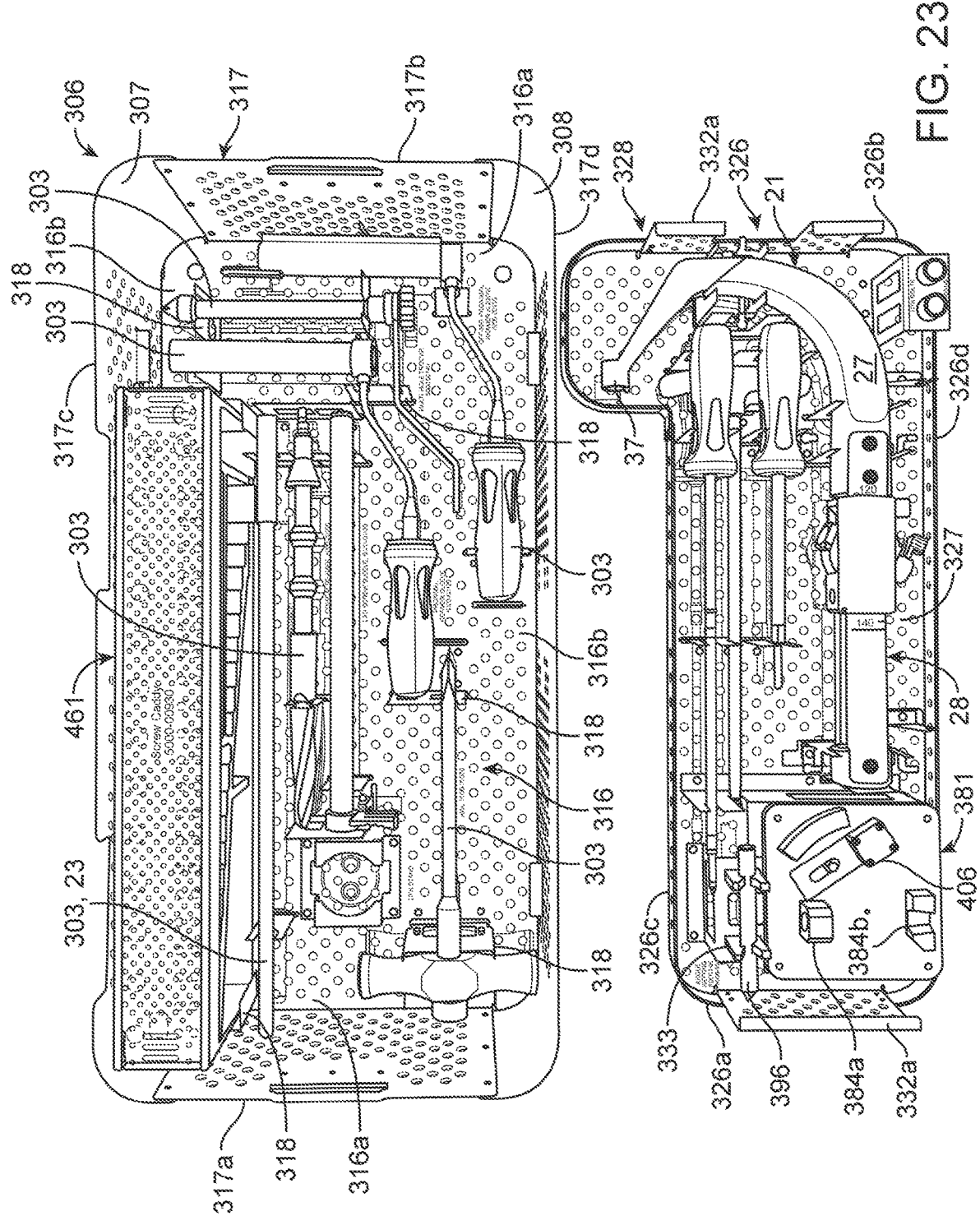
FIG. 23 is a top plan partially dissembled view of the bottom portion of the instrument sterilization tray assembly of FIG. 22.

The one or more of the fixtures 318 can additionally serve as posts or other suitable support elements for supporting an additional instrument tray 326 within the cavity or bay 307 of the main instrument tray 306. The additional tray 326 can be a sterilizable tray. One embodiment of a suitable additional tray or sub tray 326 is illustrated disposed in the main instrument tray 306 in FIG. 22 and removed from and alongside the main instrument tray in FIG. 23. The instrument sub tray is additionally illustrated in FIG. 24 with a plurality of medical devices or instruments 303 attached thereto and in FIGS. 25-29 with only an implant insertion device 21 secured thereto.

In any embodiment, the additional instrument tray or sub tray 326 can be made of any suitable material such as stainless steel, composites, plastics or any combination of the foregoing and can have opposite first and second ends 326a, 326b and off opposite first and second sides 326c, 326d extending perpendicularly between the first and second ends and upwardly from base 327 (see FIGS. 23-39). The first and second sides 326c, 326d can be referred to as the first and second main sides of the additional instrument tray. Ends 326a, 326b and sides 326c, 326d can define a base 327 of the tray 326, which in any embodiment can be planar or any other shape. An extension 328 of any suitable size and shape, for example a rectangular extension, can extend outwardly from one of the sides of the sub tray, for example from base 327 of the sub tray. In any embodiment, the extension 328 extends outwardly from the first main side 327c adjacent the second end. In any embodiment, the extension 328 can include a first side 328a extending perpendicularly from the first main side 327c and an opposite second side 328b extending from the first main side colinearly with the second end 326b of the sub tray 326. The extension can have an end 328c extending perpendicularly between the first and second sides 328a, 328b of the extension and thus parallel to the first main side 327c of the sub tray 326. Sides 328a, 328b and end 328c can define a base 329 of the extension 328. Extension base 329 can be parallel to base 327, for example spaced upwardly or downwardly from base 327. In any embodiment the extension base 329 can be coplanar with the base 327.

The additional tray 326 can include a wall 332 extending upwardly from the base 327 around all or some of the perimeter of the base. In any embodiment, the wall 332 can extend upwardly from all or any part of base 327 and extension base 329. The wall 332 can be of varying heights, and in any embodiment can include at least one tab-like extension 332a at each end 326a, 326b of the sub tray, for example to facilitate removal of the sub tray from the cavity or bay 307 of the main instrument tray 306. One or more and as shown a plurality of medical devices or instruments 303 are secured to the base 327 of the tray, and in any embodiment from the base 327 and base 329, and in any embodiment extend within the confines of the tray. One or more suitable fixtures 333 can be provided for securing each of the medical instruments to the tray, for example one or more clips, fasteners, brackets or any other suitable securing devices. Fixtures can be secured to any portion of the tray 326, including the base of the tray. In any embodiment, an implant insertion device 21 is secured by such fixtures to the base of the tray, for example to base 327 of the tray 329. The implant insertion device can be of any suitable type, and in any embodiment can be implant insertion device or targeting device 21. In any embodiment, second portion 28 of the target device 21 can extend along second side 326d of the tray and first portion 27 and can extend along the second end 326b of the tray. A part of the first portion or arm 27 of the target device 21, such as gooseneck 39, can extend outwardly from the first side 326c of the sub tray and overlie the extension 328 of the sub tray. The end of the arm 27 of the implantable device 21 can include a connector, such as connector 37, having an axial bore or socket 242 extending therethrough from a first or proximal opening 247 adjacent gooseneck 39 to a second or distal opening 249 opposite the first opening 247. The connector 37, and the bore 242 extending therethrough, extend along longitudinal axis 336. The connector 37 can extend above extension 328, although it is appreciated that in any embodiment the connector can extend off of the base of tray 326, for example cantilever from an end 326a, 326b or side 326c, 326d of the tray 326.

In any embodiment, the implant insertion device 21 can be mounted to the tray in a manner which permits access to the end, for example connector 327, of the device 21 so as to permit an implantable device, for example device 22, to be mounted to implant insertion device 21 while the device 21 is secured or mounted to a tray, for example a sterilizable tray. In any embodiment, such mounting permits access to opposite ends of the device 21, for example opposite ends of connector 327, while the device 21 is mounted to a tray, for example sub tray 326. In any embodiment, for example where the end of the device 21 overlies a portion of the tray, the perimeter or peripheral wall 332 of the sub tray 326 can be free of a wall portion adjacent such end of the device 21, for example on the first side 328a of extension 328. For example, the wall 332 can be provided with a first opening 341 for permitting access to the end, for example connector 37, of the implant insertion device 21. In any embodiment, the perimeter of peripheral wall 332 of the sub tray can be free of a wall portion on the second side 328b of the extension. For example, the wall 332 can be provided with a second opening 342 for permitting access to the end, for example connector 37, of the implant insertion device. In any embodiment, the first opening 341 can be opposite the second opening 342. In any embodiment, the first opening 341 can be in the first side 328a of the extension 328 of the sub tray and the second opening 342 can be in the second side 328b of the extension of the sub tray. In any embodiment, the first and second openings 341, 342 in the peripheral wall 332 of the sub tray are aligned, for example aligned along an axis 343 extending parallel to and above the base of the sub tray. In any embodiment, such openings are axially aligned with the end, for example connector 37, of the implant insertion device 21. In any embodiment, the first opening 341 permits access to the distal opening 249 in connector 37 of implant insertion device or targeting device 21 and the second opening 342 permits access to the proximal opening 247 in the connector 37 at the end of implant insertion device 21. The first and second openings in the peripheral wall of the sub tray permit a suitable implantable device to be secured to the end of the implant insertion device 21 while the implant insertion device is secured to the base 327 of the sub tray 326, for example secured in its position for transport and sterilization on the sub tray.

In any embodiment, a method can be provided for preparing an implantable device having a proximal end, such as intermittent medullary rod or nail 22, for use with an implant insertion device having an end, such as targeting device 21 with connector 37, while the implant insertion device is secured to a sterilizable instruments tray, such as the sub tray 326 described herein. In one possible step of such method, the proximal end of the implantable device, for example device 22, is aligned with the end of the implant insertion device, for example device 21. For example, the proximal end of head 166 of intramedullary rod 22 can be aligned with connector 37 of targeting device 21 while the targeting device is secured to the sub tray 326. Thereafter, the end of the implant insertion device, while secured to the instruments tray, can be coupled to the end of the implantable device. For example, head 166 of intramedullary rod or nail 22 can be coupled to connector 37 at the end of the first portion 27 of targeting device 21. The coupling step can include threadedly coupling the implant insertion device to the implantable device, for example threadedly coupling connector 37 of targeting device 21 to the internally threaded portion 182a of intramedullary rod 22. Although the implant insertion device can be directly threaded to the implantable device, in any embodiment a threaded or fastening element distinct of the implant insertion device can be utilized to couple the implant insertion device to the implantable device. For example, fastening element or bolt 243 can be utilized to threadedly couple targeting device 21 to intramedullary rod 22, such as by seating the fastening element 243 within socket 242 of the connector 37 and the threadedly coupling external threads 261 of the fastening element 243 to the internally threaded portion 182a of the rod 22.

Figure 24:
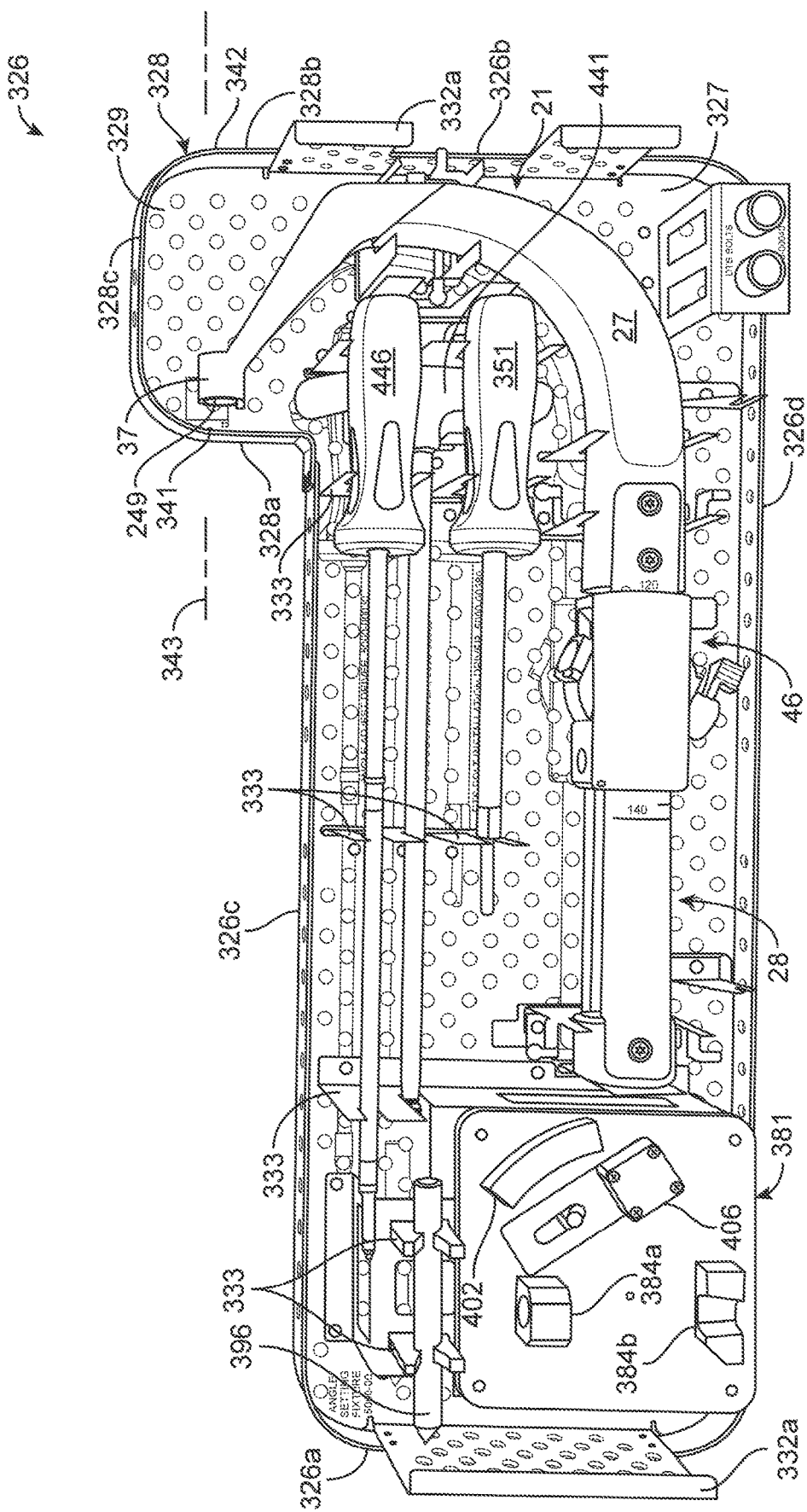
FIG. 24 is a top plan view of an instrument sub tray of the instrument sterilization tray assembly of FIG. 21.
Figure 25:
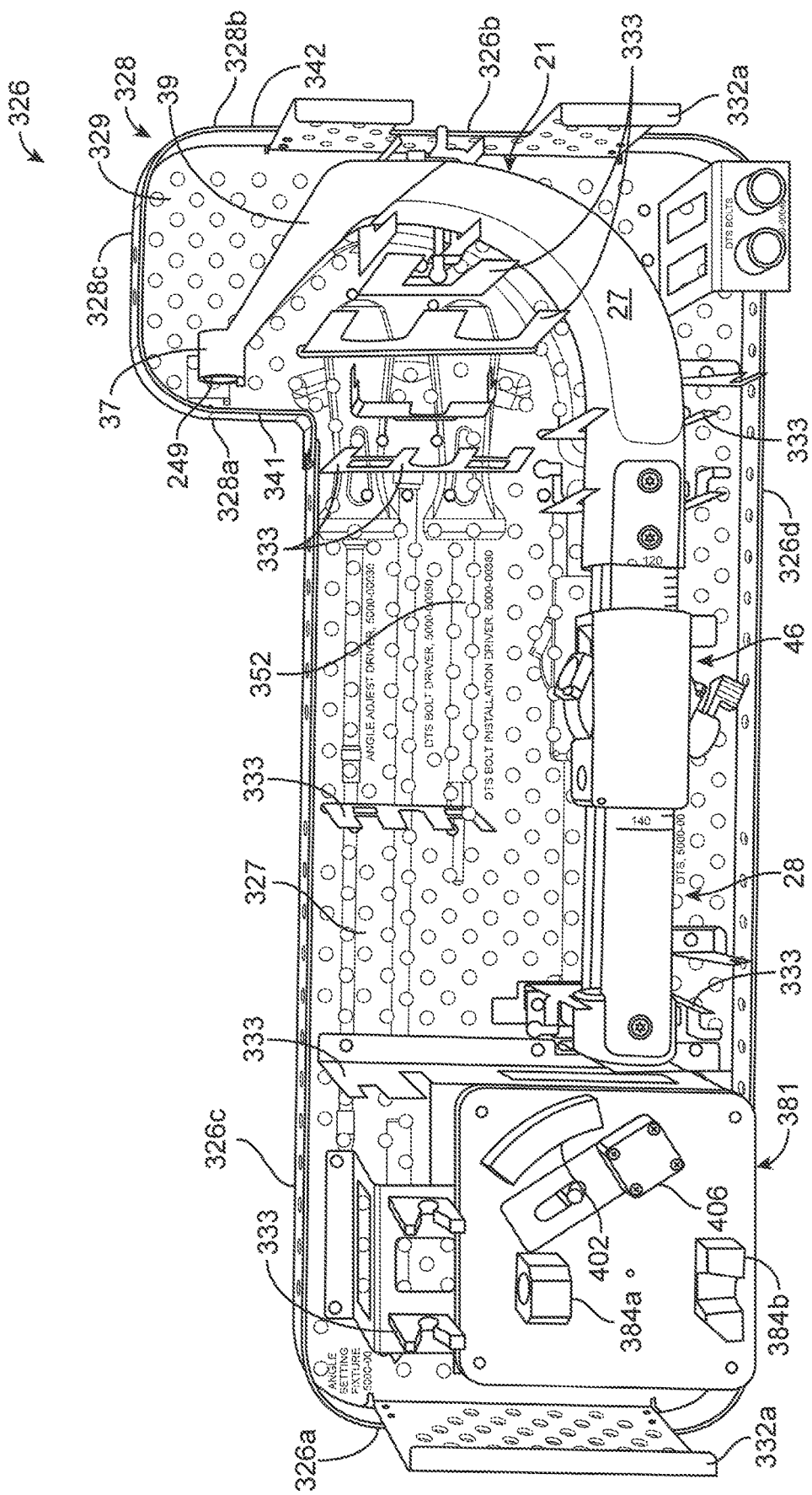
FIG. 25 is a top plan view of the instrument sub tray of FIG. 24 with only the implant insertion device therein.
Figure 26:
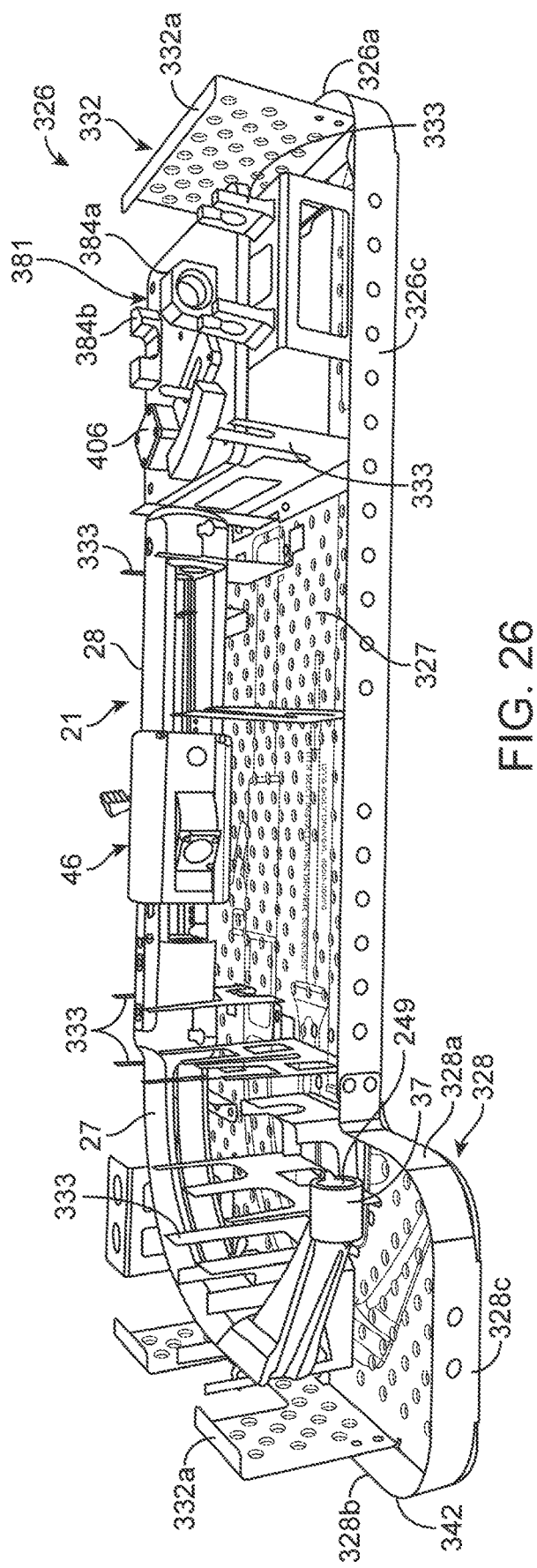
FIG. 26 is a first side perspective view of the instrument sub tray of FIG. 25.
Figure 27:
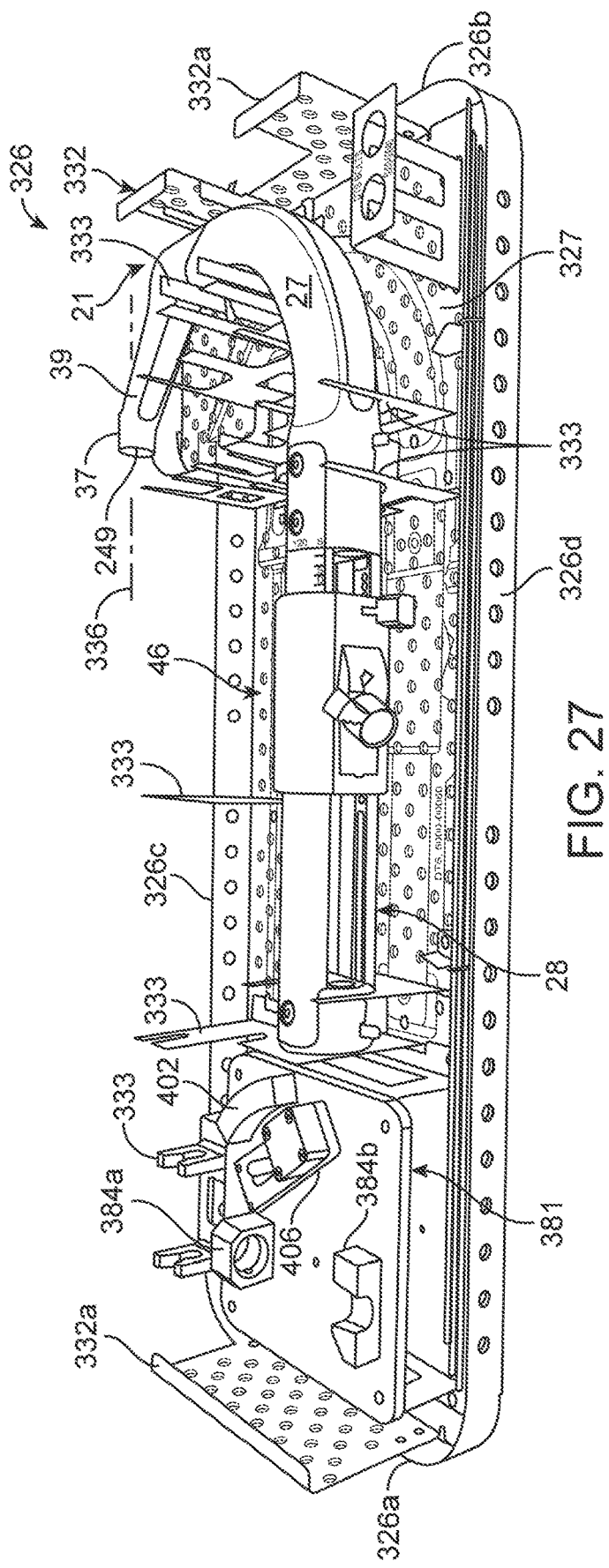
FIG. 27 is a second side perspective view of the instrument sub tray of FIG. 25.
Figure 28:
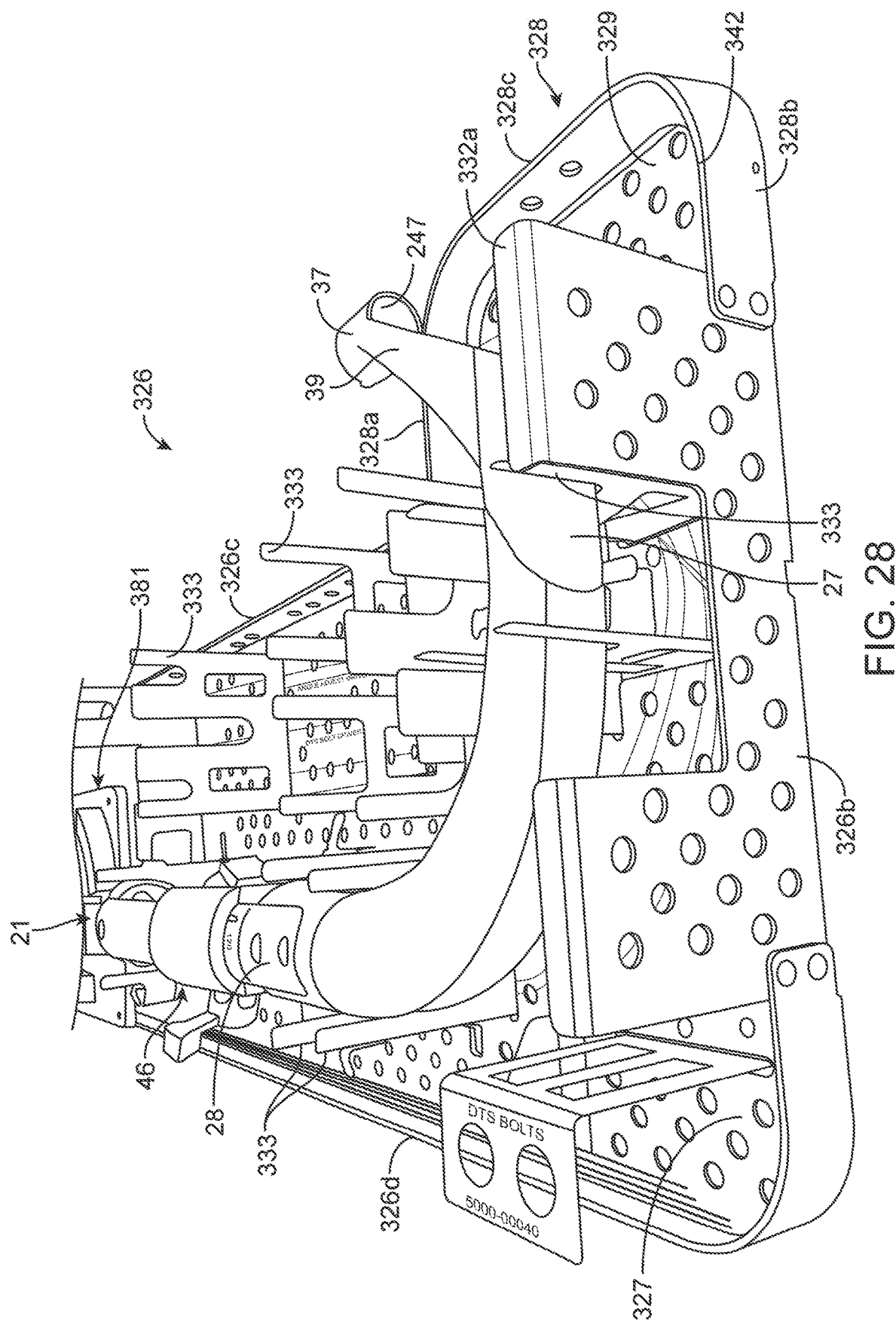
FIG. 28 is a first end perspective view of the instrument sub tray of FIG. 25.
Figure 29:
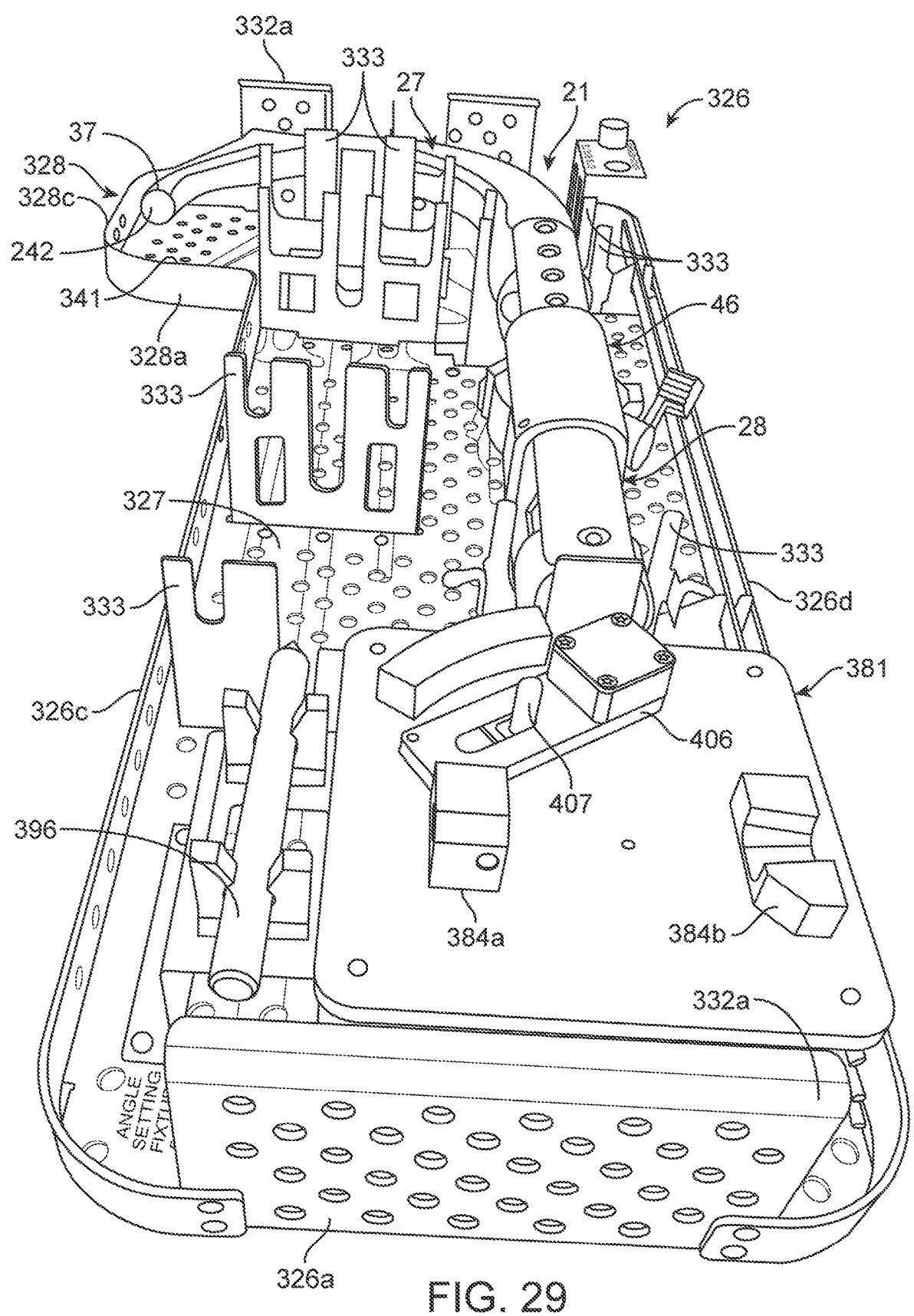
FIG. 29 is a second end perspective view of the instrument sub tray of FIG. 25.

In any embodiment, a tool can be provided for facilitating attachment of the end of the implant insertion device to a suitable implantable device. In any embodiment, the sterilization tray assembly 302 can be configured to carry such tool for transport and sterilization. In any embodiment, such tool can be secured to the instrument sub tray 326 by one or more fixtures secured to the base of the sub tray. Such fixtures can be of any suitable type, for example any of the fixtures described herein, for example fixtures 333 secured to the base 327 of sub tray 326. FIG. 24 illustrates such a tool 351 removably positioned and secured to the base 327 of the sub tray 326 and FIG. 25 illustrates a silhouette 352 provided on the base 327 of the sub tray for facilitating removable attachment of such tool 351 to the sub tray.

One embodiment of such tool, which can be for referred to as a bolt installation driver 351, is illustrated in FIGS. 39-44. The tool or driver 351 can include a handle 353 of any suitable type and an elongate shaft 354 extending forwardly from the handle along a longitudinal axis 356. The proximal end 354a of the elongate shaft can be secured to the handle 353 and the elongate shaft can have a distal or free end 354b which can be provided with a suitable driver 361 centered on the longitudinal axis of the shaft. In any embodiment, the driver 361 can be adapted to engage a threaded element such as a fastener or bolt 243, for example a socket provided in one end of such a fastening element, such as socket 257 provided on the proximal end of fastener 243. In any embodiment, the driver 361 is formed from a plurality of planar drive surfaces 326 centered on the longitudinal axis 356 of the shaft and in any embodiment the driver can be a hex driver. However, the bolt driver 351 can have any suitable end 361, for example formed from a plurality of suitably configured drive surfaces 362, such as hex, star, torques or any other shape that may fit into a jig or other bolt. An elongate guide element or guide 363 can extend forwardly of the driver 361 along the longitudinal axis 356 of the shaft 354. In any embodiment, the elongate guide is an elongate cylindrical guide 363. However, the elongated guide can be of any suitable shape that may have the effect of centering the jig or other bolt in the proximal end of the implantable device 22. The elongate guide 363 can be of any suitable length and in any embodiment the elongate guide can have a length at least equal to the length of the driver 361. In any embodiment, elongate guide 363 can have a length at least equal to twice the length of the driver. In any embodiment, the elongate guide 363 can have a length that may be longer or shorter than the total length of the driver. In any embodiment, the elongate guide 363 can have a length that may be longer or shorter than the total length of the fastener 243. In any embodiment, the elongate guide 363 can have a length at least equal to the length of the fastener 243. The elongate guide 363 can be made of any suitable material that may be rigid or flexible. The elongate guide 363 can have a transverse dimension less than the transverse dimension of the driver 361, for example a diameter less than the transverse dimension of the driver. In any embodiment, the elongate guide 361 can have a rounded distal or free end 364.

Figure 41:
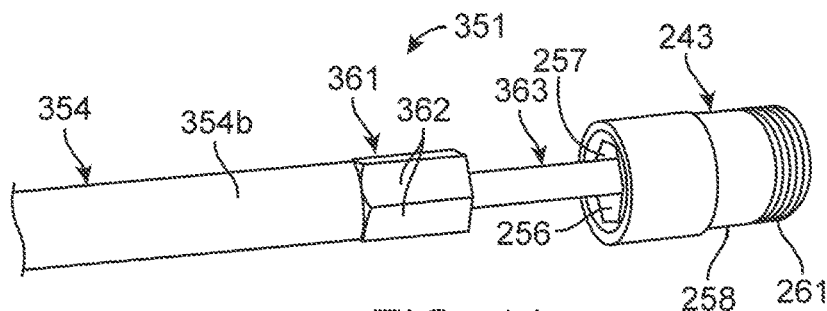
FIG. 41 is an illustration of a step of using the tool of FIG. 39 to secure an implant insertion device to an implantable device.
Figure 42:
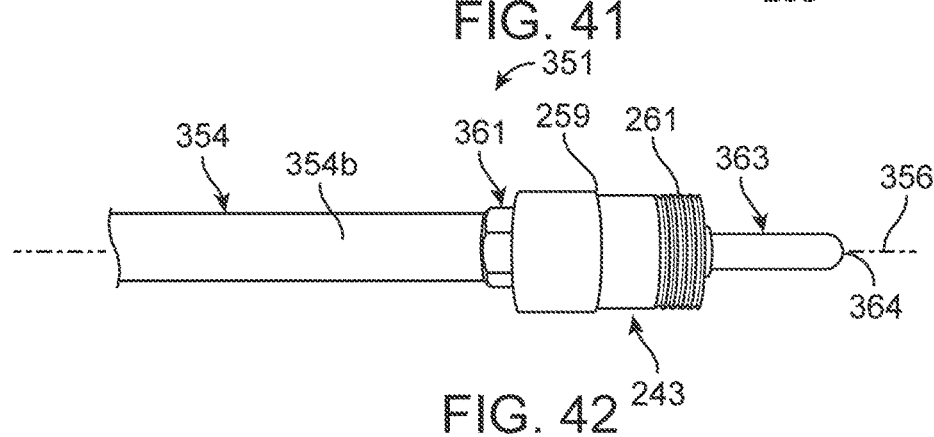
FIG. 42 is an illustration of another step of using the tool of FIG. 39 to secure an implant insertion device to an implantable device.
Figure 43:
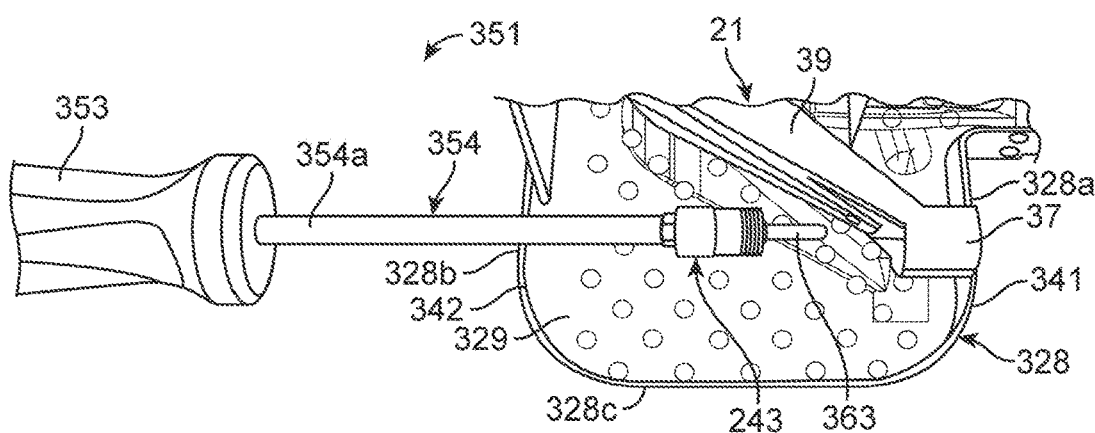
FIG. 43 is an illustration of a further step of using the tool of FIG. 39 to secure an implant insertion device to an implantable device.
Figure 44:
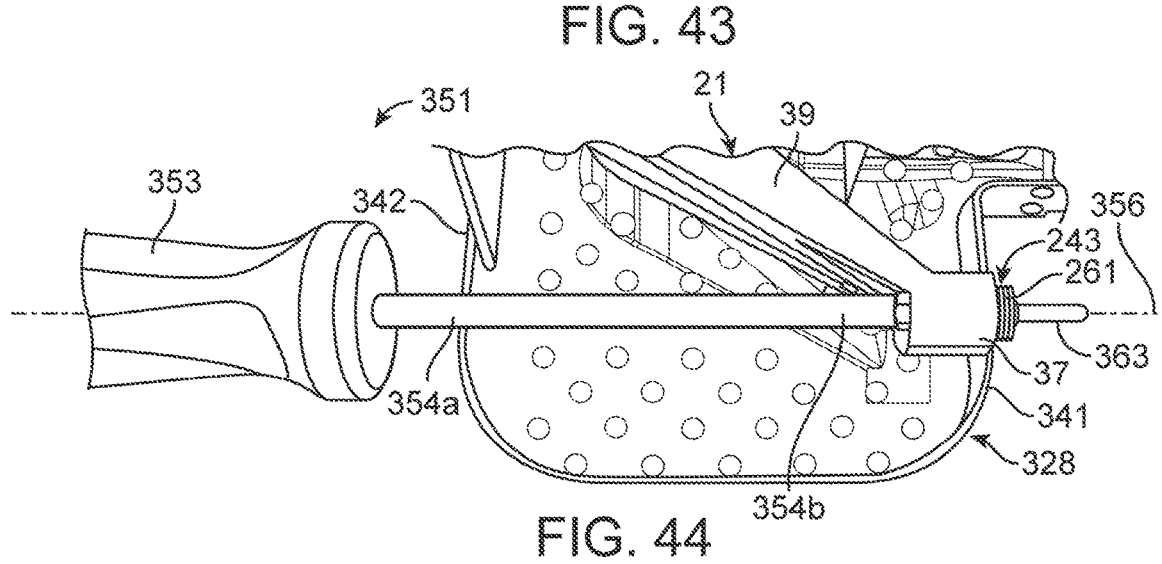
FIG. 44 is an illustration of yet another step of using the tool of FIG. 39 to secure an implant insertion device to an implantable device.
Figure 45:
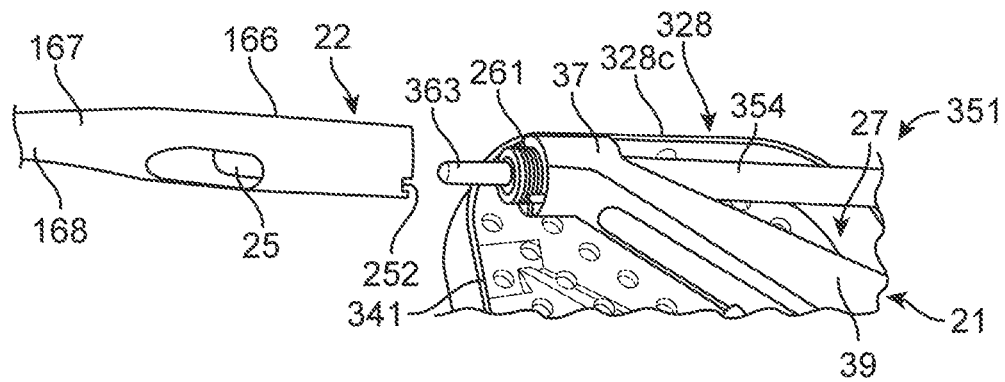
FIG. 45 is an illustration of a further step of using the tool of FIG. 39 to secure an implant insertion device to an implantable device.
Figure 46:
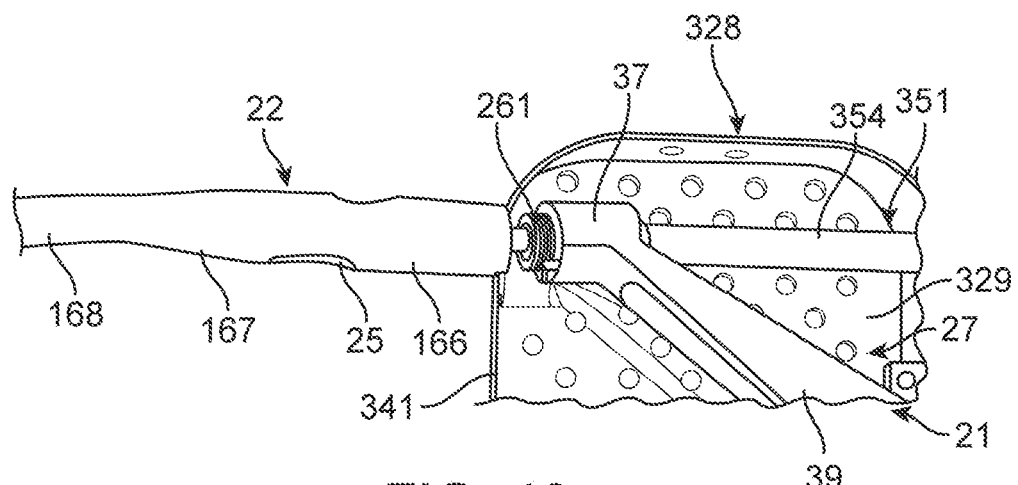
FIG. 46 is an illustration of another step of using the tool of FIG. 39 to secure an implant insertion device to an implantable device.
Figure 47:
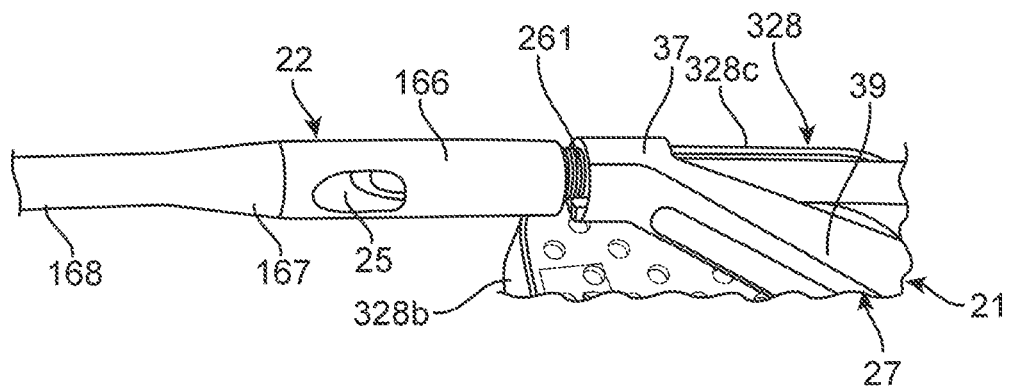
FIG. 47 is an illustration of yet a further step of using the tool of FIG. 39 to secure an implant insertion device to an implantable device.

A method can be provided for utilizing the tool 351 to prepare an implantable device for use with an implant insertion device, for example to prepare intramedullary rod 22 for use with targeting device 21. In any such method, the elongate guide of the tool can be extended through a threaded element carried by the end of the implant insertion device and into an opening in the threaded proximal end of the implantable device. For example, the elongate guide 363 of the tool 351 can be extended through hole or bore 256 of bolt 243 carried within socket 242 of the connector 37 and into proximal opening 183 at the proximal end of head 166 of the intramedullary rod 22. In any embodiment, the elongate guide 363 can be extended into bore 256 of the bolt 243 before the bolt is inserted into the connector 37, as illustrated in FIG. 41, and further extended into the bolt 243 until the driver 361 at the end of the tool 351 seats within the socket 257 provided at the proximal end of the bolt 243, as illustrated in FIG. 42. The bolt or other fastening element 243, carried by the distal end of the tool 351, can be inserted through the proximal opening 247 of the bore 242 of the connector 37, for example as illustrated in FIGS. 43-44. The fastener 243 and the distal end, for example guide 363, of the tool 351 can extend through the second opening 342 in the peripheral wall 332, if any, of the extension 328 of the sub tray 326 for so accessing the end of the targeting device 21, that is the connector 37 provided at the end of the targeting device 21. When the bolt or other fastening element 243 is fully seated within connector 37, the external threads 261 provided at the end of the fastener 243 can extend outwardly from the distal opening 246 of the connector and the elongate guide 363 of the tool 351 can extend forwardly from the fastener 243. As illustrated in FIG. 45, the elongate guide 363 of the tool 351 can extend through the first opening 341 the peripheral wall 332, if any, of the sub tray 326 when the bolt or other fastener 243 is so seated within the connector 37. In any embodiment, the proximal end of the head 166 of the intramedullary rod 22 can be moved through the first opening 341 in the peripheral wall, if any, of the sub tray towards the connector 37, as illustrated in FIG. 45. As the head 166 is moved closer to the connector 37, the elongate guide 363 of the tool 351 can extend into the proximal opening 183 provided in head 166, as illustrated in FIG. 46. The elongate guide 363 can be further extended into a bore provided at the proximal end of the implantable device, and extending distally from an opening in the proximal end of the implantable device, for facilitating centering of the threaded element on the threaded proximal end of the implantable device. For example, further movement of the head 166 and the connector 37 towards each other can cause the elongate guide 363 of the tool 351 to extend into the longitudinally-extending bore 226 of the head 166, which extends distally from drive socket 224 in driver 223 within the head of intramedullary rod 22. The cooperative engagement of the elongate guide of the tool in the bore within the head of the implantable device aids in centering the threaded end of the implantable device with the threaded element carried by the distal end of the implant insertion device. For example, as illustrated in FIG. 47, the cooperative engagement of the elongate guide 363 of the tool 351 with bore 226 of the head aligns the external threads 261 of the fastener or bolt 243 with the internally threaded portion 182a of the head so that further rotation of the shaft 354 of the tool 351 causes the external threads 261 to fully engage the internally threaded portion 182a and thus securely join the proximal end of the head 186 with the connector 37 at the end of the first portion 27 of the targeting device 21.

Figure 30:
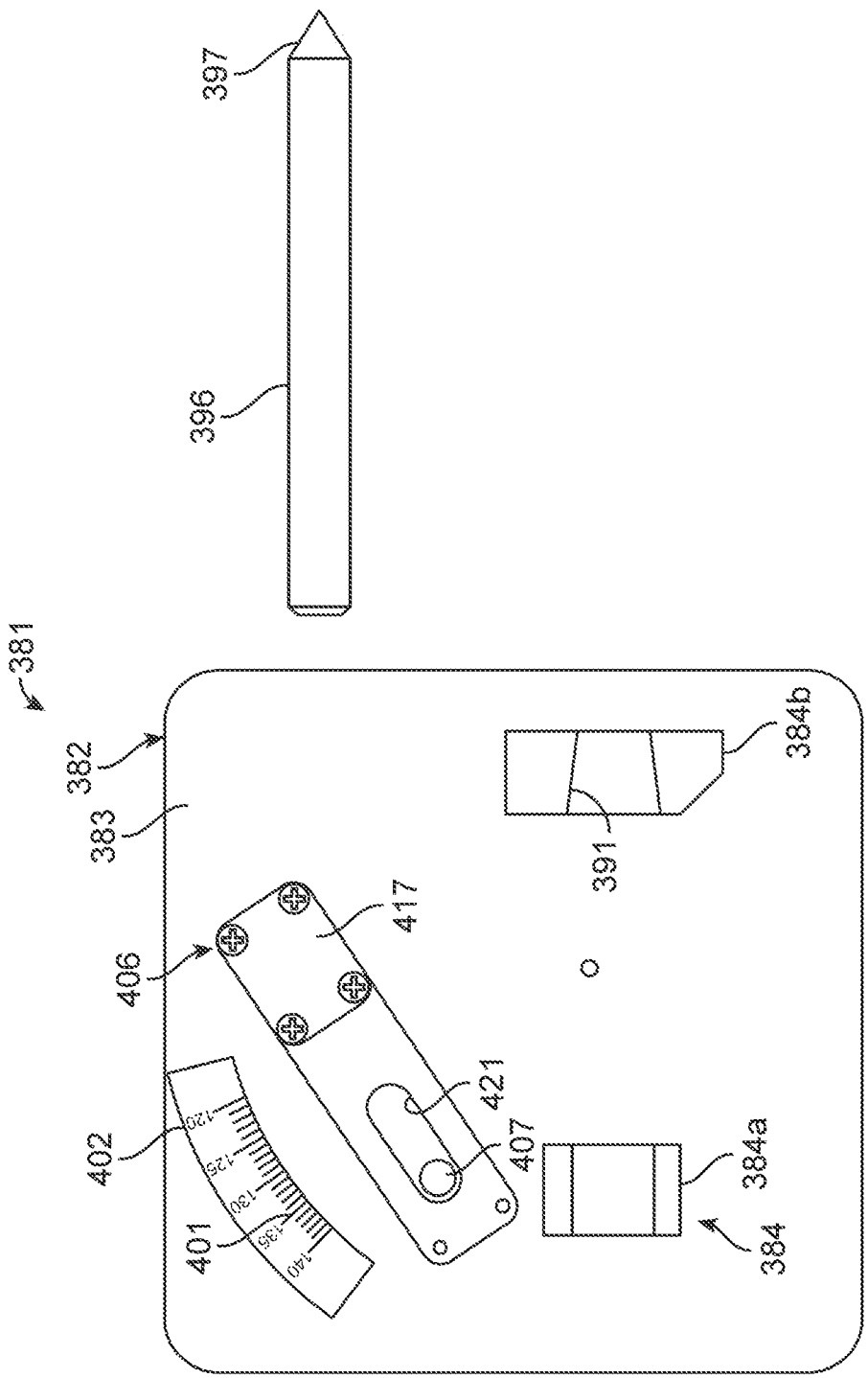
FIG. 30 is a top plan view of an angle adjustment assembly of the present invention.
Figure 31:
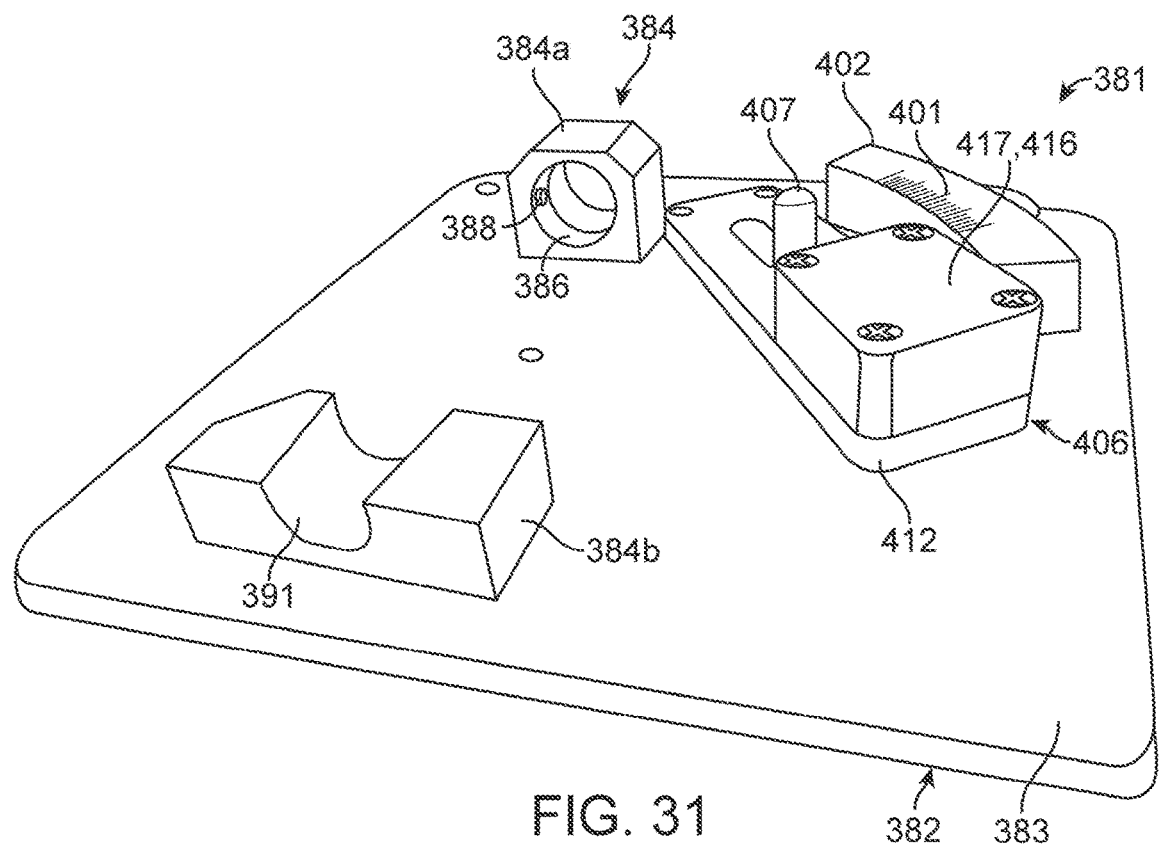
FIG. 31 is a front perspective view of the angle adjustment assembly of FIG. 30.
Figure 32:
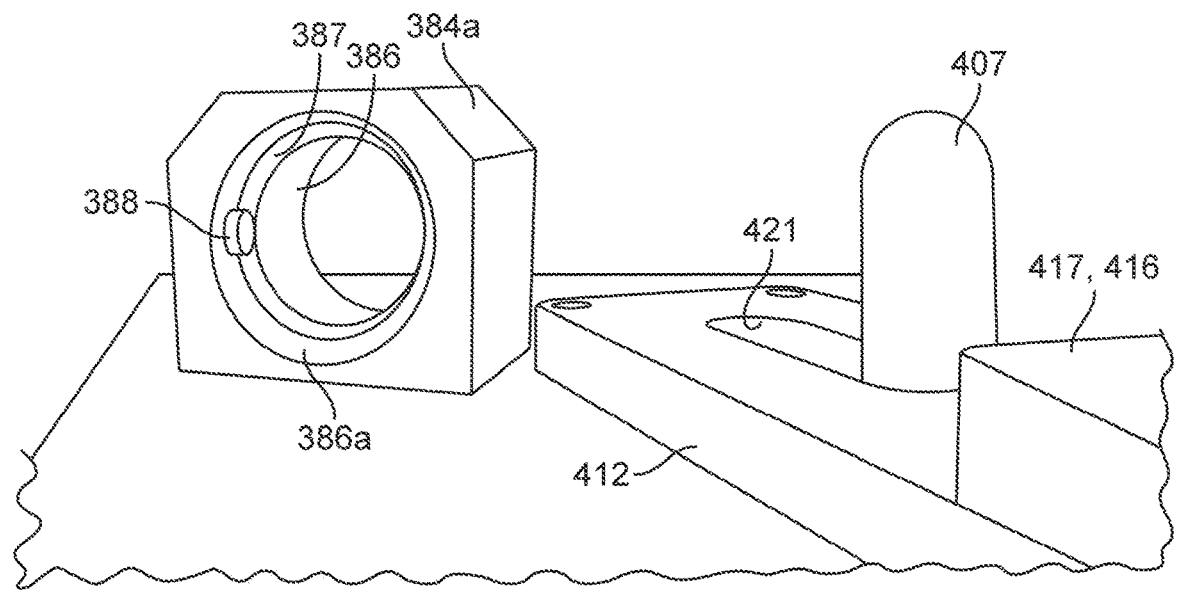
FIG. 32 is an enlarged perspective view of a portion of the angle adjustment assembly of FIG. 31.

In any embodiment, a mechanism or assembly is provided for use with an implantable device having an angularly adjustable transverse hole for adjusting or presetting the angle of such hole prior to use of the implantable device (see FIGS. 30-32). In any embodiment, such assembly or mechanism is mounted on the instrument sub tray of the invention. For example, such mechanism or assembly can be mounted to the base of the sub tray along the second main side of the sub tray near the second end of the sub tray (see FIGS. 21-29). One suitable implantable device for use with such mechanism or assembly is intramedullary rod 22 having angularly adjustable transverse hole, bore or aperture 25.

The angle adjustment mechanism or assembly of the invention can be of any suitable type. In any embodiment, an angle adjustment assembly 381 can be provided that can include a base 382, for example a planar base, having an upper surface, for example a planar upper surface 383. At least one fixture 384 can be connected to the base 382 for removably securing the implantable device 22 to the base. In any embodiment, first and second spaced apart fixtures 382a, 382b can be provided on the upper surface of the base for removably securing the implantable device 22 to the angle adjustment assembly or mechanism 381. In any embodiment, the first fixture 384a is tubular and provided with a bore 386 extending therethrough having an enlarged annular portion 386a at one end thereof and terminating at an annular seat 387 for receiving the proximal end of the implant insertion device, for example the proximal end of head 166 of intramedullary rod 22 (see FIGS. 31-32). In any embodiment, the first fixture 384a can include an element 388 for engaging the proximal end of the implantable device to rotatably lock the implantable device about the longitudinal axis of the implantable device. For example, the first fixture 384a can include an angular lock element 388 of any suitable type, for example a tab or extension extending outwardly from the annular seat 376 into the enlarged annular portion 386a for registering with a registration slot provided on the proximal end of the implantable device, for example the registration slot or notch 252 provided on the proximal end of head 166 of intramedullary rod 22. In any embodiment, the second fixture 384b can include an open slot to cooperatively receive a portion of the implantable device. For example, the second fixture 384b can include a slot 391 that narrows or tapers towards one end to cooperatively receive neck 167 of intramedullary rod 22. Slot 391 can be referred to as a funnel-shaped slot or recess.

The angle adjustment assembly 381 can include any elongate element 396 for disposition within the angularly adjustable transverse hole, for example aperture 25, of the implantable device 22. The elongate element can have an end 397, which in any embodiment can be pointed. In any embodiment, the elongate element, which can be referred to as an angle setting pointer 396, can be carried by the instrument sub tray 326 of the invention, for example by one or more suitable brackets, clips or other fixtures 333 secured to the base of the sub tray, for example base 327 of the tray 326. In any embodiment, the elongate element 396 can resemble a fastener for use with the implantable device. In any embodiment, the elongate element 396 can be cylindrical and can have a diameter that approximates the diameter of the fastener to be utilized with the implantable device 22.

The angle adjustment assembly 381 can further include features which indicate the angle of the angularly adjustable transverse hole of the implantable device being used with the assembly. In any embodiment, angle indicia 401 can be provided, for example on the upper surface or face of the base. In any embodiment, a plate 402 can be secured to the upper surface 383 of the base 382 and can be provided with the angle indicia 401 thereon. In any embodiment, the angle indicia can be an arcuate scale 401 having a radius centered at the pivot axis of the angularly adjustable transverse hole, for example aperture 25, in the implantable device.

The angle adjustment assembly 381 can include a spring mechanism 406 carried by the base 382 for engaging the elongate element 396 when the elongate element is disposed in the angularly adjustable transverse hole, for example aperture 25, of the implantable device. The spring mechanism 406 can be of any suitable type, and in any embodiment can include an upstanding pin 407 or other element that engages one side of the elongate element 307. A suitable spring 408 can be included in the spring mechanism 406 to urge the upstanding pin 407 against the elongate element during use of the angle adjustment assembly 381. The spring mechanism 406 can serve to simulate a load on a fastener extending through the angularly adjustable transverse hole when the implantable device is in use with a fastener, for example a load that would be exerted on the fastener in situ.

Figure 33:
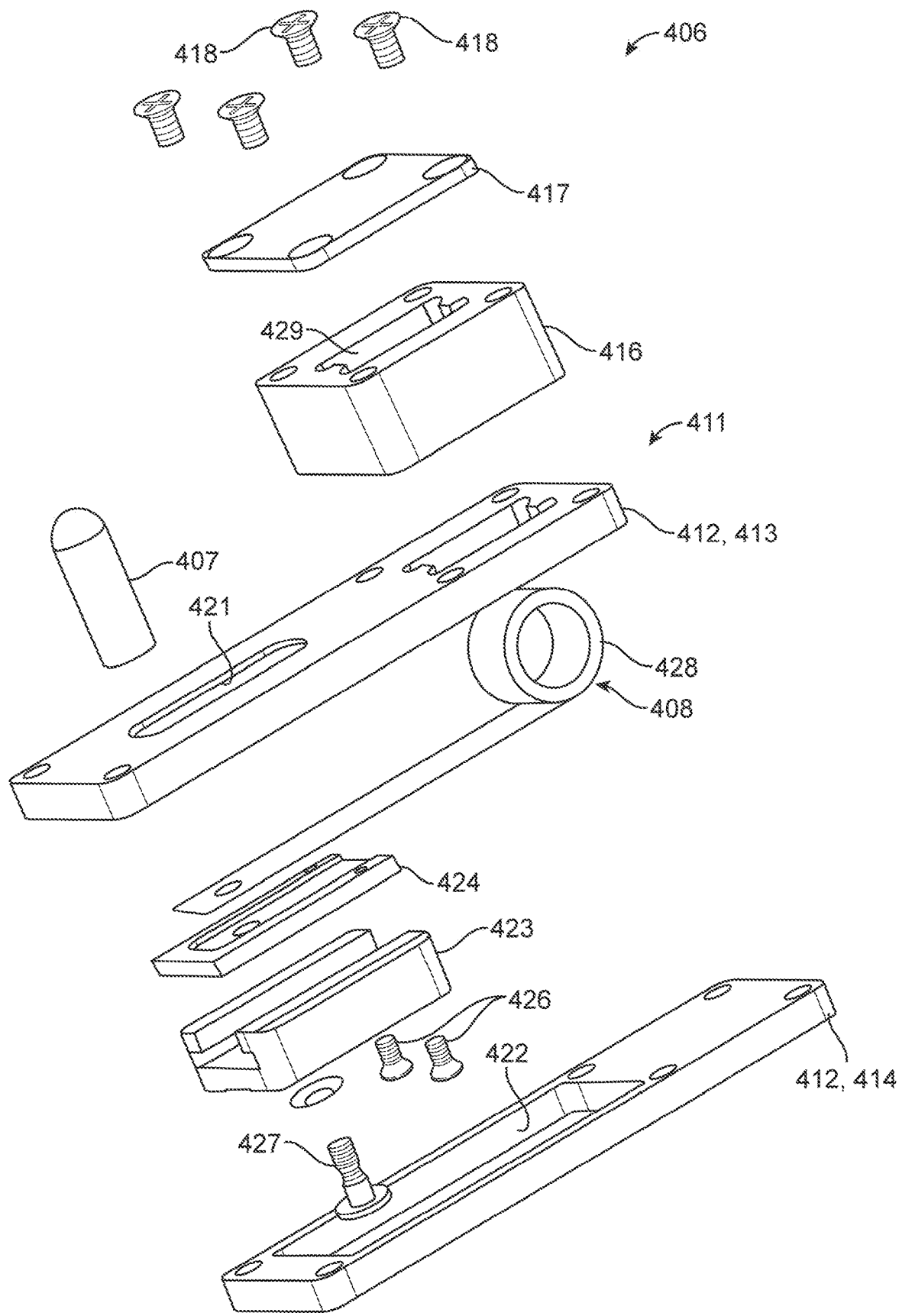
FIG. 33 is an exploded view of a portion of the angle adjustment assembly of FIG. 30.
Figure 38:
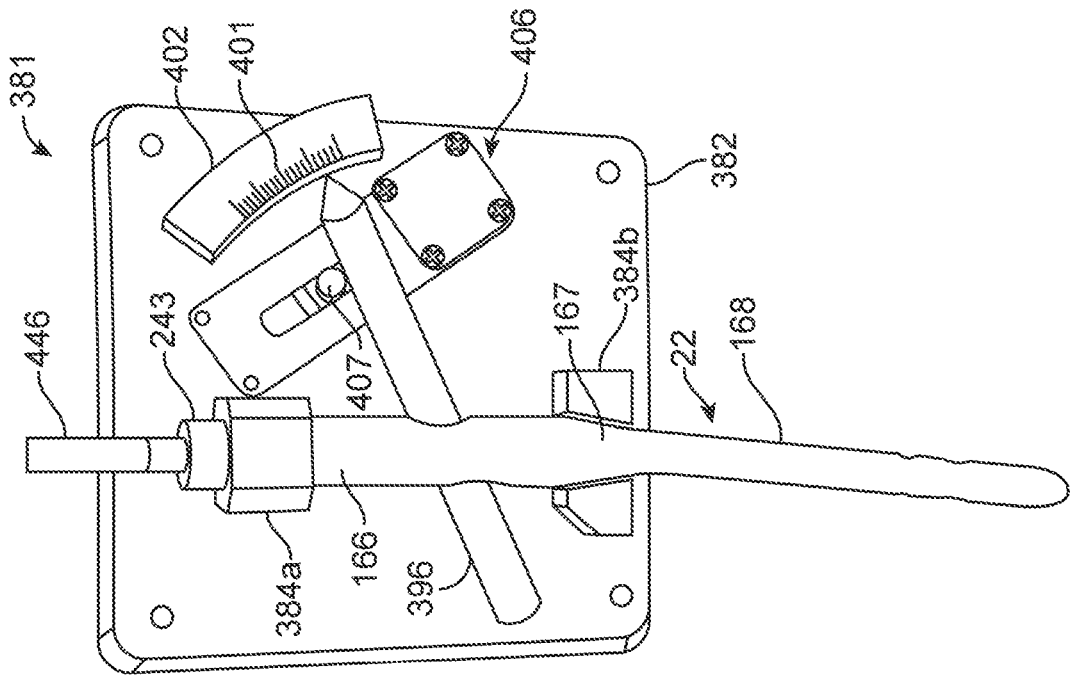
FIG. 38 is a top plan view of the angle adjustment assembly of FIG. 25 in use in a second position.

In any embodiment, spring mechanism 406 can include a housing 411 for receiving pin 407 and spring 408 (see FIG. 33). Housing 411 can include a lower portion 412 having a top part 413 and a bottom part 414. The housing 411 can further include an upper portion 416 that can sit atop one end of top part 413 and a cover 417 for joining to the top of upper portion 416. Cover 417, upper portion 416 and lower portion 412 can be secured to base 382 of the angle adjustment assembly 381 by any suitable means such as a plurality of screws or other fasteners 418. Top part 443 can include a slot or cavity 421 for movably receiving pin 407. Bottom part 414 can be provided with a slot or cavity 422 for slidably receiving a bearing 423. One end of spring 408, which can be a windup coil spring, can be connected to the bottom of pin 407 and bearing 423 by means of a guide 424. One or more screws or other fasteners 426 can secure guide 424 to bearing 423 and at least one screw or other fastener 427 can extend through bearing 423, guide 424, the end of spring 408 and into the bottom of pin 407 for joining together such components or elements of spring mechanism 406. The coiled portion 428 of spring 48 can extend through an opening at the end of top part 413 into a cavity 429 provided inside upper portion 416. Spring 408 serves to urge pin 407 towards one and of the spring mechanism 406, for example towards the upper portion 416 of the spring mechanism.

A method can be provided for determining an angle of an angularly adjustable transverse hole, for example aperture 25, in an implantable device 22 for receiving a fastener prior to implantation of the device 22. In one step of the method, the implantable device is secured to a body. For example, intramedullary rod 22 can be secured to the angle adjustment mechanism 381, which in any embodiment can be secured to a sterilizable tray, for example sub tray 326. An elongate element having an end can be inserted through the angularly adjustable transverse hole of the implantable device. For example, the elongate element or angle setting pointer 396 can be inserted through angularly adjustable transverse hole 25 in intramedullary rod 22. The end of the elongate element can be observed relative to the body to determine the angle of the angularly adjustable transverse hole in the implantable device. For example, the end 397 of the angle setting pointer 396 can be observed relative to the base 382 of the angle adjustment assembly 381 to determine the angle of the angularly adjustable transverse hole 25 in intramedullary rod 22. In any embodiment, angle indicia can be carried by the base and the observing step can include observing the end of the elongate element relative to the angle indicia to determine the angle of the angularly adjustable transverse hole in the implantable device. For example, the free end of the elongate element, for example the pointed end 397 of the angle setting pointer 396, can be observed relative to the angle indicia 401 carried by the base 382 of the angle adjustment assembly 381 to determine the angle of the angularly adjustable transverse hole 25 in intramedullary rod 22.

Any embodiment of the step of securing an implantable device to a body can include inserting the proximal end of the implantable device into the enlarged portion of the board of the first fixture and placing another portion of the implantable device into the second fixture. For example, the proximal end of head 166 of intramedullary rod 22 can be inserted into the enlarged portion 386a of the tubular first fixture 384a such that the end of the head 166 engages the internal annular seat 387 of the fixture 384a (see FIG. 34). The head 166 can be rotated within the first fixture 384a until the angular lock element 388 provided within the first fixture engages the slot 252 at the proximal end of the head 166 so as to rotatably lock the head 166 about the longitudinal axis of the head relative to the first fixture. The implantable device can be secured to the angle adjustment assembly by any suitable means. In any embodiment, a fastening element can be utilized to secure the proximal end of the implantable device to the first fixture. For example, a fastening element such as bolt 243 can be inserted through an opening into the bore 386 of the first fixture 384a opposite the enlarged portion 386a so that the external threads 261 of the bolt threadably engage the internally threaded portion 182a inside head 166 of intramedullary rod 22. A suitable tool or bolt driver can be utilized for threading and tightening the fastening element to the implantable device. For example, a bolt driver 441 having a driver 442 at its free or distal end 441a that is sized and configured to cooperatively engage socket 257 at the proximal end of bolt 243 can be provided, as illustrated in FIG. 34.

Any embodiment of inserting an elongate element 396 through the angularly adjustable transverse hole 25 of the implantable device 22 can include inserting the elongate element either before or after the implantable device is secured to the base 382 of the angle adjustment mechanism 381. In any embodiment, the elongate element can be inserted through the angularly adjustable transverse hole of the implantable device after attachment of the implantable device 22 to the base 382. One end of the elongate element, for example end 397, extends free of the implantable device 22 for indicating the angle of the angularly adjustable transverse aperture 22 (see FIG. 35). In any embodiment, such free end 397 of the elongate element 396 can be engaged by the spring mechanism 406 of the angle adjustment assembly 381 such that the upstanding pin 407 of the spring mechanism engages the free end 397 of the elongate element 396 and exerts a torque on the elongate element about the pivot axis of the elongate element, for example to simulate the load on a fastener being pivotably carried within the angularly adjustable transverse hole 25 of the implantable device 22 during use of the implantable device in situ.

In any embodiment, the method can include adjusting the angle of the angularly adjustable transverse hole 25 in the implantable device 22 while the implantable device 22 is secured to the body, for example base 382 of the angle adjustment mechanism 381 (see FIGS. 35-38). In any embodiment, the implantable element 22 can have a proximal end and a rotatable element carried by the proximal and the adjusting step can include rotating the rotatable element 396. For example, the adjusting step can include rotating rotatable or control element 197 of intramedullary rod 22 to adjust the angle of transverse hole 25 of the rod. Such adjusting step can include engaging the rotatable element with a tool to rotate the rotatable element. For example, a suitable angle adjust driver 446 can be utilized to engage drive socket 224 of the driver 223 so as to rotate control element 197 of the intramedullary rod 22. In any embodiment, the implantable device can have a proximal and the adjusting step can include engaging the proximal end with a tool to adjust the angle of the angularly adjustable transverse hole of the implantable device. For example, intramedullary rod 22 can include a proximal end and a suitable tool, for example driver 446, can be utilized to engage the proximal end of rod 22 to adjust the angle of transverse hole 25 of the rod. In any embodiment, the proximal end of the implantable device can have an opening and the adjusting step can include extending a tool into the opening in such proximal end. For example, intramedullary rod 22 can have a proximal opening 183 and a tool, for example driver 446, can be inserted into opening 183 for adjusting the angle of transverse hole 25 of the rod. In any embodiment, the implantable device can have a proximal end and an actuatable element carried within the proximal end and the adjusting step can include engaging the actuatable element. For example, intramedullary rod 22 can have an actuatable element 196, which can be referred to as a sleeve, carried within head 166 in the step of adjusting transverse bore 25 of the rod can include engaging the actuatable element.

Figure 37:
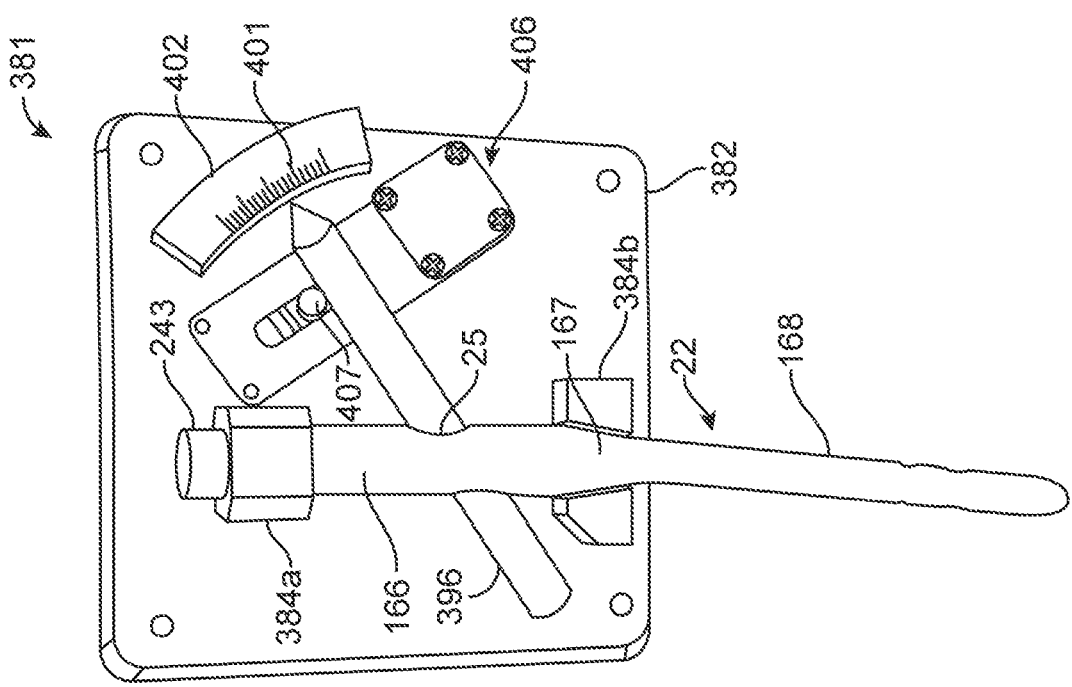
FIG. 37 is an illustration of yet another step of using the angle adjustment assembly of FIG. 25.
Figure 39:
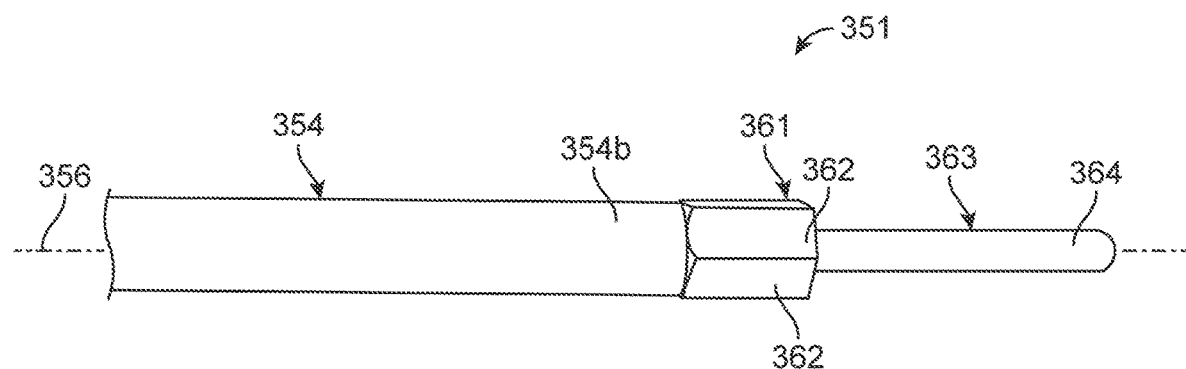
FIG. 39 is a plan view of the distal end of a tool of the present invention.
Figure 40:
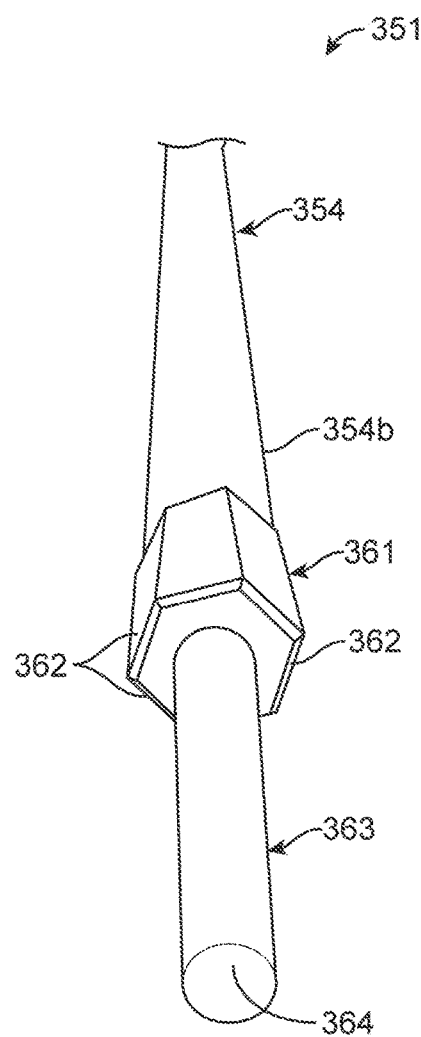
FIG. 40 is an end perspective end view of the distal end of the tool of FIG. 39.

The angle adjust assembly 381 of the invention can be utilized to adjust the angularly adjustable transverse bore of the implantable device between a first position, shown for example by the elongate element 396 being in a first position in FIG. 36, and a second position, shown for example by the elongate element 396 being in a second position in FIG. 37. The elongate element is shown in a third position in FIG. 38. The free end 397 of the elongate element 396 can be in the vicinity of the angle indicia 401 of the angle adjust assembly 381, in each position, so that such indicia indicates the angle of the angularly adjustable transverse hole 25 of the implantable device 22 in each position.

In any embodiment, the angle adjust assembly 381 of the present invention can be mounted to a sterilizable tray, for example sub tray 326 as shown in FIGS. 21-29, for carrying medical instruments. In any embodiment, the angle adjust assembly of the present invention can be free standing, for example as shown in FIGS. 34-38. In any embodiment, the angle adjust assembly 381 can be positioned on the tray such that the distal end of the implantable device 22 as secured to the angle adjust assembly 381 extends off the tray so as to minimize the footprint of the angle adjust assembly on the tray during use. See for example FIGS. 21-29. In any embodiment, the peripheral wall 332 of the tray, if any, can be provided with an opening for permitting the free end of the implantable device to extend from the tray 326 in a plane parallel to the base of the tray, for example base 327 of tray 326. In any embodiment, the peripheral wall 332 of the tray, if any, can be provided with an additional opening for permitting access to the proximal end of the implantable device 22 when mounted to the angle adjust assembly 381, for example by a suitable tool such as angle adjustment driver 446, to adjust the angle of the angularly adjustable transverse hole, for example aperture 25, of the implantable device. For example, the additional opening can be sufficient to permit the distal or working end of such a tool to extend in a plane parallel to the base of the tray as it accesses and engages the proximal end of the implantable device as secured to the angle adjust assembly 381 on the instrument tray, for example sub tray 326. In each case, the tray can be free of a wall, in at least such vicinity, for permitting the free end of the implantable device to extend from the tray, for permitting access to the proximal end of the implantable device or both.

Figure 48:
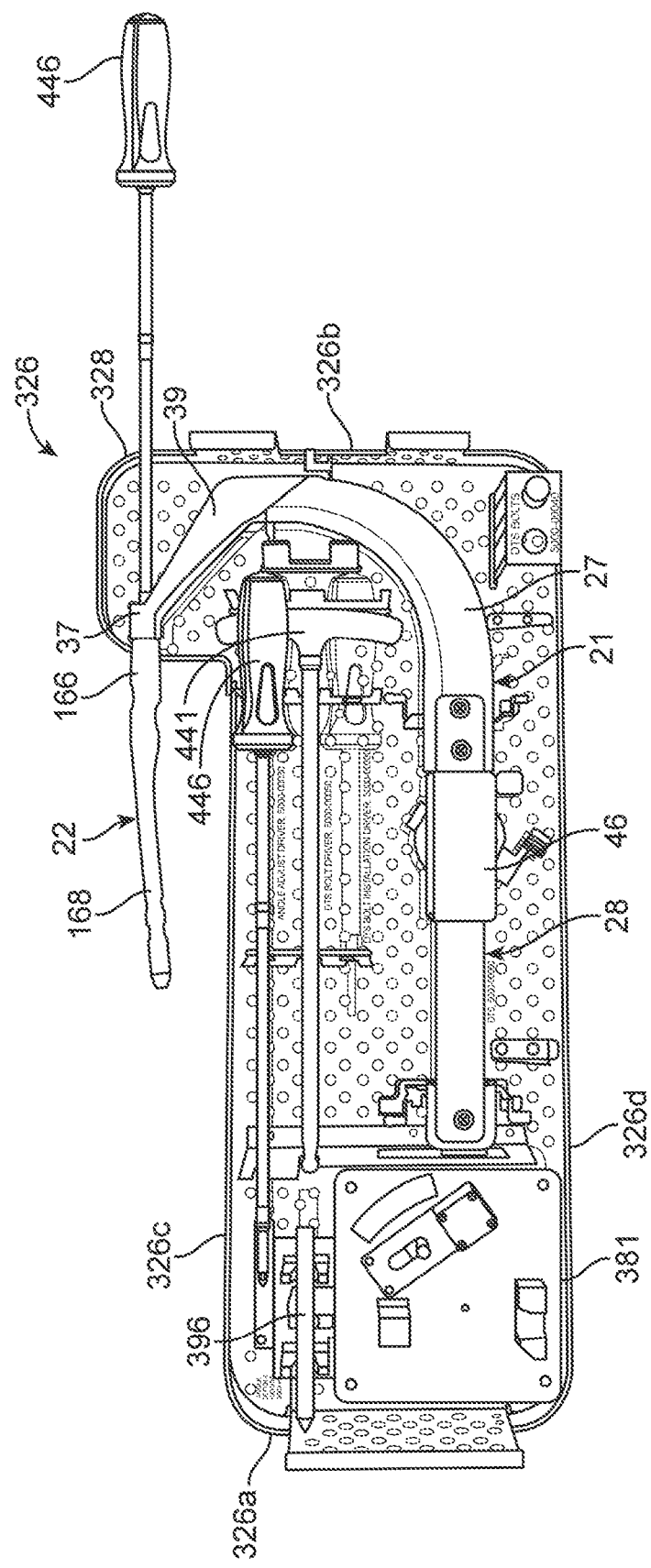
FIG. 48 is an illustration of another aspect of use of instrument sub tray of FIG. 25.
Figure 49:
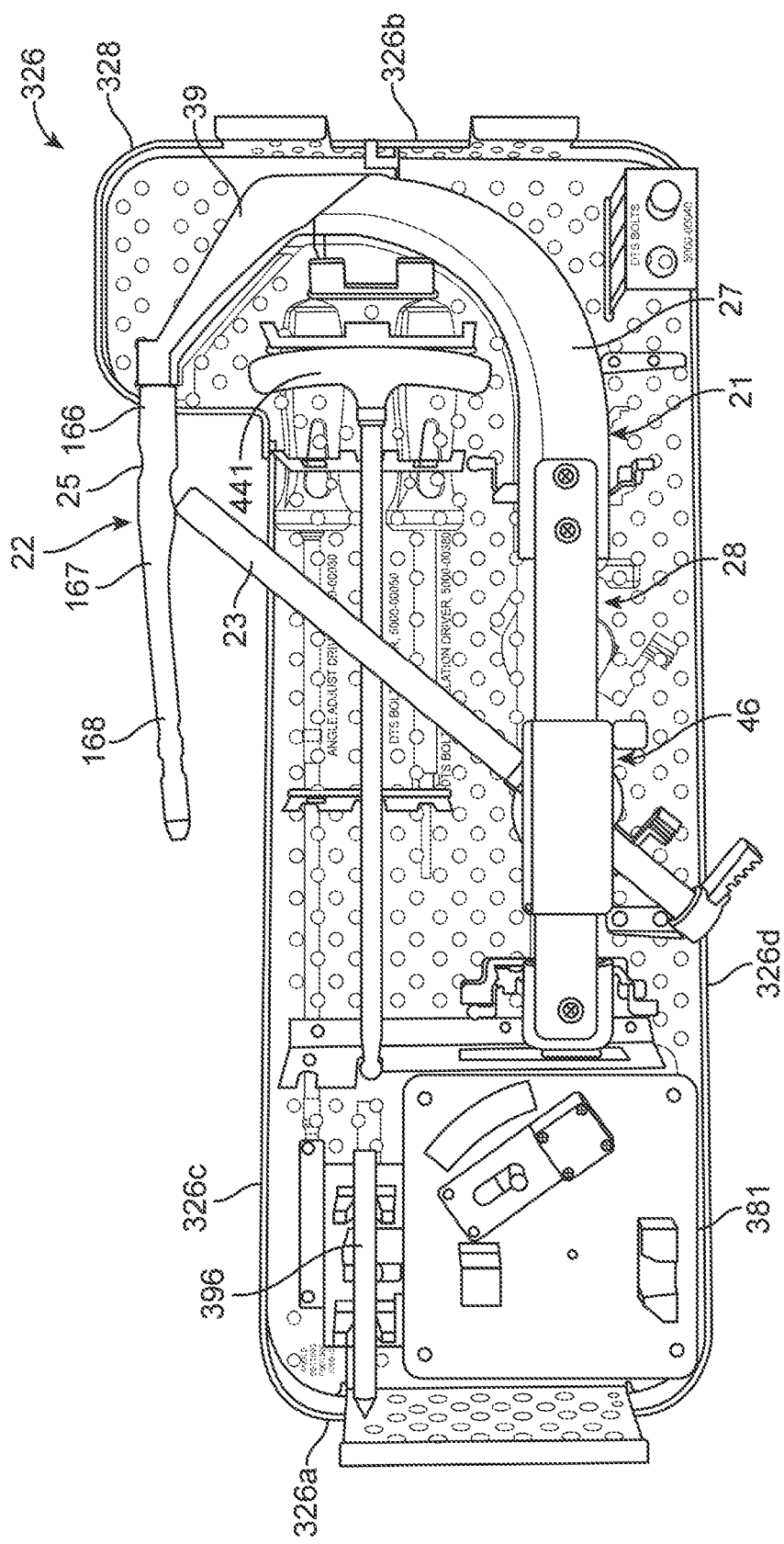
FIG. 49 is an illustration of a first step of a further aspect of use of the instrument sub tray of FIG. 25.
Figure 50:
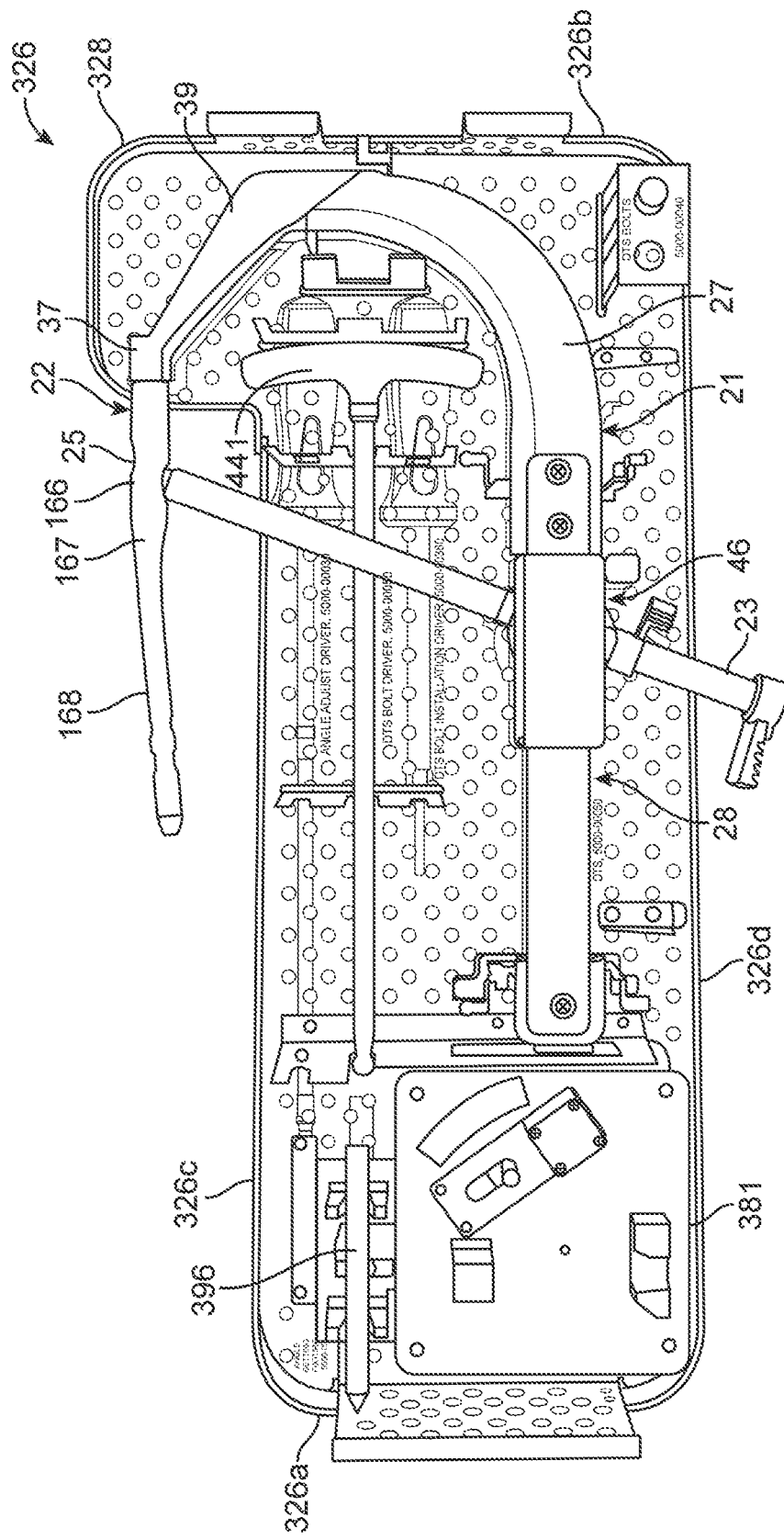
FIG. 50 is an illustration of a second step of a further aspect of use of the instrument sub tray of FIG. 25.
Figure 51:
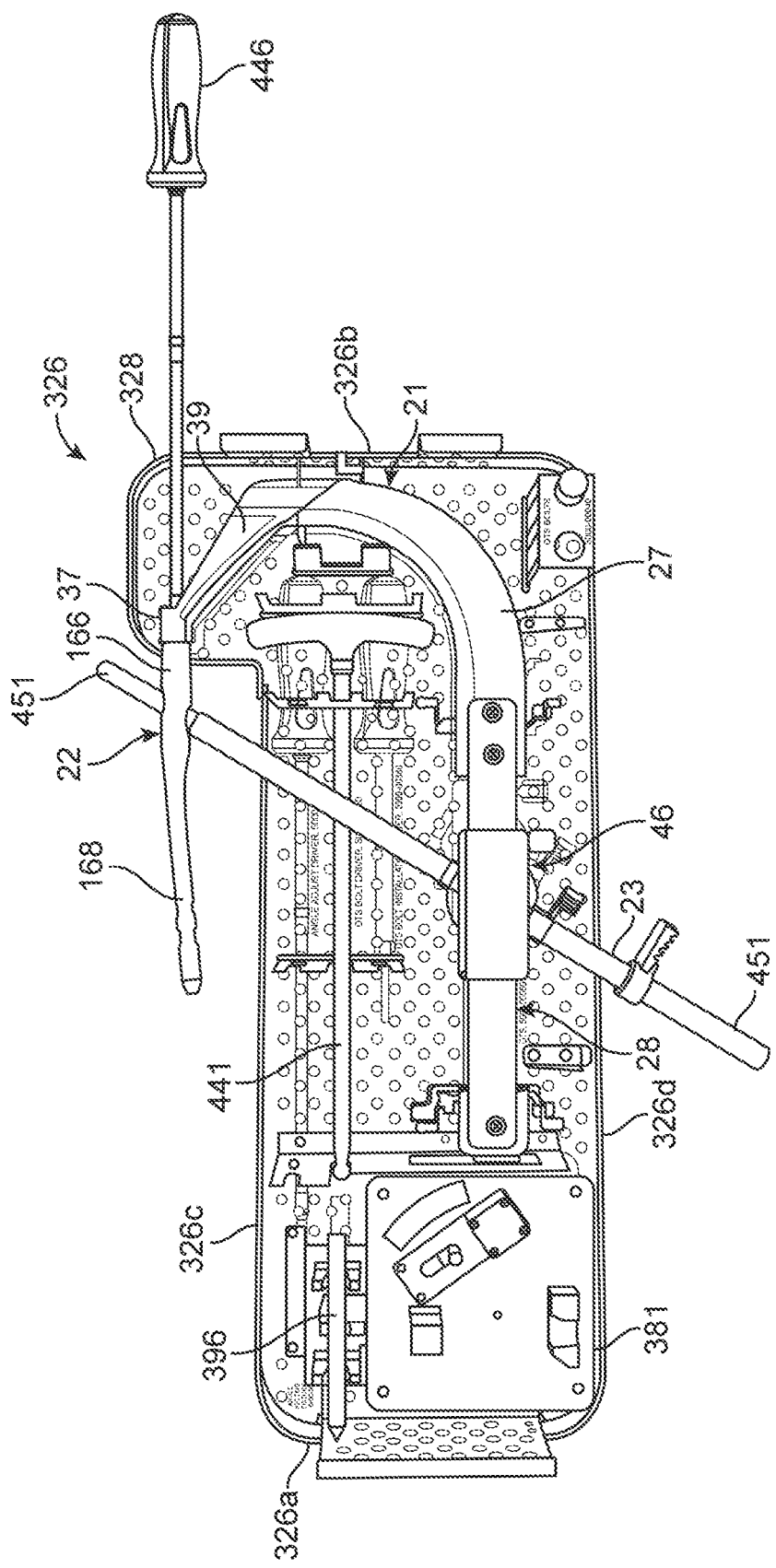
FIG. 51 is an illustration of a third step of a further aspect of use of the instrument sub tray of FIG. 25.
Figure 52:
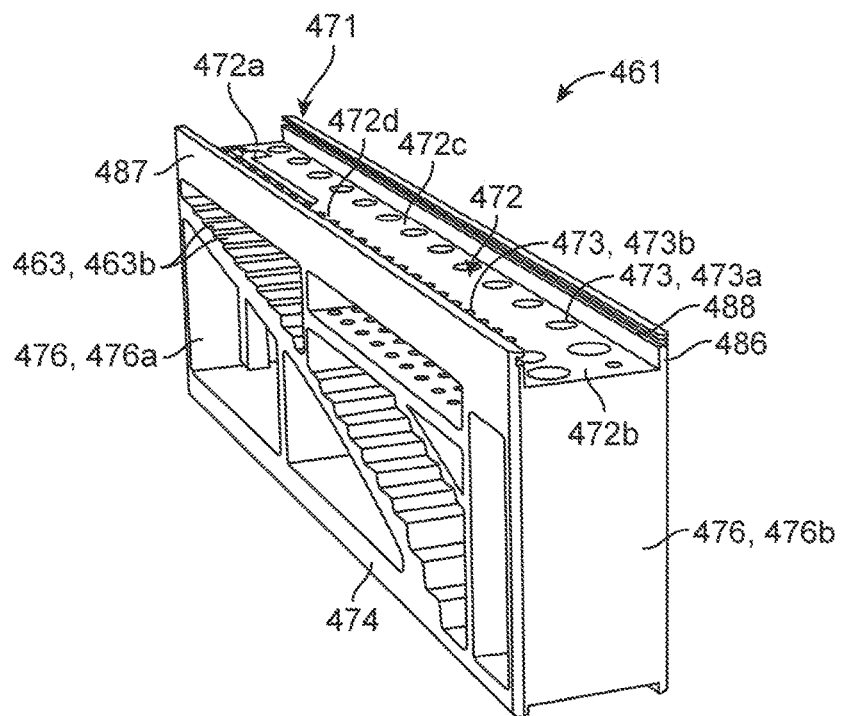
FIG. 52 is an end perspective view of the screw holder of the present invention with no screws therein.
Figure 53:
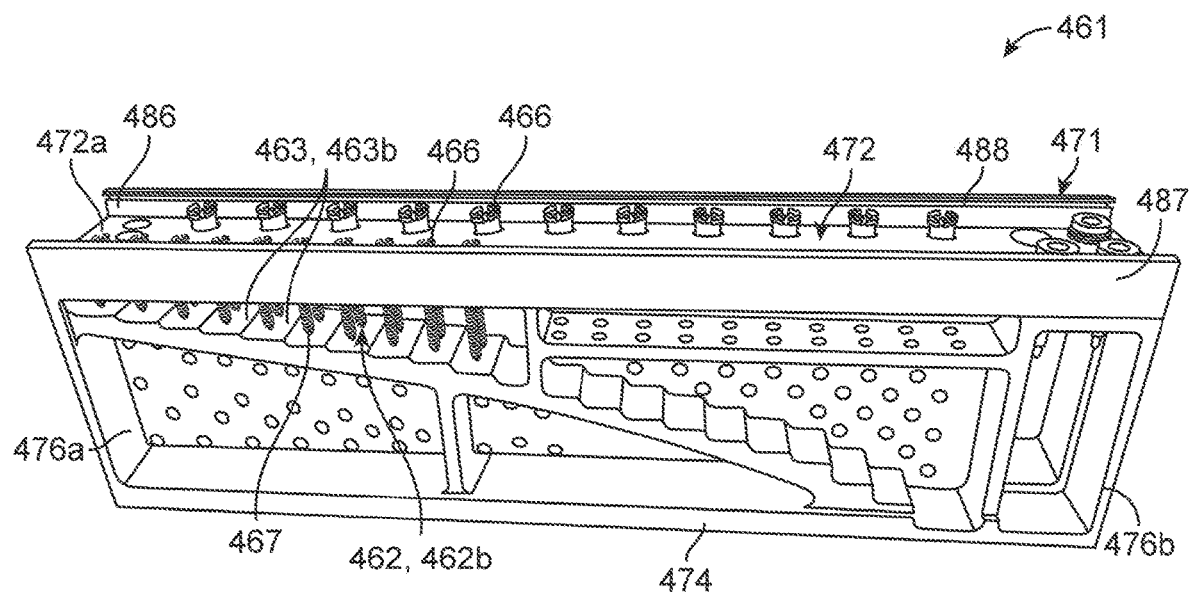
FIG. 53 is a first side perspective view of the screw holder of the present invention with some screws therein.
Figure 54:
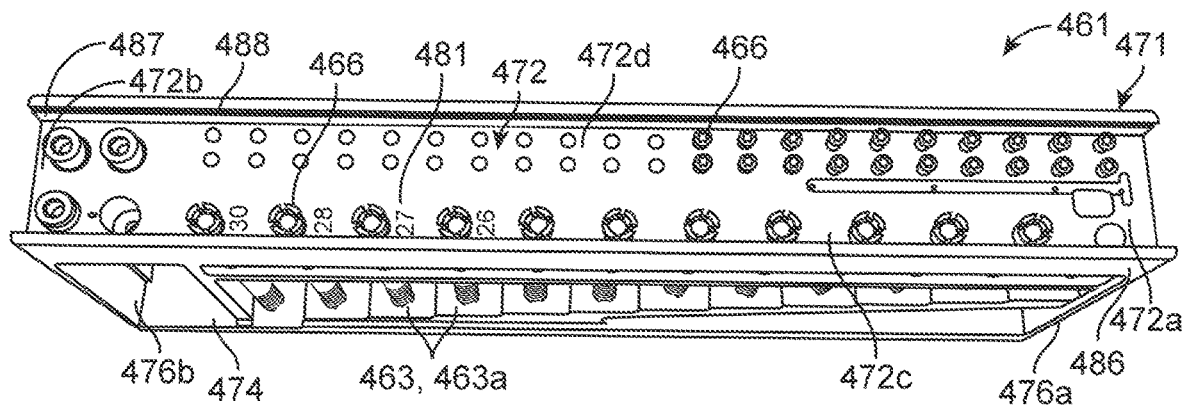
FIG. 54 is a top perspective view of the screw holder of FIG. 53.
Figure 55:
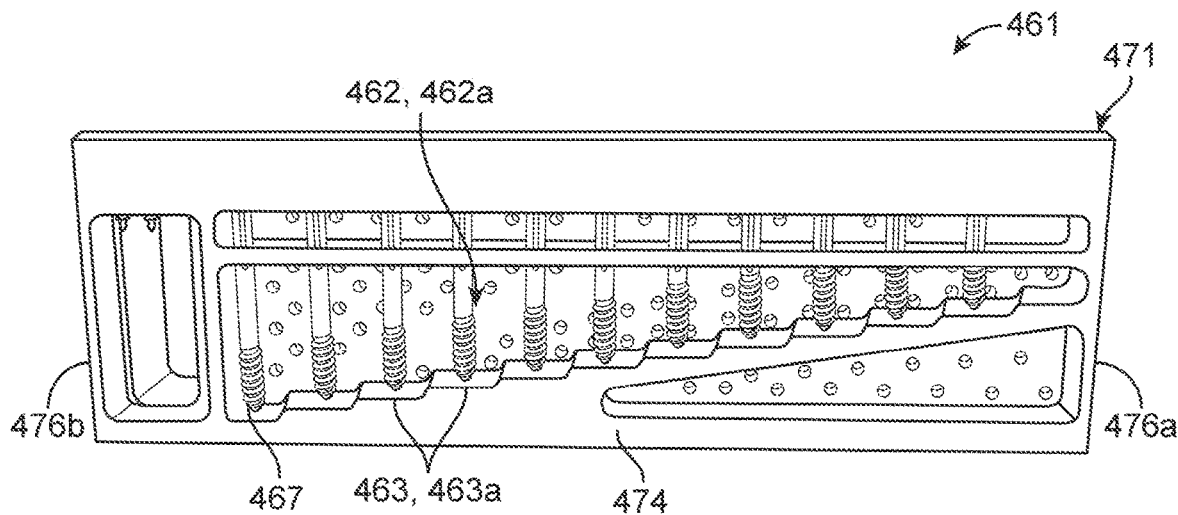
FIG. 55 is a second side perspective view of the screw holder of FIG. 53.
Figure 56:
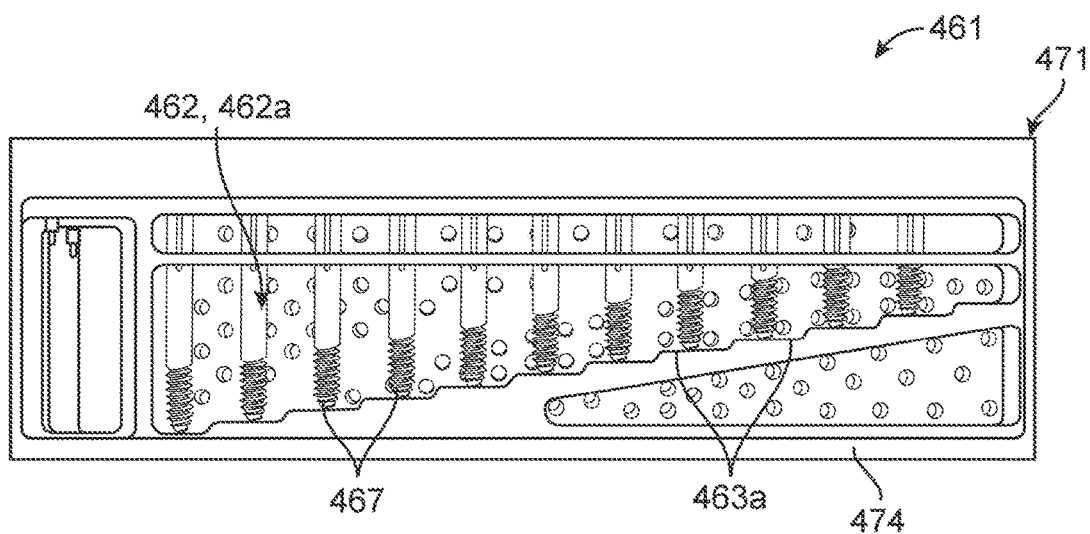
FIG. 56 is a second side elevational view of the screw holder of FIG. 53.

A method can be provided for preparing an intramedullary rod or other implantable device having an angularly adjustable aperture for receiving a fastener for implantation. In one step, the method can include attaching the intramedullary rod to a targeting device or other implant insertion device secured to a sterilization tray. For example as discussed above, intramedullary rod 22 can be attached to targeting device 21 while the targeting device 21 is attached to an instrument tray, such as sub tray 326 (see FIG. 48). The targeting device or other implant insertion device can have an angularly adjustable aperture for receiving a fastener sleeve. For example, targeting device 21 can have an angularly adjustable aperture 81 for receiving a fastener sleeve, such as fastener or guide sleeve 23. In one step, the method can include adjusting the angle of the angularly adjustable aperture in the implant insertion device secured to the sterilization tray to align with the aperture in the implantable device. For example, the angle of adjustable aperture 81 of targeting device 21 can be adjusted by moving targeting assembly 46 upwardly or downwardly on second portion 28 of the targeting device while the targeting device is secured to the instrument tray 326 (see FIGS. 49-50). The adjusting step can include inserting an elongate element through the adjustable aperture of the implant insertion device. For example, as shown in FIGS. 49-50, an elongate element such as fastener or guide sleeve 23 can be inserted through adjustable aperture 81 and moved with targeting assembly 46 during adjustment of the angle of aperture 81 relative to second portion 28. In any embodiment, the adjusting step can include inserting a fastener simulating element through the fastener sleeve and through the angularly adjustable hole of the implantable device. For example, a fastener simulating element 451 such as a leg screw trial can be inserted through fastener sleeve 23 while the fastener sleeve is disposed within aperture 81 of the targeting device 21 and the distal end of the leg screw trial 451 extended through angularly adjustable hole 25 of the intramedullary rod 22 (see FIG. 51). Such extension of a fastener simulating element 451 into the adjustable hole, for example aperture 25, of an intramedullary rod or other implantable device 22 can assist in determining that the angle of the adjustable aperture in the implant insertion device 21 is aligned with the adjustable hole of the implantable device 22. In any embodiment, the angle of the angularly adjustable aperture of the implant insertion device 21 can be adjusted before inserting the elongate element, for example guide sleeve 23, through the adjustable aperture of the implant insertion device, for example adjustable aperture 81 of device 21.

The method can include adjusting the angle of the aperture in the implantable device prior to attaching the implantable device to the implant insertion device. For example, as discussed above, the angle of angularly adjustable hole 25 of intramedullary rod 22 can be adjusted before the intramedullary rod 22 is attached to targeting device 21 secured to the instrument tray 326. In any embodiment, the step of adjusting the angle of the aperture in the implantable device can include mounting the implantable device on an angle adjustment mechanism, for example such a mechanism secured to an instrument tray. For example, as discussed above, the angle of the angularly adjustable angle of intramedullary rod 22 can be adjusted with angle adjustment mechanism 381, which can be secured to instrument tray 326.

In any embodiment, the method can include adjusting the angle of the angularly adjustable hole in the implantable device, while the implantable device is secured to the implant insertion device carried by or mounted on the instruments tray, in connection with the adjustment of the angularly adjustable aperture in the implant insertion device. For example, a suitable driver 446 can be utilized and extended through bolt 243, connector 37 and into the proximal end of head 166 of intramedullary rod 22 to adjust the angle of angularly adjustable hole 25 of the rod while the targeting device 21 is secured to the instruments tray (see FIG. 51).

After the implant insertion device has been secured to an implantable device, the implant insertion device with the implantable device coupled thereto can be removed from the instruments tray for use. Such removal for use can occur without any prior adjustment of the angularly adjustable hole of the implantable device or the angularly adjustable aperture of the implant insertion device, either before or after securement of the implant insertion device to the implantable device.

An apparatus 461 can be provided for curing, holding, capturing or any combination of the foregoing a plurality of implants or devices 462 utilizable in a medical procedure. Such implants or devices 462 can include, for example, screws, guide wires, k-wires, caps, nails, bolts, rods, or any combination of the foregoing. For simplicity, the apparatus 461 is described and illustrated herein with respect to screws. In any embodiment, the apparatus can be provided with stepped surfaces 463 for respectively supporting a plurality of screws or other implants 462 of different shapes carried by the apparatus so as to facilitate proper length, width, height, shape or other unique design feature identification of the plurality of screws or other implants (see FIGS. 52-56). Each of the plurality of screws or other implants 462 can have a different shape, for example a different length, width, height or other unique design feature, and each can have a head 466 at one end and an opposite end 467, such as a distal or free end. In any embodiment, for example when the implant is a screw, the opposite end 467 can be externally threaded. Each of the plurality of screws or other implants 462 may have a different width. In any embodiment, the plurality of implants can be a plurality of screws 462 utilized with an implantable device, for example an intramedullary rod such as intramedullary rod 22. The plurality of screws can include a first plurality 462a of fasteners, lag screws or caps and a second plurality 462b of smaller screws utilized for securing a distal end of the intramedullary rod 22 to a bone. For example, the first plurality of screws 462a can be a plurality of different-sized fasteners 24 for use in adjustable transverse hole 25 of the rod 22 and the second plurality of screws 462b can be a plurality of different-sized screws utilized at the distal end of intramedullary rod 22. It is appreciated that the apparatus 461 can be configured to carry more than two pluralities of screws or other implants 462. For example, the apparatus 461 can be configured any number of plurality of screws or other implants 462, for example first through third plurality of screws or other implants or first through n plurality of screws or other implants.

In any embodiment, the apparatus, which can be referred to as a screw or implant holder or caddy 461, can include a support body 471 having a horizontal or other plate 472 provided with a plurality of openings 473, for example holes or slots, adapted for respectively receiving a plurality of screws or other implants 462. The plate 472 can have first and second opposite ends 472a, 472b and first and second sides 472c, 472d extending between the opposite ends. In any embodiment, the plate 472 can be rectangular when viewed in plan and supported above a base plate 474 by one or more support members 476. In any embodiment, the support members 476 can include first and second opposite end members 476a, 476b. In any embodiment, the horizontal, top or other plate 472, the base plate 474, and the first and second end members 476a, 476b can form a rectangular when viewed in plan (see FIGS. 53, 55 and 56).

In any embodiment, the plate 472 can be provided with a first plurality of holes or other openings 473a for receiving a first plurality of different-sized fasteners or other implants 24 and a second plurality of holes or other openings 473b for receiving a second plurality of different-sized distal screws or other implants, for example for use with intramedullary rod 22. The body 471 can include a plurality of horizontal or other surfaces 463, for example stepped surfaces, respectively underlying at least one of the plurality of openings in the plate 472 for supporting the respective ends 467 of the plurality of implants when such implants are disposed in the plurality of openings in the top plate 472. Each of the plurality of horizontal or other surfaces 463 underlying the plate 472 can be spaced below the plate a distance corresponding to the length or other distinctive shape of the respective implant 462 so that the heads 466 of the plurality of implants are aligned in a horizontal or other plane when the ends 467 of the plurality of devices are respectively supported by such horizontal or other surfaces 463. In any embodiment, the plane can be parallel to the plate 472 and spaced above the plate. In any embodiment, the plurality of surfaces 463 can be arranged in a stepped configuration so that the plurality of implants 462 can be linearly arranged in the plate 472 according to length or other shape. In any embodiment, the plurality of surfaces 463 can be spaced below the plate 472 a distance corresponding to the length or other distinctive shape of the respective implant 462 so that the heads 466 of each of the plurality of implants are spaced above the plate to facilitate removal of each of the plurality of implants from the respective opening 473. In any embodiment, a first plurality of such surfaces 463a underlie the first plurality of openings 473a and a second plurality 463b of such surfaces underlie the second plurality of openings 473b.

In any embodiment, at least one of the plurality of openings 473 in the plate is linearly aligned along the plate 472. In any embodiment, the first plurality of openings 473a for the first plurality of implants 462a are linearly aligned along a first side 472c of the plate and the second plurality of openings 473b for the second plurality of implants 462b are linearly aligned along a second side 472d of the plate. In any embodiment, the first plurality of surfaces 463a can extend along a first side of the body underlying the first plurality of openings 473a and the second plurality of surfaces 463b can extend along a second side of the body underlying the second plurality of openings 473b.

In any embodiment, the plate 472 can include indicia 481 of any suitable type in the vicinity of each of at least one of the plurality of holes or other openings 473 identifying one or more of each of the respective plurality of screws or other implants 462.

The body 471 can be formed in any suitable manner from any number of parts or pieces. For example, in any embodiment, the body 471 can be injection molded as a single piece of plastic. In any embodiment, the body 471 can be manufactured by machining from a block of plastic or any other suitable material known to a person in the art. In any embodiment, the body 471 can be made from multiple pieces that are glued, melted or otherwise fastened together in any suitable manner. In any embodiment, a separate cover 482 can be provided for overlying the top or other plate 472. In this regard, a first side wall 486 and a second side wall 487 can extend above the top or other plate 472 along the first and second sides of the body and each include a horizontal or other groove 488 spaced above the top or other plate 472 for slidably receiving the cover 482. In any embodiment, a separate cover (not shown) can be provided for overlying the sides or sides plates of the body.

The apparatus can be sized to be carried within the sterilizable tray assembly 302 of the invention. In any embodiment, the apparatus 461 can be carried within the main instrument tray 306, supported by the base layer 316 of such tray. For example, the apparatus 461 can nest with the sub tray 326 within the main instrument tray 306. For example, the body 471 can extend upwardly alongside the first main side 326c of the sub tray 326 and can have a length approximately corresponding to, but slightly less, than the distance between the first side 328a of the extension 328 of the sub tray and the first end 326a of the sub tray. In any embodiment, the apparatus 461 can have a height approximating but not greater than the depth of the cavity 307 of the main instrument tray 306. In any embodiment, the apparatus 461 can be a stand-alone apparatus, for example not carried by the sterilizable tray assembly 302, or can be carried by any other device or assembly.

In one aspect of the invention an apparatus for use with an implantable device having a proximal end that is threaded about a longitudinal axis and an implant insertion device having an end for coupling to the proximal end of the implantable device and a tool for threadedly coupling the implant insertion device to the implantable device can be provided and include a sterilizable tray having a base, at least one fixture connected to the tray adapted for removably securing the implant insertion device to the tray, the tray being free of a first wall portion for permitting the proximal end of the implantable device to axially align with the end of the implant insertion device for coupling to the implant insertion device and being free of a second wall portion for permitting the tool to axially align with the end of the implant insertion device so as to threadedly couple the implant insertion device to the implantable device.

The base can have a perimeter, the tray having a wall around at least a portion of the perimeter, the wall being provided with a first opening for permitting the proximal end of the implantable device to axially align with the end of the implant insertion device for coupling to the implant insertion device and a second opening for permitting the tool to axially align with the end of the implant insertion device. The second opening in the wall can be opposite the first opening in the wall. The base can have an extension with first and second opposite sides for receiving the end of the implant insertion device and the first opening in the wall can be in the first side of the extension and the second opening in the wall can be in the second side of the extension. The implantable device can be an intramedullary nail and the implant insertion device can be a targeting device. The at least one fixture can include a plurality of spaced-apart clips secured to the base.

In one aspect of the invention, a method of preparing an implantable device having a proximal end for use with an implant insertion device having an end and secured to a sterilizable instruments tray can be provided and include aligning the proximal end of the implantable device with the end of the implant insertion device and coupling the end of the implant insertion device secured to the instruments tray to the implantable device.

The coupling step can include threadedly coupling the implant insertion device to the implantable device. The threadedly coupling step can include threading a bolt to the proximal end of the implantable device. The implantable device can be an intramedullary nail and the implant insertion device is a targeting device. The method can include the step of inserting an elongate element through a transverse aperture in the targeting device and then inserting the elongate element through a transverse aperture in the intramedullary nail. The method can include the step of adjusting the angle of the transverse aperture in the targeting device before inserting the elongate element through the transverse aperture in the intramedullary nail. The method can include the step of adjusting an angle of a transverse aperture in the implant insertion device secured to the instruments tray to align with an angle of a transverse aperture in the implantable device. The method can include the step of removing the implant insertion device with the implantable device coupled thereto from the instruments tray.

In one aspect of the invention, a method for preparing an intramedullary rod having an angularly adjustable aperture for receiving a fastener for implantation can be provided and include adjusting the angle of the aperture in the intramedullary rod, attaching the intramedullary rod to a targeting device secured to a sterilization tray, the targeting device having an angularly adjustable aperture for receiving a fastener sleeve, and adjusting the angle of the aperture in the targeting device secured to the sterilization tray to align with the aperture in the intramedullary rod.

The step of adjusting the angle of the aperture in the targeting device can include inserting an elongate element through the aperture in the targeting device. The elongate element can be a fastener sleeve and the method can include inserting a fastener simulating element through the fastener sleeve and through the aperture in the intramedullary rod. The step of adjusting the angle of the aperture in the intramedullary rod can include mounting the intramedullary rod on an angle adjustment mechanism secured to the sterilization tray.

In one aspect of the invention, a tool for use with a threaded element for fastening an end of an implant insertion device to an implantable device having a threaded proximal end provided with an opening and a longitudinal bore extending into the proximal end from the opening can be provided and include a handle, an elongate shaft extending forwardly from the handle along a longitudinal axis, the elongate shaft having a free end provided with a driver centered on the longitudinal axis and adapted to engage the threaded element, an elongate guide extending forwardly of the driver along the longitudinal axis, the elongate guide being adapted to extend through the opening and into the bore for facilitating centering of the end of implant insertion device on the threaded proximal end of the implantable device.

The driver can be a hex driver. The elongate guide can be an elongate cylindrical guide. The driver can have a length and the elongate guide can have a length at least equal to the length of the driver. The elongate guide can have a length at least twice the length of the driver. The driver can have a transverse dimension and the elongate guide can have a transverse dimension less than the transverse dimension of the driver.

In one aspect of the invention, a method for attaching an end of an implant insertion device carrying a threaded element to a threaded proximal end of an implantable device provided with an opening in the proximal end and a bore extending distally from the opening, can be provided and include providing a tool having a handle and an opposite free end with a driver and an elongate guide extending forwardly of the driver, extending the elongate guide through the threaded element and the end of the implant insertion device and into the opening in the threaded proximal end, further extending the elongate guide into the bore for facilitating centering of the threaded element on the threaded proximal end of the implantable drive and rotating the tool to cause the driver to rotate the threaded element and secure the threaded element and the end of the implant insertion device to the threaded proximal end of the implantable device.

The threaded element can be distinct of the implant insertion device. The end of the implant insertion device can be provided with a recess for receiving the threaded element. The threaded proximal end of the implantable device can be internally threaded and wherein the threaded element is a bolt having a first end provided with a drive recess and an opposite second end that is externally threaded.

In one aspect of the invention, a mechanism for use with an implantable device having an angularly adjustable transverse hole and an elongate element resembling a fastener having an end can be provided and include a base, at least one fixture connected to the base adapted for removably securing the implantable device to the base and an arcuate scale with angle indicia wherein when the implantable device is secured to the base with the at least one fixture and the elongate element is inserted into the angularly adjustable transverse hole the end of the elongate element points at the indicia on the scale to indicate the angle of the angularly adjustable transverse hole.

The end of the elongate element can be pointed. The mechanism can include a spring mechanism carried by the base for engaging the elongate element and simulating a load on a fastener extending through the angularly adjustable transverse hole. The implantable device can have a head extending along a longitudinal axis and the at least one fixture can include an element for engaging the head to rotatably lock the implantable device about the longitudinal axis relative to the base.

In one aspect of the invention, a method for determining an angle of an angularly adjustable transverse hole in an implantable device for receiving a fastener can be provided and include securing the implantable device to a body, inserting an elongate element having an end through the angularly adjustable transverse hole and observing the end of the elongate element relative to the body to determine the angle of the angularly adjustable transverse hole.

The implantable device can be an intramedullary nail and the fastener is a screw. Angle indicia can be carried by the base and the observing step can include observing the end of the elongate element relative to the angle indicia to determine the angle of the angularly adjustable transverse hole. The end of the elongate element can be pointed. The method can include adjusting the angle of the angularly adjustable transverse hole while the implantable device is secured to the body. The implantable device can have a proximal end and a rotatable element carried by the proximal end and the adjusting step can include rotating the rotatable element. The adjusting step can include engaging the rotatable element with a tool to rotate the rotatable element. The implantable device can have a proximal end and the adjusting step can include engaging the proximal end with a tool to adjust the angle of the angularly adjustable transverse hole. The proximal end can have an opening and the adjusting step can include extending the tool into the opening in the proximal end. The implantable device can have a proximal end and an actuatable element carried within the proximal end and the adjusting step can include engaging the actuatable element.

In one aspect of the invention, an apparatus for carrying a plurality of implants utilizable in a medical procedure and each of different shape and having a head and an opposite end can be provided an include a support body including a plate provided with a plurality of openings adapted for respectively receiving the plurality of implants, the support body including a plurality of surfaces respectively underlying the plurality of openings for supporting the respective ends of the plurality of implants when disposed in the plurality of openings, each of the plurality of surfaces being spaced below the plate a distance corresponding to the shape of the respective implant so that the heads of the plurality of implants are the same height in one plane.

The plurality of openings can be linearly aligned along the plate. The plurality of surfaces can be arranged in a stepped configuration so that the plurality of implants are linearly arranged according to length. The plate can include indicia in the vicinity of each of the plurality of openings identifying the respective plurality of implants. Each of the plurality of surfaces can be spaced relative to the plate a distance corresponding to the shape of the respective implant so that the heads of each of the plurality of implants are spaced above the plate to facility removal of each of the plurality of implants from the respective opening. The plate can be a horizontal plate and each of the plurality of surfaces can be a horizontal surface. The plurality of openings can be a plurality of holes. The implants can be screws, guide wires, k-wires, caps, nails, bolts, rods or any combination of the foregoing.

We claim:

1. An apparatus for use with an implantable device having a proximal end that is threaded about a longitudinal axis and an implant insertion device having an end for coupling to the proximal end of the implantable device and a tool for threadedly securing the implant insertion device to the implantable device, comprising a sterilization tray having a base, at least one fixture permanently secured to the sterilization tray adapted for removably securing the implant insertion device to the sterilization tray, the sterilization tray having at least one side opening and the at least one fixture being configured relative to the sterilization tray for aligning the end of the implant insertion device with the at least one side opening so as to permit the proximal end of the implantable device to extend through the at least one side opening to engage the end of the implant insertion device and permit the tool to extend through the at least one side opening for threadedly securing the implantable device to the implant insertion device.

2. The apparatus of claim 1, wherein the base has a perimeter, the sterilization tray having a wall around at least a portion of the perimeter provided with the at least one side opening, the at least one side opening in the wall including a first opening for permitting the proximal end of the implantable device to engage the end of the implant insertion device and a second opening for permitting the tool to axially align with the end of the implant insertion device.

3. The apparatus of claim 2, wherein the second opening in the wall is opposite the first opening in the wall.

4. The apparatus of claim 2, wherein the base has an extension with first and second opposite sides for receiving the end of the implant insertion device and wherein the first opening in the wall is in the first side of the extension and the second opening in the wall is in the second side of the extension.

5. The apparatus of claim 1, wherein the implantable device is an intramedullary nail and wherein the implant insertion device is a targeting device.

6. The apparatus of claim 1, wherein the at least one fixture includes a plurality of spaced-apart clips permanently secured to the base.

7. The apparatus of claim 1, further comprising a container for carrying the sterilization tray and an additional apparatus adapted for carrying a plurality of implants utilizable in a medical procedure and each of different shape and having a head and an opposite end, the additional apparatus carried by the container and including a support body having a plate provided with a plurality of openings for respectively receiving the plurality of implants, the support body including a plurality of surfaces respectively underlying the plurality of openings for supporting the respective ends of the plurality of implants when disposed in the plurality of openings, each of the plurality of surfaces being spaced below the plate a distance corresponding to the shape of the respective implant so that the heads of the plurality of implants are the same height in one plane.

8. The apparatus of claim 7, wherein the plurality of openings are linearly aligned along the plate.

9. The apparatus of claim 8, wherein the plurality of surfaces are arranged in a stepped configuration so that the plurality of implants are linearly arranged according to length.

10. The apparatus of claim 7, wherein the plate includes indicia in the vicinity of each of the plurality of openings identifying the respective plurality of implants.

11. The apparatus of claim 7, wherein each of the plurality of surfaces is spaced relative to the plate a distance corresponding to the shape of the respective implant so that the heads of each of the plurality of implants are spaced above the plate to facilitate removal of each of the plurality of implants from the respective opening.

12. The apparatus of claim 7, wherein the implants are selected from the group consisting of screws, guide wires, k-wires, caps, nails, bolts, rods and any combination of the foregoing.

13. An apparatus for use with an implantable device having a proximal end that is threaded about a longitudinal axis and an implant insertion device having an end for coupling to the proximal end of the implantable device, comprising a sterilization tray having a base, a mechanism having an angularly adjustable transverse hole and an elongate element resembling a fastener in appearance and having an end, the mechanism including an additional base carried by the sterilization tray, at least one fixture connected to the additional base adapted for removably securing the implantable device to the additional base and an arcuate scale with angle indicia wherein when the implantable device is secured to the additional base with the at least one fixture and the elongate element is inserted into the angularly adjustable transverse hole the end of the elongate element points at the indicia on the scale to indicate the angle of the angularly adjustable transverse hole.

14. The apparatus of claim 13, in combination with the elongate element.

15. The apparatus of claim 14, wherein the end of the elongate element is pointed.

16. The apparatus of claim 13, further comprising a spring mechanism carried by the additional base for engaging the elongate element and simulating a load on a fastener extending through the angularly adjustable transverse hole.

17. The apparatus of claim 13, for use with the implantable device having a head extending along a longitudinal axis, wherein the at least one fixture includes an element for engaging the head to rotatably lock the implantable device about the longitudinal axis relative to the additional base.

18. An apparatus for use with an intramedullary nail having a proximal end that is threaded about a longitudinal axis and a targeting device having an end for coupling to the proximal end of the intramedullary nail and a tool for threadedly securing the targeting device to the intramedullary nail, comprising a sterilization tray having a base with a perimeter, the sterilization tray having a wall around at least a portion of the perimeter, at least one fixture permanently secured to the sterilization tray adapted for removably securing the targeting device to the sterilization tray, the wall being provided with a first opening and an opposite second opening, the at least one fixture being configured relative to the sterilization tray for aligning the end of the targeting device with the first opening to permit the proximal end of the intramedullary nail to extend through the first opening to engage the end of the targeting device and for aligning the end of the targeting device with the second opening to permit the tool to extend through the second opening for threadedly securing the intramedullary nail to the targeting device.

19. The apparatus of claim 18, wherein the base has an extension with first and second opposite sides for receiving the end of the targeting device and wherein the first opening in the wall is in the first side of the extension and the second opening in the wall is in the second side of the extension.

* * * * *